US008916694B2

(12) United States Patent
Crooke et al.

(10) Patent No.: US 8,916,694 B2
(45) Date of Patent: Dec. 23, 2014

(54) SNPS OF APOLIPOPROTEIN B AND MODULATION OF THEIR EXPRESSION

(75) Inventors: Rosanne M. Crooke, Carlsbad, CA (US); Mark J. Graham, San Clemente, CA (US); Steven Mah, San Diego, CA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 13/016,917

(22) Filed: Jan. 28, 2011

(65) Prior Publication Data

US 2011/0319469 A1 Dec. 29, 2011

Related U.S. Application Data

(63) Continuation of application No. 11/124,020, filed on May 5, 2005, now abandoned.

(60) Provisional application No. 60/568,409, filed on May 5, 2004.

(51) Int. Cl.
*C07H 21/02* (2006.01)
*A01N 43/04* (2006.01)
*C12Q 1/68* (2006.01)

(52) U.S. Cl.
CPC ........ *C12Q 1/6883* (2013.01); *C12Q 2600/158* (2013.01); *C12Q 2600/106* (2013.01); *C12Q 2600/156* (2013.01); *C12Q 2600/136* (2013.01)
USPC ....... 536/23.1; 536/25.3; 536/24.5; 514/44 R; 514/44 A; 435/455

(58) Field of Classification Search
CPC ........ C07H 21/00; C07H 21/02; C12N 15/11; C12N 15/111; C12N 15/113; C12N 15/1135; C12P 19/34
USPC ......... 536/23.1, 25.3, 24.5; 514/441; 435/455
See application file for complete search history.

(56) References Cited

U.S. PATENT DOCUMENTS

| | | | |
|---|---|---|---|
| 5,220,006 A | 6/1993 | Ross et al. | |
| 5,434,058 A | 7/1995 | Davidson | |
| 5,618,674 A | 4/1997 | Sanchez-Pescador et al. | |
| 5,656,612 A | 8/1997 | Monia | |
| 5,712,257 A | 1/1998 | Carter | |
| 5,786,206 A | 7/1998 | Smith et al. | |
| 5,801,154 A | 9/1998 | Baracchini et al. | |
| 5,877,009 A | 3/1999 | Zannis et al. | |
| 5,945,290 A | 8/1999 | Cowsert | |
| 5,998,148 A | 12/1999 | Bennett et al. | |
| 6,010,849 A | 1/2000 | Edwards et al. | |
| 6,033,910 A | 3/2000 | Monia et al. | |
| 6,096,516 A | 8/2000 | Kwak et al. | |
| 6,156,315 A | 12/2000 | Goldberg et al. | |
| 6,172,216 B1 | 1/2001 | Bennett et al. | |
| 6,184,212 B1 | 2/2001 | Miraglia et al. | |
| 6,235,470 B1 | 5/2001 | Sidransky | |
| 6,448,079 B1 | 9/2002 | Monia et al. | |
| 6,500,672 B1 | 12/2002 | Sladek et al. | |
| 6,512,161 B1 | 1/2003 | Rouy et al. | |
| 6,534,277 B1 | 3/2003 | Hancock et al. | |
| 6,582,908 B2 | 6/2003 | Fodor et al. | |
| 6,660,737 B2 | 12/2003 | Almstead et al. | |
| 6,670,461 B1 | 12/2003 | Wengel et al. | |
| 6,852,536 B2 | 2/2005 | Dobie et al. | |
| 6,878,729 B2 | 4/2005 | Almstead et al. | |
| 6,949,367 B1 | 9/2005 | Dempcy et al. | |
| 7,407,943 B2 | 8/2008 | Crooke et al. | |
| 7,511,131 B2 | 3/2009 | Crooke et al. | |
| 7,598,227 B2 | 10/2009 | Crooke et al. | |
| 7,750,141 B2 | 7/2010 | Crooke et al. | |
| 2001/0053519 A1 | 12/2001 | Fodor et al. | |
| 2002/0068708 A1 | 6/2002 | Wengel et al. | |
| 2002/0123617 A1 | 9/2002 | Starling et al. | |
| 2003/0008373 A1 | 1/2003 | Bartel et al. | |
| 2003/0064950 A1 | 4/2003 | Ntambi et al. | |
| 2003/0083280 A1 | 5/2003 | Crooke et al. | |
| 2003/0087853 A1 | 5/2003 | Crooke et al. | |
| 2003/0215943 A1 | 11/2003 | Crooke et al. | |
| 2003/0228597 A1 | 12/2003 | Cowsert et al. | |
| 2003/0228613 A1 | 12/2003 | Bornarth et al. | |
| 2004/0171566 A1 | 9/2004 | Monia et al. | |
| 2004/0208856 A1 | 10/2004 | Crooke et al. | |
| 2004/0209838 A1 | 10/2004 | Monia et al. | |
| 2004/0214325 A1 | 10/2004 | Crooke et al. | |
| 2004/0241651 A1 | 12/2004 | Olek et al. | |
| 2004/0266714 A1 | 12/2004 | Freier et al. | |
| 2005/0009088 A1 | 1/2005 | Crooke et al. | |

(Continued)

FOREIGN PATENT DOCUMENTS

| EP | 0 332 435 | 9/1989 |
|---|---|---|
| EP | 0 530 794 | 3/1993 |

(Continued)

OTHER PUBLICATIONS

U.S. Appl. No. 60/159,462, Eggeman et al.
Agrawal et al., "Antisense therapeutics: is it as simple as complementary base recognition?" Molecular Medicine Today (2000) 6: 72-81.
Bennett et al., "Antisense Oligonucleotides as a Tool for Gene Functionalization and Target Validation?" Biochimica et Biophysica Acta (1999) 1489:18-30.
Boren et al., "A simple and efficient method for making site-directed mutants, deletions, and fusions of large DNA such as PI and BAC clones" Genome Research (1996) 11:1123-1130.
Branch et al., "A good antisense molecule is hard to find," TIBS (1998) 23:45-50.
Burnett, "Drug evaluation: ISIS-301012, an antisense oligonucleotide for the treatment of hypercholesterolemia" Current Opinion in Molecular Therapeutics (2006) 8(5):461-467.

(Continued)

*Primary Examiner* — Jennifer McDonald
(74) *Attorney, Agent, or Firm* — Jones Day

(57) ABSTRACT

Compounds, compositions and methods are provided for modulating the expression of apolipoprotein B. The compositions comprise oligonucleotides, targeted to nucleic acid encoding apolipoprotein B. Methods of using these compounds for modulation of apolipoprotein B expression and for diagnosis and treatment of diseases and conditions associated with expression of apolipoprotein B are provided.

33 Claims, No Drawings

(56) References Cited

U.S. PATENT DOCUMENTS

| | | |
|---|---|---|
| 2005/0014713 A1 | 1/2005 | Freier |
| 2005/0043524 A1 | 2/2005 | Bhanot et al. |
| 2005/0130923 A1 | 6/2005 | Bhat et al. |
| 2005/0164271 A1 | 7/2005 | Bhanot et al. |
| 2005/0272680 A1 | 12/2005 | Bhanot et al. |
| 2005/0287558 A1 | 12/2005 | Crooke et al. |
| 2006/0009410 A1 | 1/2006 | Crooke et al. |
| 2006/0025373 A1 | 2/2006 | Bhanot et al. |
| 2006/0035858 A1 | 2/2006 | Geary et al. |
| 2007/0031844 A1 | 2/2007 | Khvorova et al. |
| 2007/0087987 A1 | 4/2007 | Monia et al. |
| 2007/0238688 A1 | 10/2007 | Bhanot et al. |
| 2007/0238689 A1 | 10/2007 | Bhanot et al. |
| 2008/0146788 A1 | 6/2008 | Bhat et al. |
| 2008/0242629 A1 | 10/2008 | Crooke et al. |
| 2009/0306180 A1 | 12/2009 | Bhanot et al. |
| 2009/0326040 A1 | 12/2009 | Geary et al. |
| 2010/0297105 A1 | 11/2010 | Geary et al. |
| 2010/0331390 A1 | 12/2010 | Crooke et al. |
| 2011/0319469 A1 | 12/2011 | Crooke et al. |
| 2012/0115926 A1 | 5/2012 | Geary et al. |
| 2012/0129911 A1 | 5/2012 | Sacks et al. |

FOREIGN PATENT DOCUMENTS

| | | |
|---|---|---|
| EP | 0 911 344 | 4/1999 |
| EP | 1 239 051 | 9/2002 |
| JP | 2002355074 | 12/2002 |
| WO | WO 92/10590 | 6/1992 |
| WO | WO 94/13794 A1 | 6/1994 |
| WO | WO 97/20924 | 6/1997 |
| WO | WO 97/35538 A2 | 10/1997 |
| WO | WO 98/20166 | 5/1998 |
| WO | WO 98/32846 | 7/1998 |
| WO | WO 98/36641 | 8/1998 |
| WO | WO 99/14226 | 3/1999 |
| WO | WO 99/18237 | 4/1999 |
| WO | WO 99/18986 | 4/1999 |
| WO | WO 99/35241 | 7/1999 |
| WO | WO 00/00504 | 1/2000 |
| WO | WO 00/56916 | 9/2000 |
| WO | WO 00/56920 | 9/2000 |
| WO | WO 01/12789 | 2/2001 |
| WO | WO 01/30354 A1 | 5/2001 |
| WO | WO 01/30395 A1 | 5/2001 |
| WO | WO 01/52902 A1 | 7/2001 |
| WO | WO 01/72765 A1 | 10/2001 |
| WO | WO 01/77384 | 10/2001 |
| WO | WO 02/26768 | 4/2002 |
| WO | WO 03/011887 | 2/2003 |
| WO | WO 03/074723 | 9/2003 |
| WO | WO 03/097097 | 11/2003 |
| WO | WO 03/097662 | 11/2003 |
| WO | WO 2004/044181 | 5/2004 |
| WO | WO 2004/077384 | 9/2004 |
| WO | WO 2004/093783 | 11/2004 |
| WO | WO 2005/049621 | 6/2005 |
| WO | WO 2006/020676 A2 | 2/2006 |
| WO | WO 2006/020676 A3 | 2/2006 |
| WO | WO 2007/031081 A2 | 3/2007 |
| WO | WO 2007/090071 A2 | 8/2007 |
| WO | WO 2007/131238 A2 | 11/2007 |
| WO | WO 2007/134181 | 11/2007 |
| WO | WO 2008/118883 A1 | 10/2008 |

OTHER PUBLICATIONS

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Chapter 1: Basic Principles of Antisense Therapeutics" Antisense Research and Applications (1998) 131:1-50.
Crooke, "Antisense oligonucleotides as therapeutics for hyperlipidaemias" Expert Opinion on Biological Therapy (2005) 5(7):907-917.
Davidson et al., "Apolipoprotein B: mRNA editing, lipoprotein assembly, and presecretory degradation" Annu. Rev. Nutr. (2000) 20:169-193.
De Mesmaeker et al., "Backbone modifications in oligonucleotides and peptide nucleic acid systems" Curr Opin Struct Biol (1995) 5:343-355.
DeCatarina et al., "Fatty Acid Modulation of Endothelial Activation" American Journal of Clinical Nutrition (2000) 71(suppl.):213S-223S.
Deeb et al., "Chromosomal localization of the human apolipoprotein B gene and detection of homologous RNA in monkey intestine" Proc. Natl. Acad. Sci. USA (1986) 83:419-422.
Eggerman et al., "Use of Oligonucleotides to Target Nucleic Acid Sequences Encoding Apolipoprotein B to Decrease Serum Apolipoprotein B and Cholesterol Levels" Federal Register (2000) 65:110.
Elias et al., "Decreased Production Rates of VLDL Triglycerides and ApoB-100 in Subjects Heterozygous for *Familial hypobetalipoproteinemia*," Metabolism of Triglycerides and ApoB-100 n FHBL, Arterioscler Therob Vase Biol., (1999)9:2714-2721.
EMBL Accession No. A23827, Apr. 2, 1995.
EMBL Accession No. A13426, Oct. 5, 1994.
EMBL Accession No. A97152, Jan. 26, 2000.
EMBL Accession No. AR 152836, Aug. 9, 2001.
EMBL Accession No. 113154, Aug. 2, 1995.
EMBL Accession No. L27195, Jan. 6, 1994.
EMBL Accession No. L24258, Sep. 18, 1993.
Farese et al., "Knockout of the mouse apolipoprotein B gene results in embryonic lethality in homozygotes and protection against diet-induced hypercholesterolemia in heterozygotes" Proc. Natl. Acad. Sci. USA (1995) 92:1774-1778.
Fluiter K., et al., "On the in vitro and in vivo properties of four locked nucleic acid nucleotides incorporated into an anti-h-ras antisense oligonucleotide," Chembiochem—A European Journal of Chemical Biology, vol. 6, No. 6, Jun. 2005, pp. 1104-1109.
Frieden M., et al, "Expanding the design horizon of antisense oligonucleotides with alpha-L-LNA," Nucleic Acids Research, Oxford University Press, Surrey, GB, vol. 31, No. 21, Nov. 1, 2003, pp. 6365-6372.
Ganji et al., "Niacin and cholesterol: role in cardiovascular disease (Review)" The Journal of Nutritional Biochemistry (2003) 14:293-305.
Geary et al., "Pharmacokinetics of a Tumor Necrosis Factor-α Phosphorothioate 2'-O(2-Methoxyethyl) Modified Antisense Oligonucleotide: Comparison Across Species," Drug Metab Dispos 2003:31:1419-1428.
GenBank Accession No. NM_000384, Oct. 31, 2000, Huang et al.
GENESEQ Accession No. AAA07969, Jan. 29, 2001.
GENESEQ Accession No. AAA28208, Jan. 29, 2001.
GENESEQ Accession No. AAV39607, Sep. 28, 1998.
GENESEQ Accession No. AAX89306, Sep. 21, 1999. (from WO 99/35241).
Graham et al., "Pharmacological Inhibition of PCSK9 in Hyperlipiemic Mice Significantly Reduces Serum LDL-C While Increasing Hepatic Low-Density Lipoprotein Receptor Protein Abundance," Jun. 2007, vol. 27, No. 6, p. E36.
Hajjar et al., "The role of lipoprotein(a) in atherogenesis and thrombosis" Annu. Rev. Med. (1996) 47:423-442.
Hammond et al., "Post-transcriptional gene silencing by double-stranded RNA" Nature Reviews Genetics (2001) 2:110-119.
Huang et al., "Hypobetalipoproteinemia due to an apolipoprotein B gene exon 21 deletion derived by Alu-Alu recombination" Journal of Biological Chemistry (1989) 264:11394-11400. (Genbank NM_000384).
Iijima et al., "Red Wine Polyphenols Inhibit Vascular Smooth Muscle Cell Migration Through Two Distinct Signaling Pathways" Circulation (2002) 105(20):2404-2410.
Innerarity et al., "Familial defective apolipoprotein B-100: low density lipoproteins with abnormal receptor binding" Proc. Natl. Acad. Sci. USA (1987) 84:6919-6923.

(56) References Cited

OTHER PUBLICATIONS

James, W., "Towards gene-inhibition therapy; a review of progress and prospects in the field of antiviral antisense nucleic acids and ribozymes," Antiviral Chemistry and Chemotherapy, Apr. 191, vol. 2, No. 4, pp. 191-214.
Jen et al., "Suppression of Gene Expression by Targeted Disruption of Messenger RNA: Available Options and Current Strategies" Stem Cells (2000) 18:307-319.
Kastelein et al., "Potent reduction of apolipoprotein B and low-density lipoprotein cholesterol by short-term administration of an antisense inhibitor of apolipoprotein B" Circulation (2006) 114(16):1729-1735.
Katan et al., "Characteristics of human hypo- and hyperresponders to dietary cholesterol" Am. J. Epidemiol. (1987) 125:387-399.
Kim et al., "Genetically modified mice for the study of apolipoprotein B," J. Lipid Res. (1998) 39:703-723.
Koba et al., "Small dense LDL phenotype is associated with postprandial increases of large VLDL and remnant-like particles in patients with acute myocardial infarction" Atherosclerosis (2003) 170:131-140.
Latorra et al., "Enhanced allele-specific PCR discrimination in SNP genotyping using 3' locked nucleic acid (LNA) primers," Human Mutation (2003) 22:79-85.
Law et al., "Human apolipoprotein B-100: cloning, analysis of liver mRNA, and assignment of the gene to chromosome 2," Proc. Natl. Acad. Sci. USA (1985) 82:8340-8344.
Lemonidis, et al., "Abstracts of the 11$^{th}$ International Congress on Cardiovascular Pharmacotherapy. Montreal, Canada, May 18-21, 2002," Cardiovascular Drugs and Therapy/Sponsored by the International Society of Cardiovascular Pharmacotherapy (2002) 16, Suppl. 1:471, SP002565482.
Ma et al., "Synthetic oligonucleotides as therapeutics: the coming age," Biotechnology Annual Review (2000) 5:155-196.
Maxwell et al., "Proprotein Convertase Subtilisin Kexin 9: The Third Locus Implicated in Autosomal Dominant Hypercholesterolemia," Current Opinion in Lipidology, 2005, vol. 16, pp. 167-172.
McCormick et al., "Transgenic mice expressing human ApoB95 and ApoB97. Evidence that sequences within the carboxyl-terminal portion of human apoB100 are important for the assembly of lipoprotein," J. Biol. Chem. (1997) 272:23616-23622.
Milner et al., "Selecting effective antisense reagents on combinatorial oligonucleotide arrays," Nature Biotechnology, Jun. 1997, Bol. 15, pp. 537-541.
NCBI Search Results, (ISPH-0592) dated Oct. 30, 2007, Mamm. Genome 6 (3), 192-195 (1995).
New England Biolabs, 1998/1999 Catalog, pp. 121 and 284.
Nishina et al., "Synthetic low and high fat diets for the study of atherosclerosis in the mouse," J. Lipid Res. (1990) 31:859-869.
Nowak-Gottl et al., "Lipoprotein (a): its role in childhood thromboembolism," Pediatrics (1997) 99:1-3.
Parrish et al., "Functional anatomy of a dsRNA trigger: differential requirement for the two trigger strands in RNA interference," Molecular Cell (2000) 6:1077-1087.
Patil et al., "DNA-based therapeutics and DNA delivery systems: a comprehensive review," AAPS Journal (2005) 7:E61-E77.
Petersen et al., "Locked nucleic acid (LNA) recognition of RNA: NMR solution structures of LNA:RNA hybrids," Journal of the American Chemical Society (2002) 124:5974-5982.
PR Newswire, "Isis Pharmaceuticals initiates phase I study of second-generation antisense drug for cardiovascular disease" New York, Dec. 29, 2003.
Rojanasakul, Y, "Antisense Oligonucleotide Therapeutics: Drug Delivery and Targeting," Advanced Drug Delivery Reviews, (1996)18: 115-131, XP002913878.
Rosenson, "Clinical Role of LDL and HDL Subclasses and Apoliprotein Measurements," ACC Current Journal Review, 33-37 (2004).
Rossi et al., "Introductory Remarks on the General Application of Antisense RNAs and Ribozymes," Methods: A Companion to Methods in Enzymology (1993) 5:1-5.
Rubies-Prat et al., "Low-density lipoprotein particle size, triglyceride-rich lipoproteins, and glucose tolerance in non-diabetic men with essential hypertension" Clinical and Experimental Hypertension (2001) 23:489-500.
Sandkamp et al., "Lipoprotein(a) is an independent risk factor for myocardial infarction at a young age," Clin. Chem. (1990) 36:20-23.
Seed et al., "Relation of serum lipoprotein(a) concentration and apolipoprotein(a) phenotype to coronary heart disease in patients with familial hypercholesterolemia," N Engl J Med (1990) 322:1494-1498.
Senior, "Antisense inhibitor provides new treatment approach for hypercholesterolaemia" Drug Discovery Today (2002) 7:840-841.
Sewell et al.., "Phase I Trial of ISIS 104838, a 2'-Methoxyethyl Modified Antisense Oligonucleotide Targeting Tumor Necrosis Factor-α," The Journal of Pharmacology and Experimental Therapeutics (2002)303:1334-1343.
Simeonov et al., "Single nucleotide polymorphism genotyping using short, fluorescently labeled locked nucleic acid (LNA) probes and fluorescence polarization detection," Nucleic Acids Research (2002) 30:E9I.
Skrapari et al., "Glibenclamide improves postprandial hypertriglyceridaemia in type 2 diabetic patients by reducing chylomicrons but not the very low-density lipoprotein subfraction levels," Diabet Med (2001) 18:781-785.
Smith et al., "Rational selection fo antisense oligonucleotide sequences," European Journal of Pharmaceutical Sciences (2000) II(3):191-198, XP002372482.
Sniderman et al., "Substrate Delivery as a Determinant of Hepatic ApoB Secretion," Arterioscler Thromb Vase Biol., (1993)13:629-636.
Tanaka et al., "Regulation of apolipoprotein B production and secretion in response to the change of intracellular cholesteryl ester contents in rabbit hepatocytes," Journal of Biological Chemistry (1993) 268:12713-12718.
Tang et al., "The Inhibition of Antisense Oligodeoxynucleotides on the Expression of Apolipoprotein B in Rat Liver Cells," Zhongguo Dongmai Yinghua ZaZhi Bianjibu (Chinese Journal) (1999) 7:315-318.
Veniant et al., "Susceptibility to atherosclerosis in mice expressing exclusively apolipoprotein B48 or apolipoprotein B100," J. Clin. Invest. (1997) 100:180-188.
Vessby et al., "Diverging effects of cholestyramine on apolipoprotein B and lipoprotein Lp(a). A dose-response study of the effects of cholestyramine in hypercholesterolaemia," Atherosclerosis (1982) 44:61-71.
Wimberly, "Rosuvastatin (Crestor) A new statin for the treatment of dyslipidemia" PharmaNote (2003) 19:1-6.
Yu et al., "Pharmacokinetics and Pharmacodynamics of an Antisense Phosphorothioate Oligonucleotide Targeting Fas mRNA in Mice," J. Pharmacol. Exp. Ther. (2001)296:388-395.
Yu et al., "Antisense oligonucleotide inhibition of DGAT2 expression reduced hepatic steatosis diet-induded obese mice," Obesity Research ( 2003) 11(Suppl): A48.
Yu et al., "Antisense oligonucleotide reduction of DGAT2 expression improves hepatic steatosis and hyperlipidemia in obese mice," Hepatology (2005) 42(2):362-371.
Advisory Action for U.S. Appl. No. 09/920,033 dated Feb. 28, 2006.
Advisory Action for U.S. Appl. No. 09/920,033 dated Jun. 1, 2007.
Advisory Action for U.S. Appl. No. 10/712,795 dated Apr. 28, 2008.
Advisory Action for U.S. Appl. No. 10/920,612 dated Oct. 16, 2007.
Advisory Action for U.S. Appl. No. 10/920,612 dated Feb. 26, 2009.
Advisory Action for U.S. Appl. No. 11/124,020 dated Aug. 11, 2009.
Advisory Action for U.S. Appl. No. 11/200,710 dated Sep. 13, 2007.
Final Rejection Office Action for U.S. Appl. No. 09/920,033 dated Jul. 22, 2003.
Final Rejection Office Action for U.S. Appl. No. 09/920,033 dated Oct. 4, 2005.
Final Rejection Office Action for U.S. Appl. No. 09/920,033 dated Jan. 12, 2007.
Final Rejection Office Action for U.S. Appl. No. 09/920,033 dated Jan. 7, 2009.
Final Rejection Office Action for U.S. Appl. No. 10/147,196 dated Mar. 24, 2004.

(56) References Cited

OTHER PUBLICATIONS

Final Rejection Office Action for U.S. Appl. No. 10/147,196 dated Feb. 1, 2005.
Final Rejection Office Action for U.S. Appl. No. 10/147,196 dated May 17, 2006.
Final Rejection Office Action for U.S. Appl. No. 10/712,795 dated Apr. 9, 2007.
Final Rejection Office Action for U.S. Appl. No. 10/712,795 dated Jan. 8, 2008.
Final Rejection Office Action for U.S. Appl. No. 10/920,612 dated Mar. 28, 2007.
Final Rejection Office Action for U.S. Appl. No. 10/920,612 dated Aug. 7, 2008.
Final Rejection Office Action for U.S. Appl. No. 11/124,020 dated Jan. 26, 2009.
Final Rejection Office Action for U.S. Appl. No. 11/200,710 dated May 15, 2007.
Final Rejection Office Action for U.S. Appl. No. 11/200,710 dated Jan. 13, 2009.
Office Action for U.S. Appl. No. 09/920,033 dated Jan. 14, 2003.
Office Action for U.S. Appl. No. 09/920,033 dated Jan. 13, 2004.
Office Action for U.S. Appl. No. 09/920,033 dated Aug. 5, 2004.
Office Action for U.S. Appl. No. 09/920,033 dated Jan. 19, 2005.
Office Action for U.S. Appl. No. 09/920,033 dated Jun. 26, 2006.
Office Action for U.S. Appl. No. 09/920,033 dated Feb. 7, 2008.
Office Action for U.S. Appl. No. 09/920,033 dated Sep. 8, 2009.
Office Action for U.S. Appl. No. 10/147,196 dated Jul. 11, 2003.
Office Action for U.S. Appl. No. 10/147,196 dated Aug. 12, 2004.
Office Action for U.S. Appl. No. 10/147,196 dated Aug. 17, 2005.
Office Action for U.S. Appl. No. 10/147,196 dated Jan. 25, 2007.
Final Rejection Office Action for U.S. Appl. No. 11/124,020 dated Jul. 30, 2010.
Office Action for U.S. Appl. No. 10/712,795 dated Apr. 14, 2006.
Office Action for U.S. Appl. No. 10/712,795 dated Oct. 10, 2006.
Office Action for U.S. Appl. No. 10/712,795 dated Jul. 26, 2007.
Office Action for U.S. Appl. No. 10/920,612 dated Aug. 8, 2006.
Office Action for U.S. Appl. No. 10/920,612 dated Dec. 12, 2007.
Office Action for U.S. Appl. No. 11/123,656 dated Jun. 13, 2007.
Office Action for U.S. Appl. No. 11/123,656 dated Dec. 13, 2007.
Office Action for U.S. Appl. No. 11/123,656 dated Dec. 3, 2008.
Office Action for U.S. Appl. No. 11/123,6556 dated Sep. 9, 2009.
Office Action for U.S. Appl. No. 11/124,020 dated Jan. 14, 2008.
Non-final Office Action dated Dec. 2, 2009 for U.S. Appl. No. 11/124,020.
Non-final Office Action dated Oct. 28, 2009 for U.S. Appl. No. 11/969,096.
Final Office Action dated Jul. 15, 2010 for U.S. Appl. No. 11/969,096.
Office Action for U.S. Appl. No. 11/200,710 dated Sep. 28, 2006.
Office Action for U.S. Appl. No. 11/200,710 dated May 21, 2008.
Non-final Office Action dated Apr. 15, 2010 for U.S. Appl. No. 11/200,710.
Non-final Office Action dated Jun. 18, 2010 for U.S. Appl. No. 11/573,537.
ISA, International Search Report dated Aug. 31, 2004 for application No. PCT/US03/36411.
EPO, Supplementary Partial European Search Report for Application No. 03789763.4 dated Jul. 26, 2006.
EPO, Supplementary European Search Report for Application No. 03789763.4 dated Jul. 26, 2006.
ISA, International Search Report dated Apr. 10, 2006 for Application No. PCT/US05/028342.
ISA, International Search Report for Application PCT /US00/29223 dated Dec. 26, 2000.
EPO, Supplementary Partial European Search Report for application No. 02761201.9 dated Jul. 3, 2006
EPO, Supplementary European Search Report for application No. 02761201 dated Oct. 13, 2006.
EPO, European Search Report dated Feb. 8, 2010 for application No. 09015376.8.

ISA, International Search Report dated Oct. 22, 2003 for Application No. PCT/US03/15493.
ISA, International Search Report for dated Jul. 28, 2008 Application PCT/US08/058072.
ISA, International Search Report dated Apr. 21, 2008 for Application No. PCT/US07/68401.
ISA,Communication Relating to the Results of the Partial International Search PCT/US07/68401 dated Jan. 30, 2008.
ISA, International Search Report dated Mar. 13, 2008 for Application PCT/US07/68403.
ISA, International Search Report dated Mar. 13, 2008 for Application PCT/US07/68404.
ISA, International Search Report dated Apr. 24, 2008 for Application PCT/US07/68410.
ISA, International Search Report dated Apr. 24, 2008 for Application PCT/US07/68412.
ISA, International Search Report dated Apr. 25, 2008 for Application PCT/US07/68415.
Hungarian Patent Office, Written Opinion to International Property Office of Singapore dated Oct. 22, 2010.
EPO, European Search Report dated May 3, 2011 for application No. 10180483.9.
Ostrander et al., "Dog (Clone: CXX.371) Primer for STS 371, 5' End, Sequence Tagged Site," EMBL XP002392182, Sep. 18, 1993.
Ostrander et al., "Dog Primer for STS 610, 3' End, Sequence Tagged Site," EMBL XP002392183, Jan. 6, 1994.
Bayarsaihan et al., "Single-strand-DNA-binding factors specifically recognize the pyrimidine element in the chick a2(I) collagen gene promoter" Biochem J. (1996) 314:293-296.
Bennett et al., "Inhibition of endothelial cell adhesion molecule expression with antisense oligonucleotides." Journal of Immunology (1994) 152(7):3530-3540.
Bonow, "Primary Prevention of Cardiovascular Disease: A Call to Action" Circulation (2002) 106:3140-3141.
Campos et al., "Distinct patterns of lipoproteins with apoB defines by presence of apoE or apoC-III in hypercholesterolemia and hypertriglyceridemia" J. Lipid Res. (2001) 42:1239-13491.
Chan et al., "Apolipoprotein B-100 kinetics in visceral obesity: Associations with plasma apolipoprotein C-III concentration," Metabolism Clin. And Experimental (2002) 51(8):1041-1046.
Crooke, "Progress in Antisense Technology" Ann. Rev. Med. (2004) 55:61-95.
Cuchel et al., "Inhibition of Microsomal Triglyceride Transfer Protein in Familial Hypercholesterolemia" New England Journal of Medicine (2007) 356:148-156.
Dammerman et al., "An apolipoprotein CIII haplotype protective against hypertriglyceridemia is specified by promoter and 3' untranslated region polymorphisms" Proc. Natl. Acad. Sci. U. S. A., (3993) 90:4562-4566.
Davis et al., "Atherosclerosis Is a Liver Disease of the Heart" Arteriscler. Thromb. Vasc. Biol. (2001) 21:887-898.
De Silva et al., "Overexpression of human apolipoprotein C-III in transgenic mice results in an accumulation of apolipoprotein B48 remnants that is corrected by excess apolipoprotein E" J. Biol. Chem. (1994) 269:2324-2335.
Deere et al., "Antisense Phosphorodiamidate Morpholino Oligomer Length and Target Position Effects on Gene-Specific Inhibition in *Escherichia coli*" Antimicrobial Agents and Chemotherapy (2005) 49:249-255.
Dixon et al., "Regulation of hepatic secretion of apolipoprotein B-containing lipoproteins: Information obtained from cultured liver cells" J. Lipid Res. (1993) 34:167-179.
Duivenvoorden et al., "Apolipoprotein C3 Deficiency Results in Diet-Inudced Obesity and Aggravated Insulin Resistance in Mice" Diabetes (2005) 54:664-671.
Flaim et al., "A Phase 1 Study in Healthy Volunteers to Evaluate the Pharmokinetics, Safety, and Tolerability of Mipomersen in Three Dosing Regimens" Poster Presentation (2011).
Funatsu et al., "Reduction in hepatic non-esterified fatty acid concentration after long-term treatment with atorvastatin lowers hepatic triglyceride synthesis and its secretion in sucrose-fed rats" Biochimica et Biophysica Acta (2002) 1580:161-170.

(56) References Cited

OTHER PUBLICATIONS

Gautschi et al., "Activity of a Novel bcl-2/bcl-xL-Bispecifc Antisense Oligonucleotide Against Tumors of Diverse Histologic Origins" J. Natl Cancer Inst (2001) 93:463-471.
Gewirtz et al., "Facilitating oligonucleotide delivery: Helping antisense deliver on its promise" PNAS USA (1996) 93:3161-3163.
Hertz et al., "Mode of action of peroxisome proliferators as hypolipidemic drugs. Suppression of apolipoprotein C-III" J. Biol. Chem. (1995) 270:13470-13475.
Heymsfield, "Effects of Weight Loss With Orlistat on Glucose Tolerance and Progression to Type 2 Diabetes in Obese Adults" Archives of Internal Medicine (2000) 160:1321-1326.
Isa, International Search Report dated May 25, 2010 for Application PCT/US10/27541.
"Isis 301012" retrieved from the intenet: URL:http://integrity.thomson-pharma.com/integrity/xmlxs/pk_ref_list.xml_show_ficha_ref?p_refid=1132978 [retrieved Nov. 29, 2012].
Ito et al., "Hypertriglyceridemia as a result of human apo CIII gene expression in transgenic mice" Science (1990) 249:790-793.
Jong et al., "Role of ApoCs in Lipoprotein Metabolism—Functional Differences Between ApoC1, ApoC2, and ApoC3" Arterioscler. Thromb. Vasc. Biol. (1999) 19:472-484.
Jover et al., "Cytochrome P450 regulation by hepatocyte nuclear factor 4 in human hepatocytes: a study using adenovirus-mediated antisense targeting" Hepatology (2001) 33(3):668-675.
Karathanasis, "Apolipoprotein multigene family: tandem organization of human apolipoprotein AI, CIII, and AIV genes" Proc. Natl. Acad. Sci. U. S. A. (1985) 82:6374-6378.
Kardassis et al., "Direct physical interactions between HNF-4 and Sp1 mediate synergistic transactivation of the apolipoprotein CIII promoter" Biochemistry (2002) 41:1217-1228.
Kardassis et al., "SMAD proteins transactivate the human ApoCIII promoter by interacting physically and functionally with hepatocyte nuclear factor 4" J. Biol. Chem. (2000) 275:41405-41414.
Kawakami et al., Apolipoprotein CIII in Apolipoprotein B Lipoproteins Enhances the Adhesion of Human Monocytic Cells to Endothelial Cells, Circulation (2006) 113:691-700.
Klein et al., "P284: Apoprotein C-III (ApoCIII) Protein Concentrations and Gene Polymorphisms in Type 1 Diabetes" Aretioscler. Thromb. Vasc. Biol. (2002) 22(5):A-50.
Knopp, "Drug Treatment of Lipid Disorders" New Engl J. Med (1999) 341:498-511.
Lai et al., "Association between obesity and hyperlipidemia among children." Yale Journal of Biology and Medicine (2001) 74:205-210.
Lee et al., "LDL Containing Apolipoprotein CIII Is an Independent Risk Factor for Coronary Events in Diabetic patients" Arteriosclerosis, Thrombosis, and Vascular Biology (2003) 23:853-858.
Levy-Wilson et al., "Isolation and DNA sequence of full-length cDNA for human preapolipoprotein CIII" DNA (1984) 3:359-364.
Li et al., "Common genetic variation in the promoter of the human apo CII gene abolishes regulation by insulin and may contribute to hypertriglyceridemia" J. Clin. Invest. (1995) 96:2601-2605.
Maeda et al., "Molecular cloning of a human apo-C-III variant: Thr 74—Ala74 mutation prevents O-glycosylation" J. Lipid Res. (1987) 28:1405-1409.
Maeda et al., "Targeted disruption of the apolipoprotein C-III gene in mice results in hypotriglyceridemia and protection from postprandial hypertriglyceridemia" J. Biol. Chem. (1994) 269:23610-23616.
Merki et al., "A second generation antisense oligonucleotide directed to human apolipoprotein B-100 reduces lipoprotein(a) levels and oxidized phospholipids on apolipoprotein B-100 particles in lipoprotein(a)-transgenic mice," J. Amer. Coll. Cardiol. (2008) 51(1) Suppl. 1, A294.
Merki et al., "Antisense oligonucleotide directed to human apolipoprotein B-100 reduces lipoprotein(a) levels and oxidized phospholipids on apolipoprotein B-100 particles in lipoprotein(a)-transgenic mice, " Circulation (2008) 118:743-753.
Nielsen, "Systemic Delivery: the Last Hurdle?" Gene Therapy (2005) 12:956-957.
Ogami et al., "Purification and characterization of a heat stable nuclear factor (CIIIB1 involved in the regulation of the human ApoC-III gene" J. Biol. Chem. (1991) 266:9640-9646.
Olivieri et al., "ApoC-III polymorphisms and risk of coronary artery disease" J. Lipid Res. (2002) 43: 1450-1457.
Olivieri et al., "Apolipoprotein C-III, n-3 Polyunsaturated Fatty Acids, and "Insulin Resistant" T-455C APOC3 Gene Polymorphisms in Heart Disease Patients: Exapmle of Gene-Diet Interaction" Clin. Chem. (2005) 51(2):360-367.
Opalinska et al., "Nucleic-Acid Therapeutics: Basic Principles and Recent Applications" Nature Rev. Drug Discov. (2002) 1:503-514.
Pittner et al., "Effects of PYY[3-36] in rodent models of diabetes and obesity" Int. J. Obes. Relat. Metab. Disord. (2004) 28:963-971.
PR Newswire, "Second generation antisense drug for cardiovascular disease demonstrates significant durable reductions in cholesterol" New York, Aug. 11, 2004; Source: Isis Pharmaceuticals.
Protter et al., "Isolation and sequence analysis of the human apolipoprotein CIII gene and the intergenic region between the apo AI and apo ACIII genes" DNA (1984) 3:449-456.
Qidong, Tang et al., "The Inhibition of Antisense Oligodeoxynucleotides on the Expression of Apolipoprotein B in Rat Liver Cells," Zhongguo Dongmai Yinghua ZaZhi Bianjibu (Chinese Journal of Arteriosclerosis) (1999) 7:315-318.
Raspe et al., "Identification of Rev-erbalpha as a physiological repressor of apoC-III gene transcription" J. Lipid Res. (2002) 43:2172-2179.
Reynolds et al., "Rational siRNA design for RNA interference" Nature Biotechnology (2004) 22(3):326-330.
Roglans et al., "Atorvastatin Treatment Induced Peroxisome Proliferator-Activated Receptor Alpha Expression and Decreased Plasma Nonesterified Fatty Acids and Liver Triglyceride in Fructose-Fed Rats" Journal of Pharmacology and Experimental Therapeutics (2002) 302:232-239.
Sanghvi et al., "Heterocyclic Base Modifications in Nucleic Acids and Their Applications in Antisense Oligonucleotides" Antisense Research and Applications (1993) pp. 273-288.
Schoonjans et al., "3-Hydroxy-3-methylglutaryl CoA reductase inhibitors reduce serum triglyceride levels through modulation of apolipoprotein C-III and lipoprotein lipase" FEBS Lett. (1999) 452:160-164.
Shachter, "Apolipoproteins C-I and C-III as important modulators of lipoprotein metabolism" Curr. Opin. Lipidol. (2001) 12:297-304.
Sharpe et al., "Human apolipoproteins AI, AII, CII and CIII cDNA sequences and mRNA abundance" Nucleic Acids Res. (1984) 12:3917-3932.
Tamm et al., "Antisense therapy in oncology: new hope for an old idea?" The Lancet (2001) 358:489-497.
Ugawa et al., "YM-53601, a novel squalene synthase inhibitor, suppresses lipgenic biosynthesis and lipid secretion in rodents" British Journal of Pharmacology (2003) 139:140-146.
Vu-Dac et al., "Retinoids increase human apo C-III expression at the transcriptional level via the retinoid X receptor. Contribution to the hypertriglyceridemic action of retinoids." J. Clin. Invest. (1998) 102:625-632.
Woolf et al., "Specificity of antisense oligonucleotides in vivo" PNAS (1992) 89:7305-7309.
Yamamoto et al., "Overexpression of PACAP in Transgenic Mouse Pancreatic B-Cells Enhances Insulin Secretion and Ameliorates Streptozotocin-induced Diabetes" Diabetes (2003) 52:1155-1162.

SEQUENCE LISTING

<160> NUMBER OF SEQ ID NOS: 23

<210> SEQ ID NO 1
<211> LENGTH: 43445
<212> TYPE: DNA
<213> ORGANISM: Artificial Sequence
<220> FEATURE:
<223> OTHER INFORMATION: Antisense Oligonucleotide

<400> SEQUENCE: 1

| | | | | | |
|---|---|---|---|---|---|
| accaagacag | cgctcaggac | tggttctcct | cgtggctccc | aattcagtcc | aggagaagca | 60 |
| gagattttgt | ccccatggtg | ggtcatctga | agaaggcacc | cctggtcagg | gcaggcttct | 120 |
| cagaccctga | ggcgctggcc | atggcccac | tgagacacag | gaagggccgc | gccagagcac | 180 |
| tgaagacgct | tggggaaggg | aacccacctg | ggacccagcc | cctggtggct | gcggctgcat | 240 |
| cccaggtggg | cccctcccc | gaggctcttc | aaggctcaaa | gagaagccag | tgtagaaaag | 300 |
| caaacaggtc | aggcccggga | ggcgcccttt | ggaccttttg | caatcctggc | gctcttgcag | 360 |
| cctgggcttc | ctataaatgg | ggtgcgggcg | ccggccgcgc | attcccaccg | ggacctgcgg | 420 |
| ggctgagtgc | ccttctcggt | tgctgccgct | gaggagcccg | cccagccagc | cagggccgcg | 480 |
| aggccgaggc | caggccgcag | cccaggagcc | gccccaccgc | agctggcgat | ggacccgccg | 540 |
| aggcccgcgc | tgctggcgct | gctggcgctg | cctgcgctgc | tgctgctgct | gctggcgggc | 600 |
| gccagggccg | gtgagtgcgc | ggccgctctg | cgggcgcaga | gggagcggga | gggagccggc | 660 |
| ggcacgaggt | tggccgggc | agcctgggcc | taggccagag | ggagggcagc | cacagggtcc | 720 |
| agggcgagtg | gggggattgg | accagctggc | ggcccctgca | ggctcaggat | gggggcgcg | 780 |
| ggatggaggg | gctgaggagg | gggtctccgg | agcctgcctc | cctcctgaaa | ggtgaaacct | 840 |
| gtgccggtgg | tccccctgtc | gggccctagc | acccgctggg | aagacgtggg | aagctcacag | 900 |
| atttctttct | cctgtcttac | agaagaggaa | atgctggaaa | atgtcagcct | ggtctgtcca | 960 |
| agtaaggcat | ctgcgcatgg | ggcgtggaag | ggcgcccagc | cccgtgcact | ctcctacacc | 1020 |
| cgggtccctg | agggcctccc | actctacagg | gctgagatgg | catcgtggtg | tgccttgctc | 1080 |
| tgaccccagg | aagcaagttc | cctgagcctc | tgcccacacc | caagggatgc | caactctctt | 1140 |
| ctacctggcc | ttctgttctg | tcccaaaagt | tcagcctggg | ggcgggggag | ggaagggatt | 1200 |
| gtctctccgc | tggcctgtgc | acactttgaa | gaaacatcac | tgtcctgttt | atcagtgact | 1260 |
| agtcattgat | tcgaagcatg | tgagggtgag | gaaatactga | cttttaacctt | tgtgaagaaa | 1320 |
| tcgaacctcc | accccttcc | tatttacctg | accctgggg | gttaaaggaa | ctggcctcca | 1380 |
| agcgcgaccc | tgtgtgctgg | agccgcgggg | cggacttctg | atggggcagc | accgccatct | 1440 |
| agtggccgtc | tgtcatcact | gcagctggac | tcaggaccca | gatgttcttt | ttcttcaatt | 1500 |
| gttcagaaaa | ttcctctcaa | ctacagtgga | aacctccaga | aattcttttc | taggagtttg | 1560 |
| ttaagttagt | tacgcttaat | gcttaatgaa | ctttgcctta | agtatttggt | agtcttagag | 1620 |
| tcacggaatt | acggcgtgtt | caagctaaaa | aagcattaga | gatagtacta | tttgcgtaat | 1680 |
| gttgtcatct | cttaatttgc | cagagggtct | ctcatgcaga | ttttctgagc | cccattactt | 1740 |
| gacacttgtc | actcccttcc | ctgtgcctca | gatgagatat | tcaagacatg | ccagccaatt | 1800 |
| taaacattag | cctcagcaaa | aacataatgg | agaagtcaaa | tctataaagg | aaaattaagt | 1860 |
| ataaagtcaa | ttaaaaaata | atttgagttg | aattaccatt | tttaattctc | tatgccactg | 1920 |
| cccctctctg | cccagaattg | gctgtccttg | ggagagctat | ttctgctatg | tggctgacgt | 1980 |
| atttctcccc | acgttagaag | atgcgacccg | attcaagcac | ctccggaagt | acacatacaa | 2040 |

```
ctatgaggct gagagttcca gtggagtccc tgggactgct gattcaagaa gtgccaccag    2100
gatcaactgc aaggtatgga ggatgcaggc aggagggacc tagagcccac agctttcccc    2160
cagccctgtt ccagcgggcg cccaacacgc gaccttcccg gagggtgtgt actgagcaaa    2220
cgcagaacat cccagaactg ttgtaatctg atcaaagcac tgggactttg cctctgtttg    2280
taagtcagcc acattgctga gatgtggtct gcccccacca aatttcgcaa gtcagaagta    2340
ttttcccgtt aacttcccag atgcaatagg aatccatgat ctagattagc agcagtgtgg    2400
gtctgtagat ttcagcgtga gagaggccca gtaggtgagc tatgggaggc aggcaactcg    2460
gaatcgcact gtgaaatgca gttttttataa tttaagtcaa acagaatctg ttgctgaaaa    2520
atgaatggaa agaagaaaaa aatataaaca tacagtttgt tctaaaataa aactttgctt    2580
attattgaga ctggttgtac tcatgttaca tacatgtgga gcagatctac aggctgctat    2640
tggggtttgg gtgggaaga aagtcaagc tgagcagtca ccttttttta gagagtaccg    2700
tagctcttgt atgtgctgtc caatatggta gacatgagcc acattgggct atttaaatgg    2760
aatgaaatta aaaattcata ttcgttgtca cattagctgc atttcaactg ctcaacagcc    2820
accctggcta ctggctccca tattgaacag cacacatgta caacatttct ataaagttat    2880
ttgaatagtg ctggataata agtaggaatc cgttgaaact ccagctatat gcaaagctct    2940
aaataggccc taatagatat aaccagtttt tgggtgaca ttaaggagac atttgctgtg    3000
gaaacgaagg atggccctct tcctgctttc tgttttttctt cttcacttc actcctagtc    3060 tgcagcgctt ctatttaacc acagctcttt ataattaaag tgagtaactt tagaaccaat    3120
aaaaggacat cctccttccc atgcctaggg gcaaacttaa gaaatgtgtt acccgggagg    3180
gggaaaacgt cagcaatagg actaagtcta ggttggtgca cagagaaccc aggaggcatg    3240
ttgataaggc atgtggtgtt gaggcgcagg cagtggtgtt cccagcacca ttccctttgg    3300
tgctctgatt agagattaag ccctgggctt caggggccac ctctcattct tgatagacaa    3360
cctcaatgct ctgctaccct gaattctcag gttgagctgg aggttcccca gctctgcagc    3420
ttcatcctga agaccagcca gtgcaccctg aaagaggtgt atggcttcaa ccctgagggc    3480
aaagccttgc tgaagaaaac caagaactct gaggagtttg ctgcagccat gtccaggtaa    3540
gtcatgttgt acatgagcac acgcatgtgt gtgtgtccgc tgaggtatga acttgtgtgt    3600
ttgcaccagg cacggatgtg actgtaagta tttgtattcc gtatccatcg tggatcaggg    3660
aattactgag ttttcacaat catcaaaaag agagaagcat tagttaacct tccctagtta    3720
ggttccttta attatcattt tcatgtgttt ctaaaaatct catgctttaa acttcttgag    3780
attataaaac tgagatgctt tgtttaaaca agtgaattct tatttaaaga actagtcaag    3840
actagtgctt ggtggtcttt ggtgtggggt cccagaggca ctggctgctg tggccggcac    3900 atggcgggc agggtctgtt caccgcaggg cagaggagca ccaaggcttc ggtggctccc    3960
cctcctaggc tggcattcag ccactgcacg ctgatcggcc actgcagctg catctctgct    4020
gactggtcag ggcccatgtc gcacccattg taaatatttt caacatcacc cctgcctcat    4080
cctcaatcac agtttgtagg gtcctaggtg tgtatgaata caggcaggat agagttgtta    4140
acttggtagc atcagaaaac tctgtctgta ttagtctgtt ttcatgctgc tgataaagac    4200
atacctgaga ctgggcaatt tacaaaagaa aggtttattg gactcacagt tccacgtggc    4260
tggggaggtc tcacaatcat ggcggaaggt gagggacagc aagtcacatc ttatgtgat    4320 ggtggctggc aaagagagct tgtgcagaga aactcctgtt tttagaacca tcagatctcc    4380
```

-continued

```
cgacacccat ctgcaatcac gagaacagca cgggaaagac ctgcccccat gattcaatca    4440 cctcccccccg ggtccctccc acaacacgtg ggaattatga gagctacgag acgaaatttg    4500
ggtggggacg cagagccaaa ccatatcacc atccttgccc attttttcagt tttgctaaac    4560 attagattca gatgccagtc cttcttgcc aaaataggct gtgaggcttc tttcttcct      4620 atgctttatt ttctccaaga cttaactgta tatgagggag aggggtatgg tggcaggagg    4680
aaagagtggt ttattttttg gtccttggtc ttctccaaat acagaagaga ctcctgttct    4740
tgaaaaggag ggctttccat gtttgcatct tcatgacttt aactgtcttt tttaaaaatt    4800
gacatacaat aattatacat atttattgag aacatagtga tattttgata catgtaatgt    4860
atggtgatca gatcagagta attagcatac ccatcatctc aaacatttat catttcttcg    4920
tgttgggaac tttctgagag agtgtaggct gtgggagata agtccgtcac cttttcctcc    4980
tgatgtaacc agagtggctg cagccaggtc ctcagaaact cagagagtac ccagtgggaa    5040
atccctaaga ccaaagtcag catgggcttc agccatggcc tgacaccata caaaagaatg    5100
actgtccaac aagtgtatga aaataagctc caattcactg gtagtcaaga aatgcgaatt    5160
aatgtaacaa caagatattt atctgctttt acccatcata ctgcaaaact ggaaaacagt    5220
gatagcacct gttgctggca ggccagtgag gaaaagtgtg ctgtcctgag ctgctggtgg    5280
aaacgagagc catcaggcaa tatctactgt aatttaaaat acttaatacc ctttgacaca    5340
gatattttag tctttgggac tctagcccat gaaaataaaa gcagtaatgt gtgaagatag    5400
gcacataagg atgtttgttt tggtattgtt tgtgtggttt aaaaaaaatc cagaaagaga    5460
gagggcaaat gccatcaaat ggggcaatgt gtgaataaat tatatttagc catggaatgg    5520
aatgttctgc atgcagcttt taaaaaaatc tgttagagct gtaccaagtg actcagaagg    5580 attttttgtga agtataatta agtgagaaaa acaagataaa agtatgcata atacaatgcc    5640
acttgtataa aacaaacaat ggcaaaatct ttgtatgact ctgtttgcac tcacccatgt    5700
ttacagagga ttgtatgagt gtgcagaaac aaatggaaca accactcggg tgtccgtatg    5760
gggaggatgg gcaaagagac tgatatgggt ggagaacaga gcagggctgg atgagccaag    5820
caaaaaaagt taaaacacag ctggacctgg tggctcatgc ctgtagtccc agcactttgg    5880
gaggccgagg agggagaatc acctgaggtc aggagtttga gaccagcctg gccaacatgg    5940
tgaaaactgt ctctactaaa aatacaaaaa ttagctgggt gtgatggcac atgccagtag    6000
tcctagctac tccggaggct gaggcaggag aatcacttga tcccaggagg tggaggttgc    6060
agtgagctga ggttgcgcca ttgcactcca gcccgggcga ccgagcgaga ctccatttca    6120
aaaaaagaaa aagaaaaaag aaaaaaagaa aaaaaagaa tcaccaaaac ttatgtatat    6180
gtgcatactt ttttgaaaat gtatgtctat gtgtagctat attctatatt tacaaataaa    6240
tgatgtcaga agaacaattg gttaaaaaaa tatgagaaaa gaaacttcag tgccacccag    6300
cttacttcca gcaagttgta atggagaagg acatttccgt gaccatcctc tctctgggac    6360
aggtatgagc tcaagctggc cattccagaa gggaagcagg ttttccttta cccggagaaa    6420
gatgaaccta cttacatcct gaacatcaag aggggcatca tttctgccct cctggttccc    6480
ccagagacag aagaagccaa gcaagtgttg tttctggtga ggatttagaa agctgatagc    6540
agtggccctt gaaactcatc ttcatgtgtt agagaccagt cctaccatat acaaagcaga    6600
tcactgagtc agctccatga ctagttacat aggaagccct ggattggcgt gaaatactgg    6660
tgcccgaggt tcctcctgcc ccttaggctc actgacagat catcccaagc aggcttatca    6720
ggttgggtct aattttaaaa cagtcattga ggagtcctgg ccacccaccc cctgctttg    6780
```

```
tttgatgctt cacctgtgtt tgctgggtta tggtgtacac agtaaatcct gtgtgtattt    6840
taaacaccaa aaataatggg atctgttgct ggtctctttt acgaatttca ggtttcactg    6900
tgagacagaa ttcatttcac ctcagtccca tgagcacttt tgtgtgttct aatttctcta    6960
cgacaccata atgggagaag acaccgatgc aacctgcgga ggcctttctg cagacccacc    7020
tttaactggt tttctctctc ccaacttggg ctggccaggc actagcaaga ccacactctg    7080
cataggaaga aaaagaaagt ccctcccaaa gctagattcc ttctgctttt tctttcacga    7140
tccccacccc atccctccca agtacccaag gatgttgccc gtgttgaata catgtggttg    7200
catcttcttc ctccatagga taccgtgtat ggaaactgct ccactcactt taccgtcaag    7260
acgaggaagg gcaatgtggc aacagaaata tccactgaaa gagacctggg gcagtgtgat    7320
cgcttcaagc ccatccgcac aggcatcagc ccacttgctc tcatcaaagg catggtaagt    7380
cccatgtcag cactgtcgtg cacagcaagg agcatcctct tattaataca attccagaac    7440
ttttgagcta gtgggcacct ttgaggacag cctgccctgg ctgttttta tacagactag    7500
agataggacc ctgagcaggc acgggaaggt ctgcccaggc ttcacggcct gggatcagtt    7560
gagccaaggc ttgagtcagg ctcctccctc ccagcccaga gctctgtctt tcctcctgtc    7620
cttctgtcac tggcaccaaa ctgcctctaa tctcatcact tgagagtaat gactactcac    7680
ctctgagaag gttccgggga tggatgtagg gcagcaaaac caccttctgt tcttttctgc    7740
acaaggactc cttgtgccag ctccaagcct ctggcctttg aagaagtccc aagacctgtg    7800
ttctcccccct ctccctcatc ccatgaagtg gagtgactta gagtgctcca gcttcttgtc    7860
cttccacccc cagtaccacc ctgaccaaac atggcccac tgccaccggc ctggagcacc    7920
ctctcctctc tgttaactgg ggccatggag caccatatta cctgagcctg cctgacccct    7980
gcaacatctt ccctgatatg agcccagcc tgtctcagtg aacatgaata acttgggcaa    8040
tcactgtcat gctgggcgct gttcctggtc attgtcctta gggttgaaaa cagggagtct    8100
gatgaccatg agtgccacag tcagaagagg ataatgcact ggcttagggg tcttttctga    8160
gcatctgctg tttgctcaac cccactctgg gcagcaccaa ggaagggaca gtggcagatg    8220
aaccatggac cttcccctca ggatgcttcc agtctaatgc aggagccagg tcaataaagt    8280
atacgtggta tactcaataa ggtgataagc tgaacagtgc agacaagaag tcctgggcct    8340
gaccaggaag gagaaagaat tattcatgta gctcagcggg caacatttca tggaagatgt    8400
ggagcaggaa cccaaaaaat gcaaagaata tgtaaatgaa agagacatgt aagaatgggc    8460
ttttgggcaa agaaaagtta ctgagcaggt gtgtgagggg ctatgtggtg ggatgggcat    8520
gtggaggata caaagtttag acattgtcca gtgagggtgg aaaaagagga gtctacagct    8580
tgactcagct ttggggatgc cgacttgttg caccccctgg tctaaatgtc aagtacccag    8640
ttatcttctt tctctgagtt tatctagtgg tacaggactc ctgctcccett ctaccttgaa    8700
ggtaaatgct tttaacagaa gatacaggga ctgatcaaaa tgctcgtctc caatctcttt    8760
catagacccg ccccttgtca actctgatca gcagcagcca gtcctgtcag tacacactgg    8820
acgctaagag gaagcatgtg gcagaagcca tctgcaagga gcaacacctc ttcctgcctt    8880
tctcctacaa gtaggtcatg tgatgcaccc ctgatttgtc atttaatggg tcagtgtgaa    8940
ctgaacactt tcaagtgct ctgttccagg caaacctgtg cctgggaggg aggaatggag    9000
agggataaaa tgccgcccct ccctgtcccc ctttttaagc gaacaggcca tttggcagaa    9060
aagtcctagg catgcaaaac aatccaagac caacaaaaga tatctaagac ccattcttta    9120
```

-continued

```
agggctgtag atccagaaaa cctgaggatc actgcagggt accctggtta gaaaaggttt   9180
catgaaagat ttgggatact gactggaaac ttgtgtatcc aaatccactt tgaaaactga   9240
taatcaatga atatatattg agtaactgcc atattcttgg ctctatgttg tggaagatac   9300
gaaagaattt tgagacattg cactagttcc tacctctggc cactccagac tagtggagag   9360
tataaggcac gcatgtcttt ttgatgggag gataactagc gtgaccagga agaggtggat   9420
gttattcatt cagggccaac aatggctgga tttacccatg ctttgaaaga tgggcaggac   9480
ttgggtagat gcagagacag ggaaaacctt caacatggaa agaatagtat gttctggcca   9540
tccgtgacat ggtgtgcttc cttggttacc aggaataagt atgggatggt agcacaagtg   9600
acacagactt tgaaacttga agacacacca aagatcaaca gccgcttctt tggtgaaggt   9660
aagagtttct gtccacatag ttgctggaaa atctactcaa gatgtgccta tcatggctta   9720
gccacttgct gagccctgtt aaatgtctgc tgactaacaa gtgatacaga cactggtgtt   9780
ctggctacct ctagtgagaa agcaaactca tttcatgatg tcaagttgca atggcataaa   9840
ggaaaagaag ttcccaaagc tacttaggca tttgtaaata gaaaactgga atcctaagtt   9900
taacatgaca tatttgatag aactgacatc acccatcctg tgataagatc cagagctgtc   9960
ccagacgagg tggaccaagt gggagagaac cttcagagtc tggccagata gtaacctcag  10020
gagtcagtct ttagaggtag aaggaactct aacaatctca agtccaaccc ttacccagta  10080
ttgtattgta tttatatctg tccaaattcc ttcttgtaca ttacctcatt gtcctttttg  10140
ctcatagcaa cctgtgatgt caggtggtag agatgtgatt ttatacctat tctacagagg  10200
agacagtgac acagagaggc ttagagtttg atgtagtcaa ggccgcagaa tattagaggg  10260
gggaaaataa gtgccaggtt gtaatctaag ccaggactat tctcattaca ccacatttcc  10320
atgatgactt ttacctctct tcctggcata ggtcacagta ggtggtggag aggatacaaa  10380
agtgtctccc ctccccacaa gctgctggta gacccaatta aagaaatgg tgataagcac  10440 ccatgtgcct ggtcccagtt gtaaccatgt caacagtagc acctcctcac caattatttc  10500
aagctaaggg taacctgatg atagactcag acaagtctgg attccacttt agctctacct  10560 cttagacccct gagagctctt gggaaaccta agttgctcat ctctgggtca cacttcctca  10620
tctctgggtc tcatctcttt gtctcatctc tgggactcag agctgagatc cagggatgag  10680
caatttacat ggcccaaaaa ctctgtgggt ctcagaagca gggctgaatt tatcattaaa  10740
ttgaacaata atgccacccc acagggatag gatgatgagt cagtgaaaac aagtcaatca  10800
cctatggcag agccagatct agcaggcatt gaatacagga tagtttcttt ccctttttccc  10860 ctgtgctgat actccacaat ttccagcttc cagtagacaa agatatggtt gagatgaaga  10920
aagctagagt tcctttgaca ctttccatct tccaggtact aagaagatgg gcctcgcatt  10980
tgagagcacc aaatccacat cacctccaaa gcaggccgaa gctgttttga agactctcca  11040
ggaactgaaa aaactaacca tctctgagca aaatatccag agagctaatc tcttcaataa  11100
gctggttact gagctgagag gcctcagtga tgaagcagtc acatctctct tgccacagct  11160
gattgaggtg tccaggtatc taatggttac agctcaactt tttataaaac tgatggtaac  11220
tgactgaact ttcaaacctt ggccaaatgg agaatctcag ggaccatttg gatatcaatc  11280
cagttaatca attagtcaat cagttcatga ttgctggata gagaactatc agctgctgcg  11340
ctgagttcca tgaaacacac acgcgcatac tgtgttcaag gcagctatgt atttgtgtgt  11400
taaaacagaa ggagaatagt tcccacattt tgatgggtaa ctttttaattc ctaggtctat  11460 tgcaggtgct ctccagaagc ttataggctg gtggagagag aactcagacg aaaaatataa  11520
```

```
tatgatttct ctacccttca aggcactggc tttaagtgct atgaaggtga gagaagggac   11580
tgaggccagg aatgagaccc agctaatgtt ggccaggcat attctgtgtg ctggccaaag   11640
gactgtgata acagtcttct tgttgctaca gatccacagt cccctcttgg aacttttctc   11700 gatgggctt cttctgtggg taatattcct aaggaaagca tcatggttct gagctccaag   11760
ttgggttttg aagttagatt tgaatagtga atgaggtgat taagggctct cctggcagag   11820
gacacaccat gagcaatatt ttatgtgccc tgaaggtggt ctgtataact ttatccatgt   11880
ctttcttctc agccccatca ctttacaagc cttggttcag tgtggacagc ctcagtgctc   11940
cactcacatc ctccagtggc tgaaacgtgt gcatgccaac cccttctga tagatgtggt   12000 cacctacctg gtggccctga tccccgagcc ctcagcacag cagctgcgag agatcttcaa   12060
catggcgagg gatcagcgca gccgagccac cttgtatgcg ctgagccacg cggtcaacaa   12120
gtgagtttcc acactgtatt tctcctccta ggagcagagg aacatcttgc acctctgtgc   12180
atctctgtat taaaactgaa cccctccttc cactttcaaa ctctgctcct tactcttgtg   12240
ttttttcttg atcattttg gggtaatgac ttgaaataag aaatcagcaa acacaaattg   12300 aattttaaa atattttct ctacattata ttataaaagt ttttgaacat agcaaagttg   12360
acagaatttc acagggaaaa cccctagaaa accagctatc tcctactatt taagtgttat   12420
tatatttgct ttatcacata tacatccatc cattaattca tcttatttc tgaagcattt   12480 caaagtaaat tgcaaacatc aacacacttt ccctaagta ttacagcttg catattatta   12540
acttcagttc aatattagtt agcagttttt tcctctgaat ttttttgttt gttttgttttg   12600 ttttttttg ttgttgttgt tttttgaga tggtctcact gtgtcaccca ggctggagtg   12660
cagtgatgca gtcacggctc actgaagcct caaattcctg gctgaagtg atcctcccac   12720 ctcagcctcc tgagtagctg ggaccacagg tgcatgctac catgccctgg ctaattttg   12780 tattcttggt agatacaggg tttcaccatg ttgctcaggc tagcaggttt tccctttgat   12840 gaaattttt ggcttttct tttttacatt tttatataaa tttatgtgga acaagtgtaa   12900
ttttgttaca tgaatagatt gtgcagtagt taagtcaggg ctttcagggt atccatcacc   12960
cagacaacat atagtgtacc cactaagtaa tttctcacca tccatctccc tccacttcca   13020
caccttctga gtctcaattg tctatcattc cacacactat gtccttgtgt gcacattatt   13080
tcactcccac ttataaatga caacacgcaa tatttgtctt tctgtgactg tcctgtttca   13140
cttaagacaa tgacctccag ttccatccat gttgctgcaa atgacatgat tttattcttt   13200
ttatggccga atagtatttt attgcctata catttcacat ttttaatcca atcgtccatt   13260
gatagacact taggttgatt ccatgtcttt gctattgtga atagtgctgt gataaacata   13320
tgggtgcagg tttcctttgg atataatgat ttcttttcct ttaggtatat acccagtaat   13380
gggattgttg gatttattgg tagttctatt tttagttctt tgagaaatct ctgtattgtt   13440
ttccatagtg gttgtactta tttacaatcc catcaacagt gattaactgt ttccttttct   13500
ctgtatcctc accaacaact gttattttt gtcttttgaa taatggccct cctgactctt   13560
gtaagatgtt atctcattgt ggttttaatt tacattctc taatgattag taatgttatg   13620
cattttttca tatgcctatt gccatttgta tgtcttcttt tgaaaaaat gtctattcat   13680 gtcctttgcc tacttttaa tgggattatt tgggggattt ttttgttgag ttgtttgaat   13740
tgcttgtaca ttccggatat tagtacccca ttggatgaat agtttgcaaa tatttctcc   13800 cattctgcag gttaccaccc tgttgattat ttgttttact gtgcagaaac tttttacttt   13860
```

```
aattaagttc tatttgtcta ttttttgttt ttgttgtctt tgcctttgag gtcttattca   13920
cgaattcttt gtctaggcca atgtccagag aagttttccc taggttttct tcttgcattt   13980
ttatagtctc aggtcttata tttaagtctt tgatccatct tgagttgatt ttttttatatg  14040 gtgacagata ggagtccagt tttattcttc tgcatatggc aatccatctt tcccagcacc   14100
acttattgaa aagggtgtcc tttccctagt gtatgttttt gtcaattttg tcaaagatcc   14160
gttgactgta agtatgtgac tttatttctg ggttcagtat tctgttccat tgatctatgt   14220
gtctattttt atgccagtac catgctgttt agattactat agccttgttg tataatctga   14280
agtcaggtaa tgtgatgcct ccagctatgt tcttttttgct taaaattgct tcagctattc  14340
aggctctttt tggattccat atgaatttta taattatttt ttctaattca caagtttggg   14400
ttttaagaca aacctaactg gggttaccaa gtcctgactc tcttctctta ttctgtagct   14460
atcataagac aaaccctaca gggacccagg agctgctgga cattgctaat tacctgatgg   14520
aacagattca agatgactgc actggggatg aagattacac ctatttgatt ctgcgggtaa   14580
tctcagtctt ttatatgaca tacatcattt cagaagcact tttcctggac accttttact   14640
tccctctcct gcaccctgat gggttcttgt ttcttttctt caatgcaggt cattggaaat   14700
atgggccaaa ccatggagca gttaactcca gaactcaagt cttcaatcct gaaatgtgtc   14760
caaagtacaa agccatcact gatgatccag aaagctgcca tccaggctct gcggaaaatg   14820
gagcctaaag acaaggtaaa gtccacaaga agaggtctga aagtgaaagt ttattaacaa   14880
ggatttggaa ggtactaggg gaatgagact ctagatttca tctactgact ttattctgct   14940
gtttctttcc tttccttcct tccttccttc cttccttcct ccctccctcc ctttcttctt   15000
tccttccttc cttccttctt tcgagatgga atctcactct attgcccagg ctggagtgca   15060
gtggcatgat ctcggctcac tgcaacttct gcctcctggg ttcaagcaat tctctctgcc   15120
tcagcctcct gagtaactgg gattacaggc atgtgccatt acacccagct aatttttgta   15180 tttttagta gagatggagt tttgccatgt tggccaggct ggtcttgagc tcctgacctc   15240
aggtgatccg cctgcctcag ccttgcaaag tgctgggatt acaggcgtga gccactgcac   15300
ctggcctcta ctgttttcta attgcaaatt tcaacaagcc tattgacttg actgcctagc   15360
agtatgtgac gtgagagaaa tacttgactt tgctgctatg tcaacatgca gaacgtgaga   15420 tgttttgct tcctaccgtc cacctaccag attgaccatc cctctcatca tggaaaaaca   15480
tgcttaattt tcccccaata agcttaggct aggatagcca acttggcccc ctcttaggtg   15540
caaagactcc agaactttgg aaactaccct atttattagc cccaaactct tactacccct   15600
tctcatcttt atcctcacat taaaataact tacgttaaaa caacttgatt ttcacttagt   15660
ggtggatctc caaacaaatc acaacttggc cataatttat gtgttttaat ggaattgaat   15720
tcaacaggca ttccacaggc ttttttctggg aaccccttact tgatagtgct ctaggaaaca   15780
ctggcaagaa gattcaatac cagcatttga agaacgatta cagagaaatt agacctgtgc   15840
ttaagaaaga gctagcagac aatgccagtg tttgccaggc atgttctgtg ttctgaccac   15900
aggacagtga taaccatctc ctcttttgac tgcaggacca ggaggttctt cttcagactt   15960
tccttgatga tgcttctccg ggagataagc gactggctgc ctatcttatg ttgatgagga   16020
gtccttcaca ggcagatatt aacaaaattg tccaaattct accatgggaa cagaatgagc   16080
aagtgaagaa ctttgtggct tcccatattg ccaatatctt gaactcagaa gaattggata   16140
tccaagagta agtaagagct attcaccca tataccactg agggccctga gctggaattc   16200
caaccctagg ttttggcata gccactgtct gcccttgctt ctgaaacaaa cacttgtgca   16260
```

```
aatgtgtagc agatctagac ccaaagactt agggtcaatg aaatcaagac attttggtag   16320
tgattggaaa tccatattta cttggggtgc aagagtcaaa ggataataac atggtgtgtc   16380
agctcaaaat atacttcttc ttatctagtc tgaaaaagtt agtgaaagaa gctctgaaag   16440
aatctcaact tccaactgtc atggacttca gaaaattctc tcggaactat caactctaca   16500
aatctgtttc tcttccatca cttgacccag cctcagccaa aatagaaggg aatcttatat   16560
ttgatccaaa taactacctt cctaaagaaa gcatgctgaa aactaccctc actgcctttg   16620
gatttgcttc agctgacctc atcgaggtaa gtgtgaagag tttgaggttc tctagcccat   16680
tttgtacagc atcataaaca gagagtccct gggagccagg agctacccag ggaaaaacta   16740
agaaccacca ggcacttcct accatgattc tgaggctttc ttctttccct ccttcccgc    16800 cttcctctct ccccgctagg ggtcacctga agcatgactt cttaacatta atagaaatgc   16860
aggcctggcg aggtggctca ctcctgtaat cccagcactt ggggaggccg aggcgggtgg   16920
atcatgaggt caggatatcg acaccatcct ggctaacacg gtgaaagccc atctctacta   16980
aaaatacaaa aaattagccg ggcgtggtgg caggcacctg tagtcccagc tacttgggag   17040
gatgaggcag gagaatggcg tgaacccagg aggctgagct gcagtgagc cgagagattg     17100 cgccactgcg ctccagcctg ggcgacagag caagactcca tctcaaaaaa aaaaaaaaa   17160 aaaaaaattg aaatgcaaat gtctcgtctt taagtcccaa agccaaggaa gcatatgtgc   17220
tgcctagtca gatctgcttc aaatctcaaa tcactcccaa ctctgaatcc tttgttgaat   17280
tatttgtcct atctgaacct tagctgcctc ttctagaaaa aagcaagtaa taaggtcaag   17340
attctagtga gattttaata aagcagctcc tgtgaaatgc taaggtcagc tcctggcctg   17400
tggtattcaa atacttgttt agataaatgg acatcaagag tggggactac taggctggca   17460
tacaacaaag aaacctgatg ccattttctt gtctgatttt ctttctcaga ttggcttgga   17520
aggaaaaggc tttgagccaa cattggaagc tcttttgggg aagcaaggat tttttcccaga  17580 cagtgtcaac aaagctttgt actgggttaa tggtcaagtt cctgatggtg tctctaaggt   17640
cttagtggac cactttggct ataccaaaga tgataaacat gagcaggtgt gtatttgtga   17700
agtatcttct taaggaaagc tttgggtctc aatgcaaaaa caattctttt ctaagcatgg   17760
aagtcctcaa aatactatct aactgaaggg ataactatgg tttttatcaa ccagacctgc   17820
tggggtaagg gccagtatcc tctgcagtta aagatctcct gaattcagtg tgcccagaaa   17880
ccagactcac aataagtact ctaggataac aagagtatga actctgggct gggtgtggtg   17940
gttcatgcct gtaatcccag cactttggga ggccaaggtg ggcagatcac aaggtcagga   18000
atttgagacc agcctggcca acatactgaa accccgtctc tactaaaaat acaaaaaaac   18060
tagctgggca tggtagtggg tgcctgtaat cctagctact cggaggctg agacaggaga    18120 attgcttgaa cccgggaggt ggaggttgca gtgagccgag atcacgccgt tacactccag   18180
cccgggtgac agtgtgagac tgtatcttaa aaaaaaaaaa agtatgaact ctgggcatag   18240
atttaattct aacttccctg tcttgaagct gtgcgcactt ggggaagttg gttgatatta   18300
tgtgtatctg tttctgtctg tatcccagac tactaataac agtccaaacc tcacaaggtt   18360
atttaaagac aatgaaataa ggcatctaaa atgccaagca cagtgcctga tgctggcatt   18420
ggttgttcaa taagcagaca ctattacgag ttctaaatta atattttcat tattattaac   18480
tgctgtcttt ggctctcact cccatcagtg cactagcaaa tgagaccaaa cttccacttt   18540
gaagctagca atgagccccc atttaaggag ggaaataggt tgtatgatct ggagcttatt   18600
```

```
cttgaatttt ttgctaccca aagtgtggtc tggtcagaaa tacagcttct catgcttcac   18660
ccacaatcta ctgaatcaga agcgcatttt agcaagacct catgtgactt gtatgcacat   18720
tcaactttgc agagcaaggc agtaatttac ccctccaggc tcactgttga gcacgagctc   18780
catcttctaa tttcctgacc cccacttgag gccgaggatc tttgatctgc tttgagtctg   18840
tcagtttcac atttttttt tcccaatgcc tgggcatcca tctctgagat tcttcttctc   18900
tctgagaaga acttgtctag gatcaagtgt ttttcaaact tctggtgaat ttatataaca   18960
gctacatttt cttaagaaac accttgtagt cttcactggt caaagaagag aaggctaagc   19020
agggaacggg tggggatag aggatcttct aatcttgagg atcctggcat actggagaat   19080
agggacccct cctctcatcc caccacatct tactatgtct acagattttt taattaagaa   19140
tagctttagg agtgccacta tccctgacaa gaccttagtt cttaatctc tgcttagagg   19200 aattagcctg gacttcagtg tctccctgtt cctcacctgg agcatttttt aggcccatcc   19260
tggctgcatc agacaggtcc cacattggga actgaaaggt gtttgacatt gctgacatct   19320
cactggccat tttattacta aactctcagg atatggtaaa tggaataatg ctcagtgttg   19380
agaagctgat taaagatttg aaatccaaag aagtcccgga agccagagcc tacctccgca   19440
tcttgggaga ggagcttggt tttgccagtc tccatgacct ccagctcctg ggaaagctgc   19500
ttctgatggg tgcccgcact ctgcagggga tcccccagat ggtaagtcag caggccccac   19560
tgggggccca tgagaccaga cgttggtttt tttttagatc gcccagactc ccttacgatc   19620
ccagctgcac aagcccgaaa agatgcttgt actttcttca gagatggagg tttgccttga   19680
atttcactga agatgactct tggatcacat ggaaatgtta acatttagaa attaagctat   19740
tcataatgtt agctgtattt ttaagagcat taatttattc atctggaaaa caatgttcgg   19800
tataccttcc tctacctttg ctgaaggtcc ttttattttt atttttattt ttttaatttt   19860
ttgagatgga gtcttgctcc caggctggag tgcagtgata caatctcggc tcactgcaac   19920
tctgccttcc gggttcaagc aattctcctg cctcagcctc ccaagtagct gggactgtgg   19980
acgtgcacca gcatgcccgg ctaatttgtg tatctttagt agagacaagc tgttgacaa   20040 ccatgtcagg ctggtttcga actcctgacc tcaagtgatc ctccagcctg ggcctcccac   20100
agtgctggaa taacaggtgt gagccactgc acctgacctg aaggtccttt taagattgaa   20160
atgatacaat gattataaaa gaaagtattt ggcaaactat aattcactat ctaaatatgc   20220 tataatttt attattaatt cataaaagga aatatataaa tgtactccta tggcttgatt   20280
aaaaaaatgt tgactttaag aaaacaggtc tcaagctatt ttattgaaat attatttaaa   20340
aaataaaacc caatgcaaat tgatatgtac atcatctcaa taggcctttg gtttcaaaaa   20400
attgatttta tcataatata atacatttca agtacacctt cacttacagt cagactccag   20460
aacaccagaa ttaagccatg gcatatatga tacttaaagt ccataaagct ctgaggccca   20520
gcaatattct taagagcctt ctgagtccac ttgaaaatga catgtatatct atctagtgaa   20580 atttcttata tcctgattca ctgaaaacgg taaaaacatc agtttgatct ttatttatca   20640
aactattcag ctcatcaaaa tatgctagtc cttcctttcc agataaagag gaattactct   20700
ccaatgtatg ggaggttgta attaacaaaa ccgactttaa aaagacttac ttttatttgc   20760
tctcccttgt tgggtctaca gattggagag gtcatcagga agggctcaaa gaatgacttt   20820
tttcttcact acatcttcat ggagaatgcc tttgaactcc ccactggagc tggattacag   20880
ttgcaaatat cttcatctgg agtcattgct cccggagcca aggctggagt aaaactgaaa   20940
gtagccaacg taagattctg tttgcctttt gatttcttag gttattactt cttccagggg   21000
```

```
tgcatttctt gttaaaacat atttaaaaat gtgtttccac ttcaagacaa aatgcttcat   21060
cattgtaatc acctcattat tttttttatga aaaacttcaa gcttccacca gaatgcacta   21120
cctcactagc tccagtagtg gtatggccat aagacaagaa ctcagttctc tcaacaaatg   21180
agtattccta tcatctttttt aatctggttt tgcctcacgt taactcaggt gctttctagt   21240
tctgggtagt atactccaac tctagagaac tgagaactcg ctttccttct tccaaacaaa   21300
tcccagtaat gtttccaaag gtctgagtta tccaggaaat ctttgcccgg aggtgagaaa   21360
gggtggttga tctgactgac aggggactga agtatttaat gaatctgaat aggttgtttt   21420
ctgacttata gatgcaggct gaactggtgg caaaaccctc cgtgtctgtg gagtttgtga   21480
caaatatggg catcatcatt ccggacttcg ctaggagtgg ggtccagatg aacaccaact   21540
tcttccacga gtcgggtctg gaggctcatg ttgccctaaa agctgggaag ctgaagttta   21600
tcattccttc cccaaagaga ccagtcaagc tgctcagtgg agggtaattc tttcagccaa   21660
gtctgcctag ccagtttgaa agagagaaca gagaatgtac ctgcagaatt ttgccaggct   21720
aaacagttga ttgagatcat tcaggtcctg aggaagcagg agaggagtag aaaggaaaga   21780
ttccgggtta cctatttttaa ttctagccta gacttactac ataactacat aattacctttt   21840 cttctacttt tcacatttta ctaaactgtc ctttatcttt ctgctttgag acttattaag   21900
acctactgct taattagttt ttattaagtt gtgatttttt gttatctatt tgttttgaga   21960
atgaagaaac aatagctctg gagagatcat ctttggaaaa ttaatatttt cccccccaaa   22020
aaatacctaa gaacatattg atttgaggta gctaggtagg taaagcatga aactcctaac   22080
ctcgtgataa tggaatacag cctcttttgg agagttccat tttaagtggc accctcaacc   22140
attgatttgc cttagttttc atattttaga cacattcatg tgttcattca aaaataatat   22200
ttaattggcc agccacggtg gttcatgcct gtaatcctag cactttggga gccccaggtg   22260
gatggatcgc ttgagccctg gtgttttggat accagcctgg gcaacatggc aaaaccccat   22320
ctctacaaaa aaaattaaat aaataacaaa attagccagt cgtggtggca catgcctgta   22380
gctccagcta ctcagaaggc tgagatggga ggatcaactg agcccaagag ttcaagcctt   22440
cagtgaacca tgcttgcacc actgcactcc agcctgggag acagagcaag atcctgtctc   22500 acaaaaaaaca aaaatagta tatttaattg cctaatatat accacgtatg ttgagtgaga   22560
cacacaaggt ccctgacctt tgaacgctta cattttataa gggagacaca caattaagca   22620
agcagtaatc atagagtaag ggctaagtta tagaaagtat tagagtacca tgaaattta   22680 tatcatgtag cctgtgctag tcagggaatg cattctgaag caagtgtact tgacctgata   22740
actgaggact gtgtcagagt catttaggca aaggagaaag gagtgagtgt tccaggcaaa   22800
aggaaaagca tgtaatggcc tgaaggtaaa ggaatatggt tcaaggaact ggaagaagtg   22860
cagaatggta aggggctcag agatgatggg gagaggtagg caggggagag agcatgccca   22920
gctgcgaaag ccatcctaag gagtttggac tcttttgaag gcacaggagt tgaaaagggg   22980
agcagaaata agatagggggt gatgttttag aagaaatact ctgactctag tgtggaagat   23040
gggtgagaag gaggcacagc tggacacgaa gagaccattg gacatctctt acgatccctat   23100 gtggctaaga gctgataatg gcctgcagtg gagaaaagcc aggtatagaa aggagtgagc   23160
agattctaca actttctaag aggcagaatc ataagtactg ggtgattaac tgggtatggg   23220
gacaaggcaa aagaaagaag aaaagaggaa ggaggcgccc ttcattttaa taagaactac   23280
agtgggagag cttctggttt caaggaaagt gacaaattca gttttggatg tgctgtattt   23340
```

```
gatgtcctcc tatgaaacaa ccagtttaga aatctagctg tcaaatagac ctatggatct    23400
gagcccagta aagaggcttg ggctccacat atggatttgg gaatcattag tatacagagg    23460
ttgttgtggt taaacagcaa ctggtataga gtgagacatg agagatgagg acagaaatat    23520
ggagaagaca acatataaaa ggaagaaggg gaataaccag caatgagtta aagaagtga     23580 ccagagaagc agaaggagaa ccaaagccat aaaaggtcac agaagccaaa gagcagccac    23640 agggagatc accccatggg taggcgaaag ctggcattag gactccagca catcagcaaa     23700
gcttggtctt gtggcacccc caacttggag aaacaatact tggaggaaaa tgtgctattt    23760
caaagaaagc atccttagaa aaaccaggc caatgttgaa ctttcttaca tgtactaagt     23820
ttttaagtac acacttggaa ggaaggtgcc atcatctctt cagatgtgag aggctccagc    23880
gtcttagtct ggtcatgagt gcgcaactct atggaaggct tctgggaggt caaggaagat    23940
gaaacctaaa tatgcccatt ggatgtagga gcaaggaggg cattagagac attgatgaaa    24000
gcattttcag gagatggagt gagcagtcag agcacattgg gaggaagtag agactgcaaa    24060
ggcagacaac tcttgatggt gaggaagatg agaaagcaag aaaagaaaga aaggagcata    24120
ggggaggggc acaggggaag agacttgagc gtgcttaatg caggtggaag gaagcaggta    24180
gagagtagga gatttcatat gaaagagaca gtttctcttg ccctgcattg taggaaggaa    24240
ggggcacact gaagttcagc cccagtgatc agctatttaa catctctgag cctctgcttc    24300
tgtaaaatga gaaccataag cctactgttg tggggattac aggtaacaga tggaaagaac    24360
tcagccagaa gcttcagagt cactctcatg gcttgtcatg ttgatgttct ttctaatatt    24420
atttgtttct cagtaaaatta aatagttaga gataggtgtg gactgaggga agacaggagg    24480 ataaggggt attttgcaccc tgagaatttg tgatgtccat tttgattcat gacttggcaa    24540
taactcaggt atttttgttc ttcaccagca acacattaca tttggtctct accaccaaaa    24600
cggaggtgat cccacctctc attgagaaca ggcagtcctg gtcagtttgc aagcaagtct    24660
ttcctggcct gaattactgc acctcaggcg cttactccaa cgccagctcc acagactccg    24720
cctcctacta tccgctgacc ggggacacca ggttagagat gctcagtgcc tgacccagca    24780
ttttctcacc ttccacatca tggccaccta gcatggcaca ggaaaaaata ctctgtgttg    24840
taagaccctg tcactagcct tctgggtttg caccatcttt gggtatttaa agcagggtcc    24900
tctggccaac acattgggtg tcaccttttg cttccttgtg catgggatgg gatcacagca    24960
cagatcccaa tttgctccta attcagtgtc catgtttctg agcctccaga cccatcgcta    25020
tgagcttcct ggagcccacc aatgtgcttg aagccttcac cgtacttagg tggctccctg    25080
tcttcagccc ccaagttcca gtgcttgttc tcagctttgc tgaaacaacc agccaactcc    25140
tgctctgctt gtccaaagtc ttgggaatcc tggtgtctgc ccttgccttg ggttcttgta    25200
ggactgaggg atcaaaaaga tcatcttagt taagggcaag agacaatgtt aaaataagga    25260 ccatatttt gttgcatttg aggctgaatt gttttgggaa cataatcacc atccttgaaa     25320
gctctaacat tatgcactgt cttcattgta atgtctttag attagagctg gaactgaggc    25380
ctacaggaga gattgagcag tattctgtca gcgcaaccta tgagctccag agagaggaca    25440
gagccttggt ggatacctg aagtttgtaa ctcaagcaga aggtgagtat tcaaaacaca     25500
gctgcctcat ctctgctcgc agtctcaggt tcagaattca tgaggagaag acatgtaatt    25560
taacctattt aacaaatagg ttaactgagt acccactaag cggcaggcct attctaagac    25620
ctgggttaac tgagtaccca ataagcggca ggcctattct aagacctggg gctagaacag    25680
tgaacaatgg agtctctgcc ttcatggaag ttacagtgaa caaccaaaca agttaatatt    25740
```

```
tggaatatca gataagtact gaggaggaaa acagagcgta gactggtcta tggagggcta    25800
ggagtaggag ggaggaagaa gggcagggaa agcagtgcat ttggaataat aagggaaagt    25860
ctccctggta aagtgagcat aaggagacct atcagaaata agaggagaag ccgtgtggta    25920
agactgttaa caggcagagg gaccagcaag tgcaaaggcc ctgaggctga cacactacta    25980
ccatgtttca aggaaaggaa ggaagacagt atggctggag cagaaagacc agggagaaaa    26040
gaggtagaag atgaggacag agagatatgg agaggtgaag gaaggataat ctcataggcc    26100
atggtaagaa ctttggcttt ttctatgaat taaacgaaag ccattgggga gtcctcatga    26160
tttgatttat gtttatgttg agaaaagact atgggcagac aagggcagag aaactaatat    26220
gtaggttatc acaataatcc aggcaggaat cagtgttgtt ttggatcagg gcaatggcag    26280
aagagatatg agaaggggat ggattctggc catattttga agattaggct gacaagattt    26340
gctgatacag tggatgttga gtgtaagagg aaaagggaa tgaagacaaa cctaaggttt     26400
ttggcccggg caactgaaaa atggaacttc catttattga gatggaaagg gctactggag    26460
gagcaggttt tagggaatgg gagaaattta ggtgttcact ttggaaaaaa aattatatag    26520
ggatagcgag gagcaggttt tagggaatgg ggcacattta ggtgttcact ttggaaaaat    26580
ttttatatag ggatagcata tcacagaatt aaactaggaa gaaaatccca tgatagaaag    26640
cactggagga gcagggcacg ctggggaaat agtgtttggt aaacattgtt ttacgaagga    26700
tataaaatgg accagcctat ggattgaagg acgcccggga atcttgttac aaagaaaggg    26760
ggagttgggg agatggagcc cagggcaagg gcagcaagga accaggacag gcatcttggg    26820
tagaaagtaa tatagagatg tcgtgtcttc ctggcccaga agggctgcga gcctttgctg    26880
ttccacaaac aagctaagtg ctccccattt cagggccttt gcattcctga ccttctgcct    26940
ggaatgtgct cctcccagaa ctcagcgtgg ctccaacctc ttttcattct ggtctctgcc    27000
cacatgtgcc cttatcagag agaatttctc tgaccaccaa gtatgaaata acacttcttc    27060 tatcccttc ttttatcctt gtatccagtt ttactcttct tcataacatt cattaccatc      27120
tgacatgagc aagttacttg tttattgcct gtacacctcc cccactagaa ggtaagcccc    27180
atgaaagcaa ggattcccca gtaccaagag cagtgcccag cacacaatag gctcataaca    27240
ggcaatccat aaagacttgc atacatgaac acaactgagt ttaaaattat cagtaaatga    27300
gacccattaa aaaattttaa tgagaaaaaa aaaattcagt aaaatcctga actgtgtttt    27360
tgtttaagca cattgattcc ttggagtttc tctaccttt cctctctttc cttccaaaac      27420
atagcttctt tatttattta tttatttatt tgtttgttta tttatttatt tatttattta    27480 tttattttt gagatggagt ctcgctcttt tgcccaggct gcagtgcagt ggtgccatct      27540
cggctcactg caagccccgc ctcccgggtt catgccattc tcctgcctca gcctcctgag    27600
tagctgggac tacaggcacc caccaacgcg cccggctaat ttttgtatt tttagtagag      27660 acggggtttc accatgttag ccagaatggt cttgatctcc tgacctcatg atctgcccgc    27720
cttggcctcc caaagtgctg ggattacagg tgtgagccac cgcacccggc caaaacata     27780 gcttcttacc acacatctct tgattctctt atacactcgt ccaggtgcga agcagactga    27840
ggctaccatg acattcaaat ataatcggca gagtatgacc ttgtccagtg aagtccaaat    27900
tccggatttt gatgttgacc tcggaacaat cctcagagtt aatgatgaat ctactgaggg    27960
caaaacgtct tacagactca ccctggacat tcagaacaag aaaattactg aggtcgccct    28020
catgggccac ctaaggtaaa gaaggccgag ggtcatctga cctgcactgc aggcctgggt    28080
```

| | |
|---|---|
| ggttcttttc attattcctc ttccacttca tacctgacca agccatgttc tcccctagtc | 28140 |
| tacaatcaga gtggcagaga gagccctcaa caatttttt ttttttttgag atggagtctc | 28200 |
| actctgtcac caggctggag tgcagtggca caatctcggc tcactgcaac ctccgcctcc | 28260 |
| cgagttcaag tgattctcct gcttaagcct cccaaggagc tggaactata ggtgcatgcc | 28320 |
| accacaccca gctaattttt atattttag tagagacagg gtttcaccat attgaccagg | 28380 |
| atggtctcga tctcctgacc tcgtgatcca cctgccttgg cctcccaaag tgctgggatt | 28440 |
| acaggtgtaa gccactgcac ccggccaagc tctcaacatt ttaaccctct gcgcatgtcc | 28500 |
| agttggattt tcctaccatt tatcaggcac ttactattca tgtatcaagc acagtgctgg | 28560 |
| gtgctttaaa gaaattatct cggtcctcac aataaactgc gaggtcactg tgagttttcc | 28620 |
| tgtttcatgg ataaggaaat ggtagctcag aggggttaaa tcatttggtc aaaatcacag | 28680 |
| agctagtaaa tagcagagca ggattcaaac agttttcaaa aaacttctct ttctcctaaa | 28740 |
| cctgtttgca aagtccttaa tttgtgctga atgttggctt tagaagttga tgagtttgat | 28800 |
| ctgtggctgt ttctctgaac catccttgta tctggttttg atcaccacaa atggaacttc | 28860 |
| tgtttaatcc tgcatatctc cattgaaagg acaaaatcat tggtgccaac tgattttctt | 28920 |
| taccatagtt gtgacacaaa ggaagaaaga aaaatcaagg gtgttatttc catacccgt | 28980 |
| ttgcaagcag aagccagaag tgagatcctc gcccactggt cgcctgccaa actgcttctc | 29040 |
| caaatggact catctgctac agcttatggc tccacagttt ccaagagggt ggcatggcat | 29100 |
| tatggtatgt gtctcttccc ctgtgtgagc acttccaaag taatgcaggt gttgagacct | 29160 |
| gtggttacag gctgaactag taccattcac aactatttcc tacgtatttt cagatgaaga | 29220 |
| gaagattgaa tttgaatgga acacaggcac caatgtagat accaaaaaaa tgacttccaa | 29280 |
| tttccctgtg gatctctccg attatcctaa gagcttgcat atgtatgcta atagactcct | 29340 |
| ggatcacaga gtccctcaaa cagacatgac tttccggcac gtgggttcca aattaatagt | 29400 |
| tgtaagtatg agtctgccag tcaataaata catggatata agtgctaatt acatcctcaa | 29460 |
| ctctgagcta ggtgcaggaa ggtttccaaa gatgtataag gcatgcttcc ttcccccccag | 29520 |
| ggaattcttg gggagaaaaa aaaactttca caagtgtgta gttacccagt tacacaaagc | 29580 |
| tgaatgtgat acatatcaaa gagatgctac taagtagaac agttctttgc ctagtggtat | 29640 |
| caaaggaagc ttcaggacac cagctaggag gctgactatg ttagacattc cttttataaa | 29700 |
| tatggacagt gatcagtgac tggcaacgaa gattcataat tttctgttat ttattttaa | 29760 |
| ctttcagtgc attgtccagc ttaataatta acttgtcaaa tcggtatttt tgcctaatgt | 29820 |
| tcattgctct ttgaggctca tccaagccca ttaccttaaa aatctcctgt cattttgtag | 29880 |
| gcaatgagct catggcttca gaaggcatct gggagtcttc cttatacccca gactttgcaa | 29940 |
| gaccacctca atagcctgaa ggagttcaac ctccagaaca tgggattgcc agacttccac | 30000 |
| atcccagaaa acctcttctt aaaaaggtaa aagaagaaag cagcaaggct tcttgaacca | 30060 |
| tgcaaagtaa atgaaagatt ttacatagca tgatttagac atttttttaa atttttaaag | 30120 |
| gaaataattt aagcatttta aggagattaa taactatagc acaaacactg tggcatcttt | 30180 |
| gcattagtaa acatgagaac accaaccctg tcaggaagaa tctaagaaag tcattagagg | 30240 |
| attctggtac tttcacccta agatattta ttcagtacaa cctgttataa gcaaattctc | 30300 |
| cctctgactg tgaagaattc agaatggcta gaggcgttat tgactacagg cttgctgtta | 30360 |
| agctagagag agtcagaaca gccattgagc actaaatgga ggcagcattc tgagaaaata | 30420 |
| cttaacccca ggcttactga cttccatacc tatgttcttt ccacaaatca agttgtctca | 30480 |

```
attcagttta gcaaatttgt atcaagtatc ccctatgtgc aaaatgctag actaggtaca    30540
gtgagaagat agaaactggg taaggtatag ccttttcttt caagaagata ccatggagac    30600
atcaacaaat gagaaataat taattatata agcaaaatta tgacatgctc tttgagaaag    30660
gtgcaaggga ctatgtaact gtaagaatga gacaaattgg ctatgactta ggtgggatgg    30720
taatgataag gagtggccct tagaagagct ttgtcaggat ttgagtgttt gacaggtgga    30780
ggtaaaagca aaggggtcca ggcataggag tagcacaaag aaaagtgcag agtggctttg    30840
ggaatggggc aagtacaata ttgttgtgaa ggtcagaggc agagaacttt gaatgactga    30900
tgtctgactg tggggatgtt atctttgttg ttcatttcag cgatggccgg gtcaaatata    30960
ccttgaacaa gaacagtttg aaaattgaga ttcctttgcc ttttggtggc aaatcctcca    31020
gagatctaaa gatgttagag actgttagga caccagccct ccacttcaag tctgtgggat    31080
tccatctgcc atctcgagag ttccaagtcc ctactttac cattcccaag ttgtatcaac     31140
tgcaagtgcc tctcctgggt gttctagacc tctccacgaa tgtctacagc aacttgtaca    31200
actggtccgc ctcctacagt ggtggcaaca ccagcacaga ccatttcagc cttcgggctc    31260
gttaccacat gaaggctgac tctgtggttg acctgctttc ctacaatgtg caaggtgagc    31320
tatgctcagg taaagggtgc accgggctag ttcatggcag gctctaagag gagagcctcc    31380
tccagggagg aaaggacttt ggcttttctag cagataatct tccttgctac ttggaagtct    31440
tttattttat tcaacaaata gaaatattta ttaaacatat cacgtgtatt aaatattcta    31500
gtaggcagta acagaaagta gacagataag ccagcaatta taattcagtg tgagaggtgc    31560
tatgataaag tgtagtatat aagtataagg tagagtggaa gcactcaaca agggaaccta    31620
aacaaagcct gtggtggtca ggcaaggctt cctggaggaa tgccttttgc tatcagattt    31680
tatctttgca ttacagatgg aggagtctat tgcacaattg gcccagaaaa atgggctttt    31740
attattgaaa gactttcaac atagagattg ctctggaaat gtactgctta atttaaccaa    31800
tgtcttttca tttttatgtt aggatctgga gaaacaacat atgaccacaa gaatacgttc    31860
acactatcat atgatgggtc tctacgccac aaatttctag attcgaatat caaattcagt    31920
catgtagaaa aacttggaaa caacccagtc tcaaaaggtt tactaatatt cgatgcatct    31980
agttcctggg gaccacagat gtctgcttca gttcatttgg actccaaaaa gaaacagcat    32040
ttgtttgtca aagaagtcaa gattgatggg cagttcagag tctcttcgtt ctatgctaaa    32100
ggcacatatg gcctgtcttg tcagagggat cctaacactg gccggctcaa tggagagtcc    32160
aacctgaggt ttaactcctc ctacctccaa ggcaccaacc agataacagg aagatatgaa    32220
gatggaaccc tctccctcac ctccacctct gatctgcaaa gtggcatcat taaaaatact    32280
gcttccctaa agtatgagaa ctacgagctg actttaaaat ctgacaccaa tgggaagtat    32340
aagaactttg ccacttctaa caagatggat atgaccttct ctaagcaaaa tgcactgctg    32400
cgttctgaat atcaggctga ttacgagtca ttgaggttct tcagcctgct ttctggatca    32460
ctaaattccc atggtcttga gttaaatgct gacatcttag gcactgacaa aattaatagt    32520
ggtgctcaca aggcgacact aaggattggc caagatggaa tatctaccag tgcaacgacc    32580
aacttgaagt gtagtctcct ggtgctggag aatgagctga atgcagagct tggcctctct    32640
ggggcatcta tgaaattaac aacaaatggc cgcttcaggg aacacaatgc aaaattcagt    32700
ctggatggga aagccgccct cacagagcta tcactgggaa gtgcttatca ggccatgatt    32760
ctgggtgtcg acagcaaaaa cattttcaac ttcaaggtca gtcaagaagg acttaagctc    32820
```

```
tcaaatgaca tgatgggctc atatgctgaa atgaaatttg accacacaaa cagtctgaac    32880
attgcaggct tatcactgga cttctcttca aaacttgaca acatttacag ctctgacaag    32940
ttttataagc aaactgttaa tttacagcta cagccctatt ctctggtaac tactttaaac    33000
agtgacctga aatacaatgc tctggatctc accaacaatg ggaaactacg gctagaaccc    33060
ctgaagctgc atgtggctgg taacctaaaa ggagcctacc aaaataatga aataaaacac    33120
atctatgcca tctcttctgc tgccttatca gcaagctata aagcagacac tgttgctaag    33180
gttcagggtg tggagtttag ccatcggctc aacacagaca tcgctgggct ggcttcagcc    33240
attgacatga gcacaaacta taattcagac tcactgcatt tcagcaatgt cttccgttct    33300
gtaatggccc cgtttaccat gaccatcgat gcacatacaa atggcaatgg gaaactcgct    33360
ctctggggag aacatactgg gcagctgtat agcaaattcc tgttgaaagc agaacctctg    33420
gcatttactt tctctcatga ttacaaaggc tccacaagtc atcatctcgt gtctaggaaa    33480
agcatcagtg cagctcttga acacaaagtc agtgccctgc ttactccagc tgagcagaca    33540
ggcacctgga aactcaagac ccaatttaac aacaatgaat acagccagga cttggatgct    33600
tacaacacta aagataaaat tggcgtggag cttactggac gaactctggc tgacctaact    33660
ctactagact ccccaattaa agtgccactt ttactcagtg agcccatcaa tatcattgat    33720
gctttagaga tgagagatgc cgttgagaag ccccaagaat ttacaattgt tgcttttgta    33780
aagtatgata aaaaccaaga tgttcactcc attaacctcc catttttga gaccttgcaa    33840 gaatattttg agaggaatcg acaaaccatt atagttgtac tggaaaacgt acagagaaac    33900
ctgaagcaca tcaatattga tcaatttgta agaaaataca gagcagccct gggaaaactc    33960
ccacagcaag ctaatgatta tctgaattca ttcaattggg agagacaagt ttcacatgcc    34020
aaggagaaac tgactgctct cacaaaaaag tatagaatta cagaaaatga tatacaaatt    34080
gcattagatg atgccaaaat caactttaat gaaaaactat ctcaactgca gacatatatg    34140
atacaatttg atcagtatat taaagatagt tatgatttac atgatttgaa aatagctatt    34200
gctaatatta ttgatgaaat cattgaaaaa ttaaaaagtc ttgatgagca ctatcatatc    34260
cgtgtaaatt tagtaaaaac aatccatgat ctacatttgt ttattgaaaa tattgatttt    34320
aacaaaagtg gaagtagtac tgcatcctgg attcaaaatg tggatactaa gtaccaaatc    34380
agaatccaga tacaagaaaa actgcagcag cttaagagac acatacagaa tatagacatc    34440
cagcacctag ctggaaagtt aaaacaacac attgaggcta ttgatgttag agtgctttta    34500
gatcaattgg gaactacaat ttcatttgaa agaataaatg acattcttga gcatgtcaaa    34560
cactttgtta taaatcttat tggggatttt gaagtagctg agaaaatcaa tgccttcaga    34620
gccaaagtcc atgagttaat cgagaggtat gaagtagacc aacaaatcca ggttttaatg    34680 gataaaattag tagagttggc ccaccaatac aagttgaagg agactattca gaagctaagc    34740
aatgtcctac aacaagttaa gataaaagat tactttgaga aattggttgg atttattgat    34800
gatgctgtca agaagcttaa tgaattatct tttaaaacat tcattgaaga tgttaacaaa    34860
ttccttgaca tgttgataaa gaaattaaag tcatttgatt accaccagtt tgtagatgaa    34920
accaatgaca aaatccgtga ggtgactcag agactcaatg tgaaattcca ggctctgaa    34980 ctaccacaaa aagctgaagc attaaaactg ttttttagagg aaaccaaggc cacagttgca    35040
gtgtatctgg aaagcctaca ggacaccaaa ataaccttaa tcatcaattg gttacaggag    35100
gctttaagtt cagcatcttt ggctcacatg aaggccaaat tccgagagac cctagaagat    35160
acacgagacc gaatgtatca aatggacatt cagcaggaac ttcaacgata cctgtctctg    35220
```

| | | | | |
|---|---|---|---|---|
| gtaggccagg | tttatagcac | acttgtcacc | tacatttctg | attggtggac tcttgctgct 35280 |
| aagaaccttta | ctgactttgc | agagcaatat | tctatccaag | attgggctaa acgtatgaaa 35340 |
| gcattggtag | agcaagggtt | cactgttcct | gaaatcaaga | ccatccttgg gaccatgcct 35400 |
| gcctttgaag | tcagtcttca | ggctcttcag | aaagctacct | tccagacacc tgattttata 35460 |
| gtcccccctaa | cagatttgag | gattccatca | gttcagataa | acttcaaaga cttaaaaaat 35520 |
| ataaaaatcc | catccaggtt | ttccacacca | gaatttacca | tccttaacac cttccacatt 35580 |
| ccttcctttta | caattgactt | tgtagaaatg | aaagtaaaga | tcatcagaac cattgaccag 35640 |
| atgctgaaca | gtgagctgca | gtggcccgtt | ccagatatat | atctcaggga tctgaaggtg 35700 |
| gaggacattc | ctctagcgag | aatcaccctg | ccagacttcc | gtttaccaga aatcgcaatt 35760 |
| ccagaattca | taatcccaac | tctcaacctt | aatgattttc | aagttcctga ccttcacata 35820 |
| ccagaattcc | agcttcccca | catctcacac | acaattgaag | tacctacttt tggcaagcta 35880 |
| tacagtattc | tgaaaatcca | atctcctctt | ttcacattag | atgcaaatgc tgacataggg 35940 |
| aatggaacca | cctcagcaaa | cgaagcaggt | atcgcagctt | ccatcactgc caaggagag 36000 |
| tccaaattag | aagttctcaa | ttttgatttt | caagcaaatg | cacaactctc aaaccctaag 36060 |
| attaatccgc | tggctctgaa | ggagtcagtg | aagttctcca | gcaagtacct gagaacggag 36120 |
| catgggagtg | aaatgctgtt | ttttggaaat | gctattgagg | gaaaatcaaa cacagtggca 36180 |
| agtttacaca | cagaaaaaaa | tacactggag | cttagtaatg | gagtgattgt caagataaac 36240 |
| aatcagctta | ccctggatag | caacactaaa | tacttccaca | aattgaacat ccccaaactg 36300 |
| gacttctcta | gtcaggctga | cctgcgcaac | gagatcaaga | cactgttgaa agctggccac 36360 |
| atagcatgga | cttcttctgg | aaaagggtca | tggaaatggg | cctgccccag attctcagat 36420 |
| gagggaacac | atgaatcaca | aattagtttc | accatagaag | gaccccctcac ttcctttgga 36480 |
| ctgtccaata | agatcaatag | caaacaccta | agagtaaacc | aaaacttggt ttatgaatct 36540 |
| ggctccctca | acttttctaa | acttgaaatt | caatcacaag | tcgattccca gcatgtgggc 36600 |
| cacagtgttc | taactgctaa | aggcatggca | ctgtttggag | aagggaaggc agagtttact 36660 |
| gggaggcatg | atgctcattt | aaatggaaag | gttattggaa | ctttgaaaaa ttctcttttc 36720 |
| ttttcagccc | agccatttga | gatcacggca | tccacaaaca | atgaagggaa tttgaaagtt 36780 |
| cgttttccat | taaggttaac | agggaagata | gacttcctga | ataactatgc actgtttctg 36840 |
| agtcccagtg | cccagcaagc | aagttggcaa | gtaagtgcta | ggttcaatca gtataagtac 36900 |
| aaccaaaatt | tctctgctgg | aaacaacgag | aacattatgg | aggcccatgt aggaataaat 36960 |
| ggagaagcaa | atctggattt | cttaaacatt | cctttaacaa | ttcctgaaat gcgtctacct 37020 |
| tacacaataa | tcacaactcc | tccactgaaa | gatttctctc | tatgggaaaa aacaggcttg 37080 |
| aaggaattct | tgaaaacgac | aaagcaatca | tttgatttaa | gtgtaaaagc tcagtataag 37140 |
| aaaaacaaac | acaggcattc | catcacaaat | cctttggctg | tgctttgtga gtttatcagt 37200 |
| cagagcatca | aatcctttga | caggcatttt | gaaaaaaaca | gaaacaatgc attagatttt 37260 |
| gtcaccaaat | cctataatga | aacaaaaatt | aagtttgata | agtacaaagc tgaaaaatct 37320 |
| cacgcgagc | tccccaggac | cttttcaaatt | cctggataca | ctgttccagt tgtcaatgtt 37380 |
| gaagtgtctc | cattcaccat | agagatgtcg | gcattcggct | atgtgttccc aaaagcagtc 37440 |
| agcatgccta | gttctccat | cctaggttct | gacgtccgtg | tgccttcata cacattaatc 37500 |
| ctgccatcat | tagagctgcc | agtccttcat | gtccctagaa | atctcaagct ttctcttcca 37560 |

```
gatttcaagg aattgtgtac cataagccat attttttattc ctgccatggg caatattacc   37620
tatgatttct cctttaaatc aagtgtcatc acactgaata ccaatgctga actttttaac   37680
cagtcagata ttgttgctca tctcctttct tcatcttcat ctgtcattga tgcactgcag   37740
tacaaattag agggcaccac aagattgaca agaaaaaggg gattgaagtt agccacagct   37800
ctgtctctga gcaacaaatt tgtggagggt agtcataaca gtactgtgag cttaaccacg   37860
aaaaatatgg aagtgtcagt ggcaacaacc acaaaagccc aaattccaat tttgagaatg   37920
aatttcaagc aagaacttaa tggaaatacc aagtcaaaac ctactgtctc ttcctccatg   37980
gaatttaagt atgatttcaa ttcttcaatg ctgtactcta ccgctaaagg agcagttgac   38040
cacaagctta gcttggaaag cctcacctct tactttttcca ttgagtcatc taccaaagga   38100
gatgtcaagg gttcggttct ttctcgggaa tattcaggaa ctattgctag tgaggccaac   38160
acttacttga attccaagag cacacggtct tcagtgaagc tgcagggcac ttccaaaatt   38220
gatgatatct ggaaccttga agtaaaagaa aattttgctg gagaagccac actccaacgc   38280
atatattccc tctgggagca cagtacgaaa aaccacttac agctagaggg cctctttttc   38340
accaacggag aacatacaag caaagccacc ctggaactct ctccatggca aatgtcagct   38400
cttgttcagg tccatgcaag tcagcccagt tccttccatg atttccctga ccttggccag   38460
gaagtggccc tgaatgctaa cactaagaac cagaagatca gatggaaaaa tgaagtccgg   38520
attcattctg ggtcttttcca gagccaggtc gagctttcca atgaccaaga aaaggcacac   38580
cttgacattg caggatcctt agaaggacac ctaaggttcc tcaaaaatat catcctacca   38640
gtctatgaca agagcttatg ggatttccta aagctggatg taaccaccag cattggtagg   38700
agacagcatc ttcgtgtttc aactgccttt gtgtacacca aaaccccaa tggctattca   38760
ttctccatcc ctgtaaaagt tttggctgat aaattcatta ttcctgggct gaaactaaat   38820
gatctaaatt cagttcttgt catgcctacg ttccatgtcc catttacaga tcttcaggtt   38880
ccatcgtgca aacttgactt cagagaaata caaatctata agaagctgag aacttcatca   38940
tttgccctca acctaccaac actccccgag gtaaaattcc ctgaagttga tgtgttaaca   39000
aaatattctc aaccagaaga ctccttgatt ccctttttg agataaccgt gcctgaatct   39060
cagttaactg tgtcccagtt cacgcttcca aaaagtgttt cagatggcat tgctgctttg   39120
gatctaaatg cagtagccaa caagatcgca gactttgagt tgcccaccat catcgtgcct   39180
gagcagacca ttgagattcc ctccattaag ttctctgtac ctgctggaat tgtcattcct   39240
tccttttcaag cactgactgc acgctttgag gtagactctc ccgtgtataa tgccacttgg   39300
agtgccagtt tgaaaaacaa agcagattat gttgaaacag tcctggattc cacatgcagc   39360
tcaaccgtac agttcctaga atatgaacta aatggtaaga aatatcctgc ctcctctcct   39420
agatactgta tattttcaat gagagttatg agtaaataat tatgtattta gttgtgagta   39480
gatgtacaat tactcaatgt cacaaaattt taagtaagaa aagagataca tgtatacctt   39540
acacgtaaaa accaaactgt agaaaatcta gtgtcattca agacaaacag ctttaaagaa   39600
aatggatttt tctgtaatta ttttaggact aacaatgtct tttaactatt tatttttaaaa   39660
taagtgtgag ctgtacattg catatttttaa acacaagtga aatatctggt taggatagaa   39720
ttctcccagt tttcacaatg aaaacatcaa cgtcctactg ttatgaatct aataaaatac   39780
aaaatctctc ctatacagtt ttgggaacac acaaaatcga agatggtacg ttagcctcta   39840
agactaaagg aacatttgca caccgtgact tcagtgcaga atatgaagaa gatggcaaat   39900
atgaaggact tcagtatgga gcttttattg aattgaaacc ttatacctt tgaaaactca   39960
```

```
ttgtgatttt cttcatctcc ataccccttt cgtgatagct catctgtttt tctgctttca    40020
gggaatggga aggaaaagcg cacctcaata tcaaaagccc agcgttcacc gatctccatc    40080
tgcgctacca gaaagacaag aaaggcatct ccacctcagc agcctcccca gccgtaggca    40140
ccgtgggcat ggatatggat gaagatgacg acttttctaa atggaacttc tactacagcc    40200
ctcaggtaaa taccacctaa tgagtgacac gcccccaaga gcgagtggag aattggggca    40260
gatacattta attcaggacc aaatattcag agattcccca aactaggtga agacaggcg     40320
gtaagcaact tcttctctga ggaaatattc tctagaaagt attacaatga gtccttgatt    40380
gattttaatg tttagatgca cacatgacat cccatcagca ctattattta ttaattctgg    40440
gcaaatccag gaagatgagg gttataccto atcatctaaa tcataggcaa gctcagccat    40500
aggcagggta tattttttcag agaggactgg tttctgtagt atttaaaact ttaaaattct    40560
tccccacaat agaattgcta gatgagatac atcaaattcc tctcatgtca tttacaagct    40620
ctgccagggc caaatcaagg gtgacattac cagaggagaa gaccaaacat ggttctatga    40680
ctgttactaa aagtttgtca tgggcttgga gaatgcgtac tgatgttggg attctgggtc    40740
tctgcagggt gggctccaac ttgccttttt tgctatttct tcttttccta tctgtcattt    40800
cctgactctt cttctctctc ctcttctttc tcttcccccc actcctcttc cagttttcag    40860
tcctaggaag gctttaattt taagtgtcac aatgtaaatg acaaacagca agcgttttg     40920
ttaaatcctt tctggggcat gtgataaaga gaaattaaca acagtagact tatttaacca    40980
taaaacaaac acatgaactg acatatgaaa gataaatccc tttcagtata tgaaagattc    41040
tctgatcttt attttttaact gctaatgaag ttttagtgta ctatattgtg taattggagt    41100
aattgaaaac atgttatttt ttttttttctc tctgtttagt cctctccaga taaaaaactc    41160
accatattca aaactgagtt gagggtccgg gaatctgatg aggaaactca gatcaaagtt    41220
aattgggaag aagaggcagc ttctggcttg ctaacctctc tgaaagacaa cgtgcccaag    41280
gccacagggg tccttttatga ttatgtcaac aagtaccact gggaacacac agggctcacc    41340
ctgagagaag tgtcttcaaa gctgagaaga aatctgcaga acaatgctga gtgggtttat    41400
caagggccca ttaggcaaat tgatgatatc gacgtgaggt tccagaaagc agccagtggc    41460
accactggga cctaccaaga gtggaaggac aaggcccaga atctgtacca ggaactgttg    41520
actcaggaag gccaagccag tttccaggga ctcaaggata acgtgtttga tggcttggta    41580
cgagttactc aagaattcca tatgaaagtc aagcatctga ttgactcact cattgatttt    41640
ctgaacttcc ccagattcca gtttccgggg aaacctggga tatacactag ggaggaactt    41700
tgcactatgt tcataaggga ggtagggacg gtactgtccc aggtatattc gaaagtccat    41760
aatggttcag aaatactgtt ttcctatttc caagacctag tgattacact tcctttcgag    41820
ttaaggaaac ataaactaat agatgtaatc tcgatgtata gggaactgtt gaaagattta    41880
tcaaaagaag cccaagaggt atttaaagcc attcagtctc tcaagaccac agaggtgcta    41940
cgtaatcttc aggacctttt acaattcatt ttccaactaa tagaagataa cattaaacag    42000
ctgaaagaga tgaaatttac ttatcttatt aattatatcc aagatgagat caacacaatc    42060
ttcagtgatt atatcccata tgtttttaaa ttgttgaaag aaaacctatg ccttaatctt    42120
cataagttca atgaatttat tcaaaacgag cttcaggaag cttctcaaga gttacagcag    42180
atccatcaat acattatggc ccttcgtgaa gaatattttg atccaagtat agttggctgg    42240
acagtgaaat attatgaact tgaagaaaag atagtcagtc tgatcaagaa cctgttagtt    42300
```

```
gctcttaagg acttccattc tgaatatatt gtcagtgcct ctaactttac ttcccaactc    42360
tcaagtcaag ttgagcaatt tctgcacaga aatattcagg aatatcttag catccttacc    42420
gatccagatg gaaaagggaa agagaagatt gcagagcttt ctgccactgc tcaggaaata    42480
attaaaagcc aggccattgc gacgaagaaa ataatttctg attaccacca gcagtttaga    42540
tataaactgc aagattttc agaccaactc tctgattact atgaaaaatt tattgctgaa     42600
tccaaaagat tgattgacct gtccattcaa aactaccaca catttctgat atacatcacg    42660
gagttactga aaaagctgca atcaaccaca gtcatgaacc cctacatgaa gcttgctcca    42720
ggagaactta ctatcatcct ctaattttt aaaagaaatc ttcatttatt cttcttttcc     42780
aattgaactt tcacatagca cagaaaaaat tcaaactgcc tatattgata aaccataca    42840 gtgagccagc cttgcagtag gcagtagact ataagcagaa gcacatatga actgacctg    42900 caccaaagct ggcaccaggg ctcggaaggt ctctgaactc agaaggatgg catttttgc    42960 aagttaaaga aaatcaggat ctgagttatt ttgctaaact tggggagga ggaacaaata     43020 aatggagtct ttattgtgta tcataccact gaatgtggct catttgtatt gaaagacagt    43080
gaaacgaggg cattgataaa atgttctggc acagcaaaac ctctagaaca catagtgtga    43140
tttaagtaac agaataaaaa tggaaacgga gaaattatgg agggaaatat tttgcaaaaa    43200
tatttaaaaa gatgaggtaa ttgtgttttt ataattaaat attttataat taaatatttt    43260
ataattaaaa tatttataat taaatatttt ataattaaaa tatttataat taaatatttt    43320
ataattaaag tatttataat taaatatttt ataattaaaa tatttataat taaatatttt    43380
ataattaaaa tatttataat taaatatttt ataattaaaa tatttataat taaatatttt    43440
ataat                                                                43445

<210> SEQ ID NO 2
<211> LENGTH: 43445
<212> TYPE: DNA
<213> ORGANISM: Artificial Sequence
<220> FEATURE:
<223> OTHER INFORMATION: Antisense Oligonucleotide

<400> SEQUENCE: 2
attataaaat atttaattat aaatatttta attataaaat atttaattat aaatatttta      60
attataaaat atttaattat aaatatttta attataaaat atttaattat aaatacttta     120
attataaaat atttaattat aaatatttta attataaaat atttaattat aaatatttta     180
attataaata ttttaattat aaaatatttta attataaaaa cacaattacc tcatcttttt    240
aaatattttt gcaaatatt tccctccata atttctccgt ttccattttt attctgttac     300
ttaaatcaca ctatgtgttc tagaggtttt gctgtgccag aacattttat caatgccctc    360
gtttcactgt ctttcaatac aaatgagcca cattcagtgg tatgatacac aataaagact    420
ccatttattt gttcctcctc ccccaagttt agcaaaataa ctcagatcct gattttcttt    480
aacttgcaaa aaatgccatc cttctgagtt cagagacctt ccgagccctg gtgccagctt    540
tggtgcaggt ccagttcata tgtgcttctg cttatagtct actgcctact gcaaggctgg    600
ctcactgtat ggttttatca atataggcag tttgaattt ttctgtgcta tgtgaaagtt     660
caattggaaa agaagaataa atgaagattt cttttaaaaa attagaggat gatagtaagt    720
tctcctggag caagcttcat gtaggggttc atgactgtgg ttgattgcag cttttttcagt   780 aactccgtga tgtatatcag aaatgtgtgg tagttttgaa tggacaggtc aatcaatctt    840
ttggattcag caataaattt ttcatagtaa tcagagagtt ggtctgaaaa atcttgcagt    900
```

```
ttatatctaa actgctggtg gtaatcagaa attattttct tcgtcgcaat ggcctggctt      960
ttaattattt cctgagcagt ggcagaaagc tctgcaatct tctctttccc ttttccatct     1020
ggatcggtaa ggatgctaag atattcctga atatttctgt gcagaaattg ctcaacttga     1080
cttgagagtt gggaagtaaa gttagaggca ctgacaatat attcagaatg gaagtcctta     1140
agagcaacta acaggttctt gatcagactg actatctttt cttcaagttc ataatatttc     1200
actgtccagc caactatact tggatcaaaa tattcttcac gaagggccat aatgtattga     1260
tggatctgct gtaactcttg agaagcttcc tgaagctcgt tttgaataaa ttcattgaac     1320
ttatgaagat taaggcatag gttttctttc aacaatttaa aaacatatgg gatataatca     1380
ctgaagattg tgttgatctc atcttggata taattaataa gataagtaaa tttcatctct     1440
ttcagctgtt taatgttatc ttctattagt tggaaaatga attgtaaaag gtcctgaaga     1500
ttacgtagca cctctgtggt cttgagagac tgaatggctt taaataccte ttgggcttct     1560
tttgataaat ctttcaacag ttccctatac atcgagatta catctattag tttatgtttc     1620
cttaactcga aaggaagtgt aatcactagg tcttggaaat aggaaaacag tatttctgaa     1680
ccattatgga ctttcgaata tacctgggac agtaccgtcc ctacctccct tatgaacata     1740
gtgcaaagtt cctccctagt gtatatccca ggtttccccg gaaactggaa tctggggaag     1800
ttcagaaaat caatgagtga gtcaatcaga tgcttgactt tcatatggaa ttcttgagta     1860
actcgtacca agccatcaaa cacgttatcc ttgagtccct ggaaactggc ttggccttcc     1920
tgagtcaaca gttcctggta cagattctgg gccttgtcct tccactcttg gtaggtccca     1980
gtggtgccac tggctgcttt ctggaacctc acgtcgatat catcaatttg cctaatggcc     2040
ccttgataaa cccactcagc attgttctgc agatttcttc tcagctttga agacacttct     2100
ctcagggtga gccctgtgtg ttcccagtgg tacttgttga cataatcata aaggacccct     2160
gtggccttgg gcacgttgtc tttcagagag gttagcaagc cagaagctgc ctcttcttcc     2220
caattaactt tgatctgagt ttcctcatca gattcccgga ccctcaactc agttttgaat     2280
atggtgagtt ttttatctgg agaggactaa acagagagaa aaaaaaaat aacatgtttt      2340
caattactcc aattacacaa tatagtacac taaaacttca ttagcagtta aaaataaaga     2400
tcagagaatc tttcatatac tgaaagggat ttatctttca tatgtcagtt catgtgtttg     2460
ttttatggtt aaataagtct actgttgtta atttctcttt atcacatgcc ccagaaagga     2520
tttaacaaaa acgcttgctg tttgtcattt acattgtgac acttaaaatt aaagccttcc     2580
taggactgaa aactggaaga gggagtgggg gaagagaaag aagaggagag agaagaagag     2640
tcaggaaatg acagatagga aaagaagaaa tagcaaaaaa ggcaagttgg agcccaccct     2700
gcagagaccc agaatcccaa catcagtacg cattctccaa gcccatgaca aacttttagt     2760
aacagtcata gaaccatgtt tggtcttctc ctctggtaat gtcacccttg atttggccct     2820
ggcagagctt gtaaatgaca tgagaggaat ttgatgtatc tcatctagca attctattgt     2880
ggggaagaat tttaaagttt taaatactac agaaaccagt cctctctgaa aaatataccc     2940
tgcctatggc tgagcttgcc tatgatttag atgatgaggt ataaccctca tcttcctgga     3000
tttgcccaga attaataaat aatagtgctg atgggatgtc atgtgtgcat ctaaacatta     3060
aaatcaatca aggactcatt gtaatacttt ctagagaata tttcctcaga gaagaagttg     3120
cttaccgcct gtctttcacc tagtttgggg aatctctgaa tatttggtcc tgaattaaat     3180
gtatctgccc caattctcca ctcgctcttg ggggcgtgtc actcattagg tggtatttac     3240
```

```
ctgagggctg tagtagaagt tccatttaga aaagtcgtca tcttcatcca tatccatgcc   3300
cacggtgcct acggctgggg aggctgctga ggtggagatg cctttcttgt ctttctggta   3360
gcgcagatgg agatcggtga acgctgggct tttgatattg aggtgcgctt ttccttccca   3420
ttccctgaaa gcagaaaaac agatgagcta tcacgaaagg ggtatggaga tgaagaaaat   3480
cacaatgagt tttcaaaagg tataaggttt caattcaata aaagctccat actgaagtcc   3540
ttcatatttg ccatcttctt catattctgc actgaagtca cggtgtgcaa atgttccttt   3600
agtcttagag gctaacgtac catcttcgat tttgtgtgtt cccaaaactg tataggagag   3660
attttgtatt ttattagatt cataacagta ggacgttgat gttttcattg tgaaaactgg   3720
gagaattcta tcctaaccag atatttcact tgtgtttaaa atatgcaatg tacagctcac   3780
acttatttta aaataaatag ttaaaagaca ttgttagtcc taaaataatt acagaaaaat   3840
ccattttctt taaagctgtt tgtcttgaat gacactagat tttctacagt ttggttttta   3900
cgtgtagggt atacatgtat ctcttttctt acttaaaatt ttgtgacatt gagtaattgt   3960
acatctactc acaactaaat acataattat ttactcataa ctctcattga aaatatacag   4020
tatctaggag aggaggcagg atatttctta ccatttagtt catattctag gaactgtacg   4080
gttgagctgc atgtggaatc caggactgtt tcaacataat ctgctttgtt tttcaaactg   4140
gcactccaag tggcattata cacgggagag tctacctcaa agcgtgcagt cagtgcttga   4200
aaggaaggaa tgacaattcc agcaggtaca gagaacttaa tggagggaat ctcaatggtc   4260
tgctcaggca cgatgatggt gggcaactca agtctgcga tcttgttggc tactgcattt   4320
agatccaaag cagcaatgcc atctgaaaca cttttttggaa gcgtgaactg ggacacagtt   4380
aactgagatt caggcacggt tatctcaaaa aagggaatca aggagtcttc tggttgagaa   4440
tattttgtta acacatcaac ttcagggaat tttacctcgg ggagtgttgg taggttgagg   4500
gcaaatgatg aagttctcag cttcttatag atttgtattt ctctgaagtc aagtttgcac   4560
gatggaacct gaagatctgt aaatgggaca tggaacgtag gcatgacaag aactgaattt   4620
agatcattta gtttcagccc aggaataatg aatttatcag ccaaaacttt tacagggatg   4680
gagaatgaat agccattggg gttttttggtg tacacaaagg cagttgaaaac acgaagatgc   4740 tgtctcctac caatgctggt ggttacatcc agctttagga aatcccataa gctcttgtca   4800
tagactggta ggatgatatt tttgaggaac cttaggtgtc cttctaagga tcctgcaatg   4860
tcaaggtgtg ccttttcttg gtcattggaa agctcgacct ggctctggaa agacccagaa   4920
tgaatccgga cttcattttt ccatctgatc ttctggttct tagtgttagc attcagggcc   4980
acttcctggc caaggtcagg gaaatcatgg aaggaactgg gctgacttgc atggacctga   5040
acaagagctg acatttgcca tggagagagt tccagggtgg ctttgcttgt atgttctccg   5100
ttggtgaaaa agaggccctc tagctgtaag tggttttttcg tactgtgctc ccagagggaa   5160
tatatgcgtt ggagtgtggc ttctccagca aaatttttctt ttacttcaag gttccagata   5220
tcatcaattt tggaagtgcc ctgcagcttc actgaagacc gtgtgctctt ggaattcaag   5280
taagtgttgg cctcactagc aatagttcct gaatattccc gagaaagaac cgaacccttg   5340
acatctcctt tggtagatga ctcaatgaa aagtaagagg tgaggctttc caagctaagc   5400
ttgtggtcaa ctgctccttt agcggtagag tacagcattg aagaattgaa atcatactta   5460
aattccatgg aggaagagac agtaggtttt gacttggtat ttccattaag ttcttgcttg   5520
aaattcattc tcaaaattgg aatttgggct tttgtggttg ttgccactga cacttccata   5580
tttttcgtgg ttaagctcac agtactgtta tgactaccct ccacaaattt gttgctcaga   5640
```

```
gacagagctg tggctaactt caatcccctt tttcttgtca atcttgtggt gccctctaat    5700
ttgtactgca gtgcatcaat gacagatgaa gatgaagaaa ggagatgagc aacaatatct    5760
gactggttaa aaagttcagc attggtattc agtgtgatga cacttgattt aaaggagaaa    5820
tcataggtaa tattgcccat ggcaggaata aaaatatggc ttatggtaca caattccttg    5880
aaatctggaa gagaaagctt gagatttcta gggacatgaa ggactggcag ctctaatgat    5940
ggcaggatta atgtgtatga aggcacacgg acgtcagaac ctaggatgga gaaactaggc    6000
atgctgactg cttttgggaa cacatagccg aatgccgaca tctctatggt gaatggagac    6060
acttcaacat tgacaactgg aacagtgtat ccaggaattt gaaaggtcct ggggagctcg    6120
tcgtgagatt tttcagcttt gtacttatca aacttaattt ttgtttcatt ataggatttg    6180
gtgacaaaat ctaatgcatt gtttctgttt ttttcaaaat gcctgtcaaa ggatttgatg    6240
ctctgactga taaactcaca agcacagcc aaaggatttg tgatggaatg cctgtgtttg    6300
tttttcttat actgagcttt tacacttaaa tcaaatgatt gctttgtcgt tttcaagaat    6360
tccttcaagc ctgtttttc ccatagagag aaatctttca gtggaggagt tgtgattatt    6420
gtgtaaggta gacgcatttc aggaattgtt aaaggaatgt ttaagaaatc cagatttgct    6480
tctccattta ttcctacatg ggcctccata atgttctcgt tgtttccagc agagaaattt    6540
tggttgtact tatactgatt gaacctagca cttacttgcc aacttgcttg ctgggcactg    6600
ggactcagaa acagtgcata gttattcagg aagtctatct tccctgttaa ccttaatgga    6660
aaacgaactt tcaaattccc ttcattgttt gtggatgccg tgatctcaaa tggctgggct    6720
gaaaagaaaa gagaattttt caaagttcca ataacctttc catttaaatg agcatcatgc    6780
ctcccagtaa actctgcctt cccttctcca acagtgccaa tgcctttagc agttagaaca    6840
ctgtggccca catgctggga atcgacttgt gattgaattt caagtttaga aaagttgagg    6900
gagccagatt cataaaccaa gttttggttt actcttaggt gtttgctatt gatcttattg    6960
gacagtccaa aggaagtgag gggtccttct atggtgaaac taatttgtga ttcatgtgtt    7020
ccctcatctg agaatctggg gcaggcccat ttccatgacc ttttccaga agaagtccat    7080 gctatgtggc cagctttcaa cagtgtcttg atctcgttgc gcaggtcagc ctgactagag    7140
aagtccagtt tggggatgtt caatttgtgg aagtatttag tgttgctatc cagggtaagc    7200
tgattgttta tcttgacaat cactccatta ctaagctcca gtgtattttt ttctgtgtgt    7260
aaacttgcca ctgtgtttga tttttccctca atagcatttc caaaaacag catttcactc    7320 ccatgctccg ttctcaggta cttgctggag aacttcactg actccttcag agccagcgga    7380
ttaatcttag ggtttgagag ttgtgcattt gcttgaaaat caaaattgag aacttctaat    7440
ttggactctc ctttggcagt gatggaagct gcgatacctg cttcgtttgc tgaggtggtt    7500
ccattcccta tgtcagcatt tgcatctaat gtgaaaagag gagattggat tttcagaata    7560
ctgtatagct tgccaaaagt aggtacttca attgtgtgtg agatgtgggg aagctggaat    7620
tctggtatgt gaaggtcagg aacttgaaaa tcattaaggt tgagagttgg gattatgaat    7680
tctggaattg cgatttctgg taaacggaag tctggcaggg tgattctcgc tagaggaatg    7740
tcctccacct tcagatccct gagatatata tctggaacgg gccactgcag ctcactgttc    7800
agcatctggt caatggttct gatgatcttt actttcattt ctacaaagtc aattgtaaag    7860
gaaggaatgt ggaaggtgtt aaggatggta aattctggtg tggaaaacct ggatgggatt    7920
tttatatttt ttaagtcttt gaagtttatc tgaactgatg gaatcctcaa atctgttagg    7980
```

```
gggactataa aatcaggtgt ctggaaggta gctttctgaa gagcctgaag actgacttca      8040
aaggcaggca tggtcccaag gatggtcttg atttcaggaa cagtgaaccc ttgctctacc      8100
aatgctttca tacgtttagc ccaatcttgg atagaatatt gctctgcaaa gtcagtaagg      8160
ttcttagcag caagagtcca ccaatcagaa atgtaggtga caagtgtgct ataaacctgg      8220
cctaccagag acaggtatcg ttgaagttcc tgctgaatgt ccatttgata cattcggtct      8280
cgtgtatctt ctagggtctc tcggaatttg gccttcatgt gagccaaaga tgctgaactt      8340
aaagcctcct gtaaccaatt gatgattaag gttatttttgg tgtcctgtag gctttccaga     8400
tacactgcaa ctgtggcctt ggtttcctct aaaaacagtt ttaatgcttc agcttttttgt    8460 ggtagttcca gagcctgaat ttcaccattg agtctctgag tcacctcacg gattttgtca      8520
ttggtttcat ctacaaactg gtggtaatca aatgacttta atttctttat caacatgtca      8580
aggaatttgt taacatcttc aatgaatgtt ttaaaagata attcattaag cttcttgaca      8640
gcatcatcaa taaatccaac caatttctca aagtaatctt ttatcttaac ttgttgtagg      8700
acattgctta gcttctgaat agtctccttc aacttgtatt ggtgggccaa ctctactaat      8760
ttatccatta aaacctggat ttgttggtct acttcatacc tctcgattaa ctcatggact      8820
ttggctctga aggcattgat tttctcagct acttcaaaat ccccaataag atttataaca      8880
aagtgtttga catgctcaag aatgtcattt attctttcaa atgaaattgt agttcccaat      8940
tgatctaaaa gcactctaac atcaatagcc tcaatgtgtt gttttaactt tccagctagg      9000
tgctggatgt ctatattctg tatgtgtctc ttaagctgct gcagttttttc ttgtatctgg     9060 attctgattt ggtacttagt atccacattt tgaatccagg atgcagtact acttccactt      9120
ttgttaaaat caatattttc aataaacaaa tgtagatcat ggattgtttt tactaaattt      9180
acacggatat gatagtgctc atcaagactt tttaatttttt caatgatttc atcaataata     9240
ttagcaatag ctattttcaa atcatgtaaa tcataactat ctttaatata ctgatcaaat      9300
tgtatcatat atgtctgcag ttgagatagt ttttcattaa agttgatttt ggcatcatct      9360
aatgcaattt gtatatcatt ttctgtaatt ctatacttttt ttgtgagagc agtcagtttc     9420
tccttggcat gtgaaacttg tctctcccaa ttgaatgaat tcagataatc attagcttgc      9480
tgtgggagtt ttcccagggc tgctctgtat tttcttacaa attgatcaat attgatgtgc      9540
ttcaggtttc tctgtacgtt ttccagtaca actataatgg tttgtcgatt cctctcaaaa      9600
tattcttgca aggtctcaaa aaatgggagg ttaatggagt gaacatcttg gtttttatca      9660
tactttacaa aagcaacaat tgtaaattct tggggcttct caacggcatc tctcatctct      9720
aaagcatcaa tgatattgat gggctcactg agtaaaagtg gcactttaat tggggagtct      9780
agtagagtta ggtcagccag agttcgtcca gtaagctcca cgccaatttt atctttagtg      9840
ttgtaagcat ccaagtcctg gctgtattca ttgttgttaa attgggtctt gagtttccag      9900
gtgcctgtct gctcagctgg agtaagcagg gcactgactt tgtgttcaag agctgcactg      9960
atgcttttcc tagacacgag atgatgactt gtggagcctt tgtaatcatg agagaaagta     10020
aatgccagag ttctgctttt caacaggaat ttgctataca gctgcccagt atgttctccc     10080
cagagagcga gtttcccatt gccatttgta tgtgcatcga tggtcatggt aaacggggcc     10140
attacagaac ggaagacatt gctgaaatgc agtgagtctg aattatagtt tgtgctcatg     10200
tcaatggctg aagccagccc agcgatgtct gtgttgagcc gatggctaaa ctccacaccc     10260
tgaaccttag caacagtgtc tgcttttatag cttgctgata aggcagcaga agagatggca     10320
tagatgtgtt ttatttcatt attttggtag gctcctttta ggttaccagc cacatgcagc     10380
```

```
ttcagggtt  ctagccgtag  tttcccattg  ttggtgagat  ccagagcatt  gtatttcagg   10440
tcactgttta  aagtagttac  cagagaatag  ggctgtagct  gtaaattaac  agtttgctta   10500
taaaacttgt  cagagctgta  aatgttgtca  agttttgaag  agaagtccag  tgataagcct   10560
gcaatgttca  gactgtttgt  gtggtcaaat  ttcatttcag  catatgagcc  catcatgtca   10620
tttgagagct  taagtccttc  ttgactgacc  ttgaagttga  aaatgttttt  gctgtcgaca   10680
cccagaatca  tggcctgata  agcacttccc  agtgatagct  ctgtgagggc  ggcttttccca  10740 tccagactga  attttgcatt  gtgttccctg  aagcggccat  tgttgttaa   tttcatagat   10800 gccccagaga  ggccaagctc  tgcattcagc  tcattctcca  gcaccaggag  actacacttc   10860
aagttggtcg  ttgcactggt  agatattcca  tcttggccaa  tccttagtgt  cgccttgtga   10920
gcaccactat  taattttgtc  agtgcctaag  atgtcagcat  ttaactcaag  accatgggaa   10980
tttagtgatc  cagaaagcag  gctgaagaac  ctcaatgact  cgtaatcagc  ctgatattca   11040
gaacgcagca  gtgcattttg  cttagagaag  gtcatatcca  tcttgttaga  agtggcaaag   11100
ttcttatact  tcccattggt  gtcagatttt  aaagtcagct  cgtagttctc  atactttagg   11160
gaagcagtat  ttttaatgat  gccacttttgc  agatcagagg  tggaggtgag  ggagagggtt   11220
ccatcttcat  atcttcctgt  tatctggttg  gtgccttgga  ggtaggagga  gttaaacctc   11280
aggttggact  ctccattgag  ccggccagtg  ttaggatccc  tctgacaaga  caggccatat   11340
gtgcctttag  catagaacga  agagactctg  aactgcccat  caatcttgac  ttctttgaca   11400
aacaaatgct  gtttcttttt  ggagtccaaa  tgaactgaag  cagacatctg  tggtccccag   11460
gaactagatg  catcgaatat  tagtaaacct  tttgagactg  ggttgtttcc  aagttttct    11520 acatgactga  atttgatatt  cgaatctaga  aatttgtggc  gtagagaccc  atcatatgat   11580
agtgtgaacg  tattcttgtg  gtcatatgtt  gttctccag   atcctaacat  aaaaatgaaa   11640
agacattggt  taaattaagc  agtacatttc  cagagcaatc  tctatgttga  aagtcttttca  11700 ataataaagc  cccattttc   tgggccaatt  gtgcaataga  ctcctccatc  tgtaatgcaa   11760
agataaaatc  tgatagcaaa  aggcattcct  ccaggaagcc  ttgcctgacc  accacaggct   11820
ttgtttaggt  tcccttgttg  agtgcttcca  ctctacctta  tacttatata  ctcactttta   11880
tcatagcacc  tctcacactg  aattataatt  gctggcttat  ctgtctactt  tctgttactg   11940
cctactagaa  tatttaatac  acgtgatatg  tttaataaat  atttctattt  gttgaataaa   12000
ataaaagact  tccaagtagc  aaggaagatt  atctgctaga  aagccaaagt  cctttcctcc   12060
ctggaggagg  ctctcctctt  agagcctgcc  atgaactagc  ccggtgcacc  ctttacctga   12120
gcatagctca  ccttgcacat  tgtaggaaag  caggtcaacc  acagagtcag  ccttcatgtg   12180
gtaacgagcc  cgaaggctga  aatggtctgt  gctggtgttg  ccaccactgt  aggaggcgga   12240
ccagttgtac  aagttgctgt  agacattcgt  ggagaggtct  agaacaccca  ggagaggcac   12300
ttgcagttga  tacaacttgg  gaatggtaaa  agtagggact  tggaactctc  gagatggcag   12360
atggaatccc  acagacttga  agtggagggc  tggtgtccta  acagtctcta  acatctttag   12420
atctctggag  gatttgccac  caaaaggcaa  aggaatctca  attttcaaac  tgttcttgtt   12480
caaggtatat  ttgacccggc  catcgctgaa  atgaacaaca  aagataacat  ccccacagtc   12540
agacatcagt  cattcaaagt  tctctgcctc  tgaccttcac  aacaatattg  tacttgcccc   12600
attcccaaag  ccactctgca  cttttctttg  tgctactcct  atgcctggac  ccctttgctt   12660
ttacctccac  ctgtcaaaca  ctcaaatcct  gacaaagctc  ttctaagggc  cactccttat   12720
```

```
cattaccatc ccacctaagt catagccaat ttgtctcatt cttacagtta catagtccct   12780
tgcacctttc tcaaagagca tgtcataatt ttgcttatat aattaattat ttctcatttg   12840
ttgatgtctc catggtatct tcttgaaaga aaaggctata ccttacccag tttctatctt   12900
ctcactgtac ctagtctagc attttgcaca taggggatac ttgatacaaa tttgctaaac   12960
tgaattgaga caacttgatt tgtggaaaga acataggtat ggaagtcagt aagcctgggt   13020
taaagtattt tctcagaatg ctgcctccat ttagtgctca atggctgttc tgactctctc   13080
tagcttaaca gcaagcctgt agtcaataac gcctctagcc attctgaatt cttcacagtc   13140
agagggagaa tttgcttata acaggttgta ctgaataaaa tatcttaggg tgaaagtacc   13200
agaatcctct aatgactttc ttagattctt cctgacaggg ttggtgttct catgtttact   13260
aatgcaaaga tgccacagtg tttgtgctat agttattaat ctccttaaaa tgcttaaatt   13320
atttccttta aaaatttaaa aaaatgtcta aatcatgcta tgtaaaatct ttcatttact   13380
ttgcatggtt caagaagcct tgctgctttc ttcttttacc ttttttaagaa gaggttttct   13440 gggatgtgga agtctggcaa tcccatgttc tggaggttga actccttcag gctattgagg   13500
tggtcttgca aagtctgggt ataaggaaga ctcccagatg ccttctgaag ccatgagctc   13560
attgcctaca aaatgacagg agattttttaa ggtaatgggc ttggatgagc ctcaaagagc   13620
aatgaacatt aggcaaaaat accgatttga caagttaatt attaagctgg acaatgcact   13680
gaaagttaaa aataaataac agaaaattat gaatcttcgt tgccagtcac tgatcactgt   13740
ccatatttat aaaaggaatg tctaacatag tcagcctcct agctggtgtc ctgaagcttc   13800
ctttgatacc actaggcaaa gaactgttct acttagtagc atctctttga tatgtatcac   13860
attcagcttt gtgtaactgg gtaactacac acttgtgaaa gttttttttt ctccccaaga   13920
attccctggg gggaaggaag catgccttat acatctttgg aaaccttcct gcacctagct   13980
cagagttgag gatgtaatta gcacttatat ccatgtattt attgactggc agactcatac   14040
ttacaactat taatttggaa cccacgtgcc ggaaagtcat gtctgtttga gggactctgt   14100
gatccaggag tctattagca tacatatgca agctcttagg ataatcggag agatccacag   14160
ggaaattgga agtcattttt ttggtatcta cattggtgcc tgtgttccat tcaaattcaa   14220
tcttctcttc atctgaaaat acgtaggaaa tagttgtgaa tggtactagt tcagcctgta   14280
accacaggtc tcaacacctg cattactttg gaagtgctca cacaggggaa gagacacata   14340
ccataatgcc atgccaccct cttggaaact gtggagccat aagctgtagc agatgagtcc   14400
atttggagaa gcagttttggc aggcgaccag tgggcgagga tctcacttct ggcttctgct   14460
tgcaaacggg gtatggaaat aacacccttg attttctttt cttccttttgt gtcacaacta   14520 tggtaaagaa aatcagttgg caccaatgat tttgtccttt caatggagat atgcaggatt   14580
aaacagaagt tccatttgtg gtgatcaaaa ccagatacaa ggatggttca gagaaacagc   14640
cacagatcaa actcatcaac ttctaaagcc aacattcagc acaaattaag gactttgcaa   14700
acaggtttag gagaaagaga agttttttga aaactgtttg aatcctgctc tgctatttac   14760
tagctctgtg attttgacca aatgatttaa cccctctgag ctaccatttc cttatccatg   14820
aaacaggaaa actcacagtg acctcgcagt ttattgtgag gaccgagata atttcttttaa   14880 agcacccagc actgtgcttg atacatgaat agtaagtgcc tgataaatgg taggaaaatc   14940 caactgagaca tgcgcagagg gttaaaatgt tgagagcttg gccgggtgca gtggcttaca   15000
cctgtaatcc cagcactttg ggaggccaag gcaggtggat cacagaggtca ggagatcgag   15060 accatcctgg tcaatatggt gaaaccctgt ctctactaaa aatataaaaa ttagctgggt   15120
```

```
gtggtggcat gcacctatag ttccagctcc ttgggaggct taagcaggag aatcacttga    15180
actcgggagg cggaggttgc agtgagccga gattgtgcca ctgcactcca gcctggtgac    15240
agagtgagac tccatctcaa aaaaaaaaaa aattgttgag ggctctctct gccactctga    15300
ttgtagacta ggggagaaca tggcttggtc aggtatgaag tggaagagga ataatgaaaa    15360
gaaccaccca ggcctgcagt gcaggtcaga tgaccctcgg ccttctttac cttaggtggc    15420
ccatgagggc gacctcagta attttcttgt tctgaatgtc cagggtgagt ctgtaagacg    15480
ttttgccctc agtagattca tcattaactc tgaggattgt tccgaggtca acatcaaaat    15540
ccggaatttg gacttcactg gacaaggtca tactctgccg attatatttg aatgtcatgg    15600
tagcctcagt ctgcttcgca cctggacgag tgtataagag aatcaagaga tgtgtggtaa    15660
gaagctatgt tttgggccgg gtgcggtggc tcacacctgt aatcccagca ctttgggagg    15720
ccaaggcggg cagatcatga ggtcaggaga tcaagaccat tctggctaac atggtgaaac    15780
cccgtctcta ctaaaaatac aaaaaattag ccgggcgcgt tggtgggtgc ctgtagtccc    15840
agctactcag gaggctgagg caggagaatg gcatgaaccc gggaggcggg gcttgcagtg    15900
agccgagatg gcaccactgc actgcagcct gggcaaaaga gcgagactcc atctcaaaaa    15960
ataaataaat aaataaataa ataaataaac aaacaaataa ataaataaat aaataaagaa    16020
gctatgtttt ggaaggaaag agaggaaaag gtagagaaac tccaaggaat caatgtgctt    16080
aaacaaaaac acagttcagg attttactga attttttttt tctcattaaa attttttaat    16140
gggtctcatt tactgataat tttaaactca gttgtgttca tgtatgcaag tctttatgga    16200
ttgcctgtta tgagcctatt gtgtgctggg cactgctctt ggtactgggg aatccttgct    16260
ttcatggggc ttaccttcta gtgggggagg tgtacaggca ataaacaagt aacttgctca    16320
tgtcagatgg taatgaatgt tatgaagaag agtaaaactg gatacaagga taaaagaaag    16380
ggatagaaga agtgttattt catacttggt ggtcagagaa attctctctg ataagggcac    16440
atgtgggcag agaccagaat gaaaagaggt tggagccacg ctgagttctg ggaggagcac    16500
attccaggca gaaggtcagg aatgcaaagg ccctgaaatg gggagcactt agcttgtttg    16560
tggaacagca aaggctcgca gcccttctgg gccaggaaga cacgcatatct ctatattact    16620 ttctacccaa gatgcctgtc ctggttcctt gctgcccttg ccctgggctc catctcccca    16680
actccccctt tctttgtaac aagattcccg ggcgtccttc aatccatagg ctggtccatt    16740
ttatatcctt cgtaaaacaa tgtttaccaa acactatttc cccagcgtgc cctgctcctc    16800
cagtgctttc tatcatggga ttttcttcct agtttaattc tgtgatatgc tatccctata    16860
taaaaatttt tccaaagtga acacctaaat gtgccccatt ccctaaaacc tgctcctcgc    16920
tatccctata taatttttttt tccaaagtga acacctaaat ttctcccatt ccctaaaacc    16980
tgctcctcca gtagcccttt ccatctcaat aaatggaagt tccatttttc agttgcccgg    17040
gccaaaaacc ttaggtttgt cttcattccc cttttcctct tacactcaac atccactgta    17100
tcagcaaatc ttgtcagcct aatcttcaaa atatggccag aatccatccc cttctcatat    17160
ctcttctgcc attgccctga tccaaaacaa cactgattcc tgcctggatt attgtgataa    17220
cctacatatt agtttctctg cccttgtctg cccatagtct tttctcaaca taaacataaa    17280
tcaaatcatg aggactcccc aatggctttc gtttaattca tagaaaaagc caaagttctt    17340
accatggcct atgagattat ccttccttca cctctcccata tctctctgtc ctcatcttct    17400
acctcttttc tccctggtct ttctgctcca gccatactgt cttccttcct ttccttgaaa    17460
```

```
catggtagta gtgtgtcagc ctcagggcct ttgcacttgc tggtccctct gcctgttaac    17520
agtcttacca cacggcttct cctcttattt ctgataggtc tccttatgct cactttacca    17580
gggagacttt cccttattat tccaaatgca ctgctttccc tgcccttctt cctccctcct    17640
actcctagcc ctccatagac cagtctacgc tctgttttcc tcctcagtac ttatctgata    17700
ttccaaatat taacttgttt ggttgttcac tgtaacttcc atgaaggcag agactccatt    17760
gttcactgtt ctagcccag gtcttagaat aggcctgccg cttattgggt actcagttaa    17820
cccaggtctt agaataggcc tgccgcttag tgggtactca gttaacctat ttgttaaata    17880
ggttaaatta catgtcttct cctcatgaat tctgaacctg agactgcgag cagagatgag    17940
gcagctgtgt tttgaatact caccttctgc ttgagttaca aacttcaggg tatccaccaa    18000
ggctctgtcc tctctctgga gctcataggt tgcgctgaca gaatactgct caatctctcc    18060
tgtaggcctc agttccagct ctaatctaaa gacattacaa tgaagacagt gcataatgtt    18120
agagctttca aggatggtga ttatgttccc aaaacaattc agcctcaaat gcaacaaaaa    18180
tatggtcctt attttaacat tgtctcttgc ccttaactaa gatgatcttt ttgatccctc    18240
agtcctacaa gaacccaagg caagggcaga caccaggatt cccaagactt tggacaagca    18300
gagcaggagt tggctggttg tttcagcaaa gctgagaaca agcactggaa cttggggggct    18360 gaagacaggg agccacctaa gtacggtgaa ggcttcaagc acattggtgg gctccaggaa    18420
gctcatagcg atgggtctgg aggctcagaa acatggacac tgaattagga gcaaattggg    18480
atctgtgctg tgatcccatc ccatgcacaa ggaagcaaaa ggtgacaccc aatgtgttgg    18540
ccagaggacc ctgcttttaaa tacccaaaga tggtgcaaac ccagaaggct agtgacaggg    18600
tcttacaaca cagagtattt tttcctgtgc catgctaggt ggccatgatg tggaaggtga    18660
gaaaatgctg ggtcaggcac tgagcatctc taacctggtg tccccggtca gcggatagta    18720
ggaggcggag tctgtggagc tggcgttgga gtaagcgcct gaggtgcagt aattcaggcc    18780
aggaaagact tgcttgcaaa ctgaccagga ctgcctgttc tcaatgagag gtgggatcac    18840
ctccgttttg gtggtagaga ccaaatgtaa tgtgttgctg gtgaagaaca aaaatacctg    18900
agttattgcc aagtcatgaa tcaaaatgga catcacaaat tctcagggtg caaataccccc    18960 cttatcctcc tgtcttccct cagtccacac ctatctctaa ctatttaatt tactgagaaa    19020
caaataatat tagaaagaac atcaacatga caagccatga gagtgactct gaagcttctg    19080
gctgagttct ttccatctgt tacctgtaat ccccacaaca gtaggcttat ggttctcatt    19140
ttacagaagc agaggctcag agatgttaaa tagctgatca ctggggctga acttcagtgt    19200
gccccttcct tcctacaatg cagggcaaga gaaactgtct ctttcatatg aaatctccta    19260
ctctctacct gcttccttcc acctgcatta agcacgctca gtctcttcc cctgtgcccc    19320 tccccctatgc tcctttcttt cttttcttgc tttctcatct tcctcaccat caagagttgt    19380
ctgcctttgc agtctctact tcctcccaat gtgctctgac tgctcactcc atctcctgaa    19440
aatgctttca tcaatgtctc taatgccctc cttgctccta catccaatgg gcatatttag    19500
gtttcatctt ccttgacctc ccagaagcct tccatagagt tgcgcactca tgaccagact    19560
aagacgctgg agcctctcac atctgaagag atgatgcac cttccttcca agtgtgtact    19620
taaaaactta gtacatgtaa gaaagttcaa cattggcctg gttttttcta aggatgcttt    19680
ctttgaaata gcacattttc ctccaagtat tgtttctcca agttgggggt gccacaagac    19740
caagctttgc tgatgtgctg gagtcctaat gccagctttc gcctaccat ggggtgatct    19800 cccctgtggc tgctctttgg cttctgtgac cttttatggc tttggttctc cttctgcttc    19860
```

```
tctggtcact tcttctaact cattgctggt tattcccctt cttcctttat atgtttgtct   19920
tctccatatt tctgtcctca tctctcatgt ctcactctat accagttgct gtttaaccac   19980
aacaacctct gtatactaat gattcccaaa tccatatgtg gagcccaagc ctctttactg   20040
ggctcagatc cataggtcta tttgacagct agatttctaa actggttgtt tcataggagg   20100
acatcaaata cagcacatcc aaaactgaat ttgtcacttt ccttgaaacc agaagctctc   20160
ccactgtagt tcttattaaa atgaagggcg cctccttcct cttttcttct ttcttttgcc   20220
ttgtccccat acccagttaa tcacccagta cttatgattc tgcctcttag aaagttgtag   20280
aatctgctca ctcctttcta tacctggctt ttctccactg caggccatta tcagctctta   20340
gccacatagg atcgtaagag atgtccaatg gtctcttcgt gtccagctgt gcctccttct   20400
cacccatctt ccacactaga gtcagagtat ttcttctaaa acatcacccc tatcttattt   20460
ctgctcccct tttcaactcc tgtgccttca aaagagtcca aactccttag gatggctttc   20520
gcagctgggc atgctctctc ccctgcctac ctctccccat catctctgag ccccttacca   20580
ttctgcactt cttccagttc cttgaaccat attcctttac cttcaggcca ttacatgctt   20640
ttccttttgc ctggaacact cactcctttc tcctttgcct aaatgactct gacacagtcc   20700
tcagttatca ggtcaagtac acttgcttca gaatgcattc cctgactagc acaggctaca   20760
tgatataaaa tttcatggta ctctaatact ttctataact tagcccttac tctatgatta   20820
ctgcttgctt aattgtgtgt ctcccttata aaatgtaagc gttcaaaggt cagggacctt   20880
gtgtgtctca ctcaacatac gtggtatata ttaggcaatt aaatatacta tttttttgttt   20940
tttgtgagac aggatcttgc tctgtctccc aggctggagt gcagtggtgc aagcatggtt   21000
cactgaaggc ttgaactctt gggctcagtt gatcctccca tctcagcctt ctgagtagct   21060
ggagctacag gcatgtgcca ccacgactgg ctaattttgt tatttattta atttttttg    21120
tagagatggg gttttgccat gttgcccagg ctggtatcca acaccagggc tcaagcgat    21180
ccatccacct ggggctccca aagtgctagg attacaggca tgaaccaccg tggctggcca   21240
attaaatatt atttttgaat gaacacatga atgtgtctaa aatatgaaaa ctaaggcaaa   21300
tcaatggttg agggtgccac ttaaaatgga actctccaaa agaggctgta ttccattatc   21360
acgaggttag gagtttcatg ctttacctac ctagctacct caaatcaata tgttcttagg   21420
tatttttttgg gggggaaaat attaattttc caaagatgat ctctccagag ctattgtttc   21480
ttcattctca aaacaaatag ataacaaaaa atcacaactt aataaaaact aattaagcag   21540
taggtcttaa taagtctcaa agcagaaaga taaaggacag tttagtaaaa tgtgaaaagt   21600
agaagaaagg taattatgta gttatgtagt aagtctaggc tagaattaaa ataggtaacc   21660
cggaatcttt cctttctact cctctcctgc ttcctcagga cctgaatgat ctcaatcaac   21720
tgtttagcct ggcaaaattc tgcaggtaca ttctctgttc tctctttcaa actggctagg   21780
cagacttggc tgaaagaatt accctccact gagcagcttg actggtctct ttggggaagg   21840
aatgataaac ttcagcttcc cagcttttag ggcaacatga gcctccagac ccgactcgtg   21900
gaagaagttg gtgttcatct ggaccccact cctagcgaag tccggaatga tgatgcccat   21960
atttgtcaca aactccacag acacggaggg ttttgccacc agttcagcct gcatctataa   22020
gtcagaaaac aacctattca gattcattaa atacttcagt cccctgtcag tcagatcaac   22080
cacccttttct cacctccggg caaagatttc ctggataact cagacccttg gaaacattac   22140
tgggatttgt ttggaagaag gaaagcgagt tctcagttct ctagagttgg agtatactac   22200
```

```
ccagaactag aaagcacctg agttaacgtg aggcaaaacc agattaaaaa gatgatagga   22260
atactcattt gttgagagaa ctgagttctt gtcttatggc cataccacta ctggagctag   22320
tgaggtagtg cattctggtg gaagcttgaa gttttttcata aaaaaataat gaggtgatta   22380
caatgatgaa gcattttgtc ttgaagtgga aacacatttt taaatatgtt ttaacaagaa   22440
atgcaccctg gaagaaagta ataacctaag aaatcaaaag gcaaacagaa tcttacgttg   22500
gctacttcca gttttactcc agccttggct ccgggagcaa tgactccaga tgaagatatt   22560
tgcaactgta atccagctcc agtggggagt tcaaaggcat tctccatgaa gatgtagtga   22620 agaaaaagt cattctttga gcccttcctg atgacctctc caatctgtag acccaacaag   22680
ggagagcaaa taaagtaag tcttttaaa gtcggttttg ttaattacaa cctcccatac   22740
attggagagt aattcctctt tatctggaaa ggaaggacta gcatattttg atgagctgaa   22800
tagtttgata aataaagatc aaactgatgt ttttaccgtt ttcagtgaat caggatataa   22860
gaaatttcac tagatagata tcatgtcatt ttcaagtgga ctcagaaggc tcttaagaat   22920
attgctgggc ctcagagctt tatggacttt aagtatcata tatgccatgg cttaattctg   22980
gtgttctgga gtctgactgt aagtgaaggt gtacttgaaa tgtattatat tatgataaaa   23040 tcaattttt gaaaccaaag gcctattgag atgatgtaca tatcaatttg cattgggttt   23100 tatttttaa ataatatttc aataaaaatag cttgagacct gttttcttaa agtcaacatt   23160
tttttaatca agccatagga gtacatttat atatttcctt ttatgaatta ataataaaaa   23220
ttatagcata tttagatagt gaattatagt ttgccaaata ctttcttta taatcattgt   23280 atcatttcaa tcttaaaagg accttcaggt caggtgcagt ggctcacacc tgttattcca   23340
gcactgtggg aggcccaggc tggaggatca cttgaggtca ggagttcgaa accagcctga   23400
catggttgtc aacaggcttg tctctactaa agatacacaa attagccggg catgctggtg   23460
cacgtccaca gtcccagcta cttgggaggc tgaggcagga gaattgcttg aacccggaag   23520
gcagagttgc agtgagccga gattgtatca ctgcactcca gcctgggagc aagactccat   23580
ctcaaaaaat taaaaaaata aaaataaaaa taaaaggacc ttcagcaaag gtagaggaag   23640
gtataccgaa cattgttttc cagatgaata aattaatgct cttaaaaata cagctaacat   23700
tatgaatagc ttaatttcta aatgttaaca tttccatgtg atccaagagt catcttcagt   23760
gaaattcaag gcaaacctcc atctctgaag aaagtacaag catcttttcg ggcttgtgca   23820
gctgggatcg taagggagtc tgggcgatct aaaaaaaaac caacgtctgg tctcatgggc   23880
ccccagtggg gcctgctgac ttaccatctg ggggatcccc tgcagagtgc gggcacccat   23940
cagaagcagc tttcccagga gctggaggtc atggagactg gcaaaaccaa gctcctctcc   24000
caagatgcgg aggtaggctc tggcttccgg gacttctttg gatttcaaat cttaatcag   24060 cttctcaaca ctgagcatta ttccatttac catatcctga gagtttagta ataaaatggc   24120
cagtgagatg tcagcaatgt caaacacctt tcagttccca atgtgggacc tgtctgatgc   24180
agccaggatg ggcctaaaaa atgctccagg tgaggaacag ggagacactg aagtccaggc   24240
taattcctct aagcagagat taaagaacta aggtcttgtc agggatagtg gcactcctaa   24300
agctattctt aattaaaaaa tctgtagaca tagtaagatg tggtgggatg agaggagggg   24360
tccctattct ccagtatgcc aggatcctca agattagaag atcctctatc ccccacccgt   24420
tccctgctta gccttctctt ctttgaccag tgaagactac aaggtgtttc ttaagaaaat   24480
gtagctgtta tataaattca ccagaagttt gaaaacact tgatcctaga caagttcttc   24540
tcagagagaa gaagaatctc agagatggat gcccaggcat tgggaaaaaa aaaatgtgaa   24600
```

```
actgacagac tcaaagcaga tcaaagatcc tcggcctcaa gtgggggtca ggaaattaga   24660
agatggagct cgtgctcaac agtgagcctg gaggggtaaa ttactgcctt gctctgcaaa   24720
gttgaatgtg catacaagtc acatgaggtc ttgctaaaat gcgcttctga ttcagtagat   24780
tgtgggtgaa gcatgagaag ctgtatttct gaccagacca cactttgggt agcaaaaaat   24840
tcaagaataa gctccagatc atacaaccta tttccctcct taaatggggg ctcattgcta   24900
gcttcaaagt ggaagtttgg tctcatttgc tagtgcactg atgggagtga gagccaaaga   24960
cagcagttaa taataatgaa aatattaatt tagaactcgt aatagtgtct gcttattgaa   25020
caaccaatgc cagcatcagg cactgtgctt ggcattttag atgccttatt tcattgtctt   25080
taaataacct tgtgaggttt ggactgttat tagtagtctg ggatacagac agaaacagat   25140
acacataata tcaaccaact tccccaagtg cgcacagctt caagacaggg aagttagaat   25200
taaatctatg cccagagttc atactttttt ttttttttaag atacagtctc acactgtcac   25260
ccgggctgga gtgtaacggc gtgatctcgg ctcactgcaa cctccacctc ccgggttcaa   25320
gcaattctcc tgtctcagcc tcccgagtag ctaggattac aggcacccac taccatgccc   25380
agctagtttt tttgtatttt tagtagagac ggggtttcag tatgttggcc aggctggtct   25440
caaattcctg accttgtgat ctgcccacct tggcctccca aagtgctggg attacaggca   25500
tgaaccacca cacccagccc agagttcata ctcttgttat cctagagtac ttattgtgag   25560
tctggtttct gggcacactg aattcaggag atctttaact gcagaggata ctggccctta   25620
ccccagcagg tctggttgat aaaaaccata gttatccctt cagttagata gtattttgag   25680
gacttccatg cttagaaaag aattgttttt gcattgagac ccaaagcttt ccttaagaag   25740
atacttcaca aatacacacc tgctcatgtt tatcatcttt ggtatagcca aagtggtcca   25800
ctaagacctt agagacacca tcaggaactt gaccattaac ccagtacaaa gctttgttga   25860
cactgtctgg gaaaaatcct tgcttcccaa aaagagcttc caatgttggc tcaaagcctt   25920
ttccttccaa gccaatctga gaaagaaaat cagacaagaa aatggcatca ggtttctttg   25980
ttgtatgcca gcctagtagt ccccactctt gatgtccatt tatctaaaca gtatttgaa    26040 taccacaggc caggagctga ccttagcatt tcacaggagc tgcttttatta aaatctcact  26100 agaatcttga ccttattact tgctttttttc tagaagaggc agctaaggtt cagataggac   26160
aaataattca acaaaggatt cagagttggg agtgatttga gatttgaagc agatctgact   26220
aggcagcaca tatgcttcct tggctttggg acttaaagac gagacatttg catttcaatt   26280
tttttttttt tttttttttt tgagatggag tcttgctctg tcgcccaggc tggagcgcag   26340
tggcgcaatc tctcggctca ctgcaagctc agcctcctgg gttcacgcca ttctcctgcc   26400
tcatcctccc aagtagctgg gactacaggt gcctgccacc acgcccggct aattttttgt   26460 attttttagta gagatgggct ttcaccgtgt tagccaggat ggtgtcgata tcctgacctc   26520
atgatccacc cgcctcggcc tcccaaagtg ctgggattac aggagtgagc cacctcgcca   26580
ggcctgcatt tctattaatg ttaagaagtc atgcttcagg tgaccctag cggggagaga    26640 ggaaggcggg gaaggaggga aagaagaaag cctcagaatc atggtaggaa gtgcctggtg   26700
gttcttagtt ttcctctggg tagctcctgg ctcccaggga ctctctgttt atgatgctgt   26760
acaaaatggg ctagagaacc tcaaactctt cacacttacc tcgatgaggt cagctgaagc   26820
aaatccaaag gcagtgaggg tagttttcag catgctttct ttaggaaggt agttatttgg   26880
atcaaatata agattcccttt ctattttggc tgaggctggg tcaagtgatg gaagagaaac   26940
```

```
agatttgtag agttgatagt tccgagagaa ttttctgaag tccatgacag ttggaagttg   27000
agattctttc agagcttctt tcactaactt tttcagacta gataagaaga agtatatttt   27060
gagctgacac accatgttat tatcctttga ctcttgcacc ccaagtaaat atggatttcc   27120
aatcactacc aaaatgtctt gatttcattg accctaagtc tttgggtcta gatctgctac   27180
acatttgcac aagtgtttgt ttcagaagca agggcagaca gtggctatgc caaaacctag   27240
ggttggaatt ccagctcagg gccctcagtg gtatatgggg tgaatagctc ttacttactc   27300
ttggatatcc aattcttctg agttcaagat attggcaata tgggaagcca caaagttctt   27360
cacttgctca ttctgttccc atggtagaat ttggacaatt ttgttaatat ctgcctgtga   27420
aggactcctc atcaacataa gataggcagc cagtcgctta tctcccggag aagcatcatc   27480
aaggaaagtc tgaagaagaa cctcctggtc ctgcagtcaa agaggagat ggttatcact   27540 gtcctgtggt cagaacacag aacatgcctg gcaaacactg gcattgtctg ctagctcttt   27600
cttaagcaca ggtctaatt tctctgtaatc gttcttcaaa tgctggtatt gaatcttctt   27660
gccagtgttt cctagagcac tatcaagtaa gggttcccag aaaaagcctg tggaatgcct   27720
gttgaattca attccattaa aacacataaa ttatggccaa gttgtgattt gtttggagat   27780
ccaccactaa gtgaaaatca agttgtttta acgtaagtta ttttaatgtg aggataaaga   27840
tgagaagggg tagtaagagt ttggggctaa taaatagggt agtttccaaa gttctggagt   27900
ctttgcacct aagaggggc caagttggct atcctagcct aagcttattg ggggaaaatt   27960
aagcatgttt ttccatgatg agagggatgg tcaatctggt aggtggacgg taggaagcaa   28020
aaacatctca cgttctgcat gttgacatag cagcaaagtc aagtatttct ctcacgtcac   28080
atactgctag gcagtcaagt caataggctt gttgaaattt gcaattagaa aacagtagag   28140
gccaggtgca gtggctcacg cctgtaatcc cagcactttg caaggctgag gcaggcggat   28200
cacctgaggt caggagctca agaccagcct ggccaacatg gcaaaactcc atctctacta   28260
aaaaatacaa aaattagctg ggtgtaatgg cacatgcctg taatcccagt tactcaggag   28320
gctgaggcag agagaattgc ttgaacccag gaggcagaag ttgcagtgag ccgagatcat   28380
gccactgcac tccagcctgg gcaatagagt gagattccat ctcgaaagaa ggaaggaagg   28440
aaggaaagaa gaagggagg gagggaggaa ggaaggaagg aaggaaggaa ggaaaggaaa   28500
gaaacagcag aataaagtca gtagatgaaa tctagagtct cattcccta gtaccttcca   28560 aatccttgtt aataaacttt cactttcaga cctcttcttg tggactttac cttgtcttta   28620
ggctccattt tccgcagagc ctggatggca gctttctgga tcatcagtga tggctttgta   28680
ctttggacac atttcaggat tgaagacttg agttctggag ttaactgctc catggtttgg   28740
cccatatttc caatgacctg cattgaagaa aagaaacaag aacccatcag ggtgcaggag   28800
agggaagtaa aaggtgtcca ggaaaagtgc ttctgaaatg atgtatgtca tataaaagac   28860
tgagattacc cgcagaatca aataggtgta atcttcatcc ccagtgcagt catcttgaat   28920
ctgttccatc aggtaattag caatgtccag cagctcctgg gtccctgtag ggtttgtctt   28980
atgatagcta cagaataaga gaagagagtc aggacttggt aaccccagtt aggtttgtct   29040
taaaacccaa acttgtgaat tagaaaaaat aattataaaa ttcatatgga atccaaaaag   29100
agcctgaata gctgaagcaa ttttaagcaa aaagaacata gctggaggca tcacattacc   29160
tgacttcaga ttatacaaca aggctatagt aatctaaaca gcatggtact ggcataaaaa   29220
tagacacata gatcaatgga acagaatact gaacccagaa ataagtcac atacttacag   29280 tcaacggatc tttgacaaaa ttgacaaaaa catacactag ggaaaggaca ccctttcaa    29340
```

```
taagtggtgc tgggaaagat ggattgccat atgcagaaga ataaaactgg actcctatct    29400
gtcaccatat aaaaaaatca actcaagatg gatcaaagac ttaaatataa gacctgagac    29460
tataaaaatg caagaagaaa acctagggaa aacttctctg gacattggcc tagacaaaga    29520
attcgtgaat aagacctcaa aggcaaagac aacaaaaaca aaaatagac aaatagaact     29580 taattaaagt aaaaagtttc tgcacagtaa aacaaataat caacagggtg gtaacctgca    29640
gaatgggaga aaatatttgc aaactattca tccaatgggg tactaatatc cggaatgtac    29700
aagcaattca aacaactcaa caaaaaaatc ccccaaataa tcccattaaa aagtaggcaa    29760
aggacatgaa tagacatttt tttcaaaaga agacatacaa atggcaatag gcatatgaaa    29820
aaatgcataa cattactaat cattagagaa atgtaaatta aaaccacaat gagataacat    29880
cttacaagag tcaggagggc cattattcaa aagacaaaaa ataacagttg ttggtgagga    29940
tacagagaaa aggaaacagt taatcactgt tgatgggatt gtaaataagt acaaccacta    30000
tggaaaacaa tacagagatt tctcaaagaa ctaaaaatag aactaccaat aaatccaaca    30060
atcccattac tgggtatata cctaaaggaa aagaaatcat tatatccaaa ggaaacctgc    30120
acccatatgt ttatcacagc actattcaca atagcaaaga catggaatca acctaagtgt    30180
ctatcaatgg acgattggat taaaaatgtg aaatgtatag gcaataaaat actattcggc    30240
cataaaaaga ataaaatcat gtcatttgca gcaacatgga tggaactgga ggtcattgtc    30300
ttaagtgaaa caggacagtc acagaaagac aaatattgcg tgttgtcatt tataagtggg    30360
agtgaaataa tgtgcacaca aggacatagt gtgtggaatg atagacaatt gagactcaga    30420
aggtgtggaa gtggagggag atggatggtg agaaattact tagtgggtac actatatgtt    30480
gtctgggtga tggataccct gaaagccctg acttaactac tgcacaatct attcatgtaa    30540
caaaattaca cttgttccac ataaatttat ataaaaatgt aaaaagaaa aagccaaaaa     30600 atttcatcaa aggaaaaacc tgctagcctg agcaacatgg tgaaaccctg tatctaccaa    30660
gaatacaaaa attagccagg gcatggtagc atgcacctgt ggtcccagct actcaggagg    30720
ctgaggtggg aggatcactt cagcccagga atttgaggct tcagtgagcc gtgactgcat    30780
cactgcactc cagcctgggt gacacagtga gaccatctca aaaaaacaac aacaacaaaa    30840
aaaaacaaaa caaacaaaca aaaaaattca gaggaaaaaa ctgctaacta atattgaact    30900
gaagttaata atatgcaagc tgtaatactt aggggaaagt gtgttgatgt ttgcaattta    30960
ctttgaaatg cttcagaaaa taagatgaat taatggatgg atgtatatgt gataaagcaa    31020
atataataac acttaaatag taggagatag ctggttttct aggggttttc cctgtgaaat    31080
tctgtcaact ttgctatgtt caaaaacttt tataatataa tgtagagaaa atattttaa    31140 aaattcaatt tgtgtttgct gatttcttat ttcaagtcat tacccaaaa atgatcaaga    31200 aaaacacaa gagtaaggag cagagtttga aagtggaagg aggggttcag ttttaataca    31260
gagatgcaca gaggtgcaag atgttcctct gctcctagga ggagaaatac agtgtggaaa    31320
ctcacttgtt gaccgcgtgg ctcagcgcat acaaggtggc tcggctgcgc tgatccctcg    31380
ccatgttgaa gatctctcgc agctgctgtg ctgagggctc ggggatcagg gccaccaggt    31440
aggtgaccac atctatcaga aggggggtgg catgcacacg tttcagccac tggaggatgt    31500
gagtggagca ctgaggctgt ccacactgaa ccaaggcttg taaagtgatg gggctgagaa    31560
gaaagacatg gataaagtta tacagaccac cttcagggca cataaaatat tgctcatggt    31620
gtgtcctctg ccaggagagc ccttaatcac ctcattcact attcaaatct aacttcaaaa    31680
```

```
cccaacttgg agctcagaac catgatgctt tccttaggaa tattacccac agaagaagcc    31740
caatcgagaa aagttccaag aggggactgt ggatctgtag caacaagaag actgttatca    31800
cagtcctttg ccagcacac agaatatgcc tggccaacat tagctgggtc tcattcctgg    31860
cctcagtccc ttctctcacc ttcatagcac ttaaagccag tgccttgaag ggtagagaaa    31920
tcatattata ttttcgtct gagttctctc tccaccagcc tataagcttc tggagagcac    31980
ctgcaataga cctaggaatt aaaagttacc catcaaaatg tgggaactat tctccttctg    32040
ttttaacaca caaatacata gctgccttga acacagtatg cgcgtgtgtg tttcatggaa    32100
ctcagcgcag cagctgatag ttctctatcc agcaatcatg aactgattga ctaattgatt    32160
aactggattg atatccaaat ggtccctgag attctccatt tggccaaggt ttgaaagttc    32220
agtcagttac catcagtttt ataaaaagtt gagctgtaac cattagatac ctggacacct    32280
caatcagctg tggcaagaga gatgtgactg cttcatcact gaggcctctc agctcagtaa    32340
ccagcttatt gaagagatta gctctctgga tattttgctc agagatggtt agttttttca    32400
gttcctggag agtcttcaaa acagcttcgg cctgctttgg aggtgatgtg gatttggtgc    32460 tctcaaaatgc gaggcccatc ttcttagtac ctggaagatg gaaagtgtca aggaactct    32520 agctttcttc atctcaacca tatctttgtc tactggaagc tggaaattgt ggagtatcag    32580
cacaggggaa aagggaaaga aactatcctg tattcaatgc ctgctagatc tggctctgcc    32640
ataggtgatt gacttgtttt cactgactca tcatcctatc cctgtggggt ggcattattg    32700 ttcaattaa tgataaatc agccctgctt ctgagaccca cagagttttt gggccatgta    32760
aattgctcat ccctggatct cagctctgag tcccagagat gagacaaaga gatgagaccc    32820
agagatgagg aagtgtgacc cagagatgag caacttaggt ttcccaagag ctctcagggt    32880
ctaagaggta gagctaaagt ggaatccaga cttgtctgag tctatcatca ggttacccctt    32940 agcttgaaat aattggtgag gaggtgctac tgttgacatg gttacaactg gaccaggca    33000 catgggtgct tatcaccatt tcttctaatt gggtctacca gcagcttgtg gggaggggag    33060
acacttttgt atcctctcca ccacctactg tgacctatgc caggaagaga ggtaaaagtc    33120
atcatggaaa tgtggtgtaa tgagaatagt cctggcttag attacaacct ggcacttatt    33180 ttccccctc taatattctg cggccttgac tacatcaaac tctaagcctc tctgtgtcac    33240
tgtctcctct gtagaatagg tataaaatca catctctacc acctgacatc acaggttgct    33300
atgagcaaaa aggacaatga ggtaatgtac aagaaggaat ttggacagat ataaatacaa    33360
tacaatactg ggtaagggtt ggacttgaga ttgttagagt tccttctacc tctaaagact    33420
gactcctgag gttactatct ggccagactc tgaaggttct ctcccacttg gtccacctcg    33480
tctgggacag ctctggatct tatcacagga tgggtgatgt cagttctatc aaatatgtca    33540
tgttaaactt aggattccag ttttctattt acaaatgcct aagtagcttt gggaacttct    33600 ttcctttat gccattgcaa cttgacatca tgaaatgagt ttgctttctc actagaggta    33660
gccagaacac cagtgtctgt atcacttgtt agtcagcaga catttaacag ggctcagcaa    33720
gtggctaagc catgataggc acatcttgag tagattttcc agcaactatg tggacagaaa    33780
ctcttacctt caccaaagaa gcggctgttg atctttggtg tgtcttcaag tttcaaagtc    33840
tgtgtcactt gtgctaccat cccatactta ttcctggtaa ccaaggaagc acaccatgtc    33900
acggatggcc agaacatact attctttcca tgttgaaggt tttccctgtc tctgcatcta    33960 cccagtcct gcccatcttt caaagcatgg gtaaatccag ccattgttgg ccctgaatga    34020
ataacatcca cctcttcctg gtcacgctag ttatcctccc atcaaaaaga catgcgtgcc    34080
```

```
ttatactctc cactagtctg gagtggccag aggtaggaac tagtgcaatg tctcaaaatt    34140
ctttcgtatc ttccacaaca tagagccaag aatatggcag ttactcaata tatattcatt    34200
gattatcagt tttcaaagtg gatttggata cacaagtttc cagtcagtat cccaaatctt    34260
ccatgaaacc ttttctaacc agggtaccct gcagtgatcc tcaggttttc tggatctaca    34320
gcccttaaag aatgggtctt agatatcttt tgttggtctt ggattgtttt gcatgcctag    34380
gacttttctg ccaaatggcc tgttcgctta aaaggggga cagggagggg cggcatttta     34440
tccctctcca ttcctccctc ccaggcacag gtttgcctgg aacagagcac ttgagaagtg    34500
ttcagttcac actgacccat taaatgacaa atcaggggtg catcacatga cctacttgta    34560
ggagaaaggc aggaagaggt gttgctcctt gcagatggct tctgccacat gcttcctctt    34620
agcgtccagt gtgtactgac aggactggct gctgctgatc agagttgaca aggggcgggt    34680
ctatgaaaga gattggagac gagcattttg atcagtccct gtatcttctg ttaaaagcat    34740
ttaccttcaa ggtagaaggg agcaggagtc ctgtaccact agataaactc agagaaagaa    34800
gataactggg tacttgacat ttagaccagg gggtgcaaca agtcggcatc cccaaagctg    34860
agtcaagctg tagactcctc ttttttccacc ctcactggac aatgtctaaa ctttgtatcc   34920
tccacatgcc catcccacca catagcccct cacacacctg ctcagtaact tttctttgcc    34980
caaaagccca ttcttacatg tctctttcat ttacatattc tttgcatttt ttgggttcct    35040
gctccacatc ttccatgaaa tgttgcccgc tgagctacat gaataattct ttctccttcc    35100
tggtcaggcc caggacttct tgtctgcact gttcagctta tcaccttatt gagtatacca    35160
cgtatacttt attgacctgg ctcctgcatt agactggaag catcctgagg ggaaggtcca    35220
tggttcatct gccactgtcc cttccttggt gctgcccaga gtggggttga gcaaacagca    35280
gatgctcaga aaagacccct aagccagtgc attatcctct tctgactgtg gcactcatgg    35340
tcatcagact ccctgttttc aaccctaagg acaatgacca ggaacagcgc ccagcatgac    35400
agtgattgcc caagttattc atgttcactg agacaggctg gggctcatat cagggaagat    35460
gttgcagggg tcaggcaggc tcaggtaata tggtgctcca tggccccagt taacagagag    35520
gagagggtgc tccaggccgg tggcagtggg gccatgtttg gtcagggtgg tactgggggt    35580
ggaaggacaa gaagctggag cactctaagt cactccactt catgggatga gggagagggg    35640
gagaacacag gtcttgggac ttcttcaaag gccagaggct tggagctggc acaaggagtc    35700
cttgtgcaga aaagaacaga aggtggtttt gctgccctac atccatcccc ggaaccttct    35760
cagaggtgag tagtcattac tctcaagtga tgagattaga ggcagtttgg tgccagtgac    35820
agaaggacag gaggaaagac agagctctgg gctgggaggg aggagcctga ctcaagcctt    35880
ggctcaactg atcccaggcc gtgaagcctg gcagaccttt cccgtgcctg ctcagggtcc    35940
tatctctagt ctgtataaaa aacagccagg gcaggctgtc ctcaaaggtg cccactagct    36000
caaaagttct ggaattgtat taataagagg atgctccttg ctgtgcacga cagtgctgac    36060
atgggactta ccatgccttt gatgagagca agtgggctga tgcctgtgcg gatgggcttg    36120
aagcgatcac actgccccag gtctctttca gtggatattt ctgttgccac attgcccttc    36180
ctcgtcttga cggtaaagtg agtggagcag tttccataca cggtatccta tggaggaaga    36240
agatgcaacc acatgtattc aacacgggca acatccttgg gtacttggga gggatggggt    36300
ggggatcgtg aaagaaaaag cagaaggaat ctagctttgg gagggacttt ctttttcttc    36360
ctatgcagag tgtggtcttg ctagtgcctg gccagcccaa gttgggagag agaaaaccag    36420
```

```
ttaaaggtgg gtctgcagaa aggcctccgc aggttgcatc ggtgtcttct cccattatgg    36480
tgtcgtagag aaattagaac acacaaaagt gctcatggga ctgaggtgaa atgaattctg    36540
tctcacagtg aaacctgaaa ttcgtaaaag agaccagcaa cagatcccat tattttggt    36600 gtttaaaata cacacaggat ttactgtgta caccataacc cagcaaacac aggtgaagca    36660
tcaaacaaaa gcaggggtgg ggtggccagg actcctcaat gactgtttta aaattagacc    36720
caacctgata agcctgcttg ggatgatctg tcagtgagcc taaggggcag gaggaacctc    36780
gggcaccagt atttcacgcc aatccagggc ttcctatgta actagtcatg gagctgactc    36840
agtgatctgc tttgtatatg gtaggactgg tctctaacac atgaagatga gtttcaaggg    36900
ccactgctat cagcttttcta aatcctcacc agaaacaaca cttgcttggc ttcttctgtc    36960
tctgggggaa ccaggagggc agaaatgatg cccctcttga tgttcaggat gtaagtaggt    37020 tcatcttttct ccgggtaaag gaaaacctgc ttcccttctg gaatggccag cttgagctca    37080
tacctgtccc agagagagga tggtcacgga aatgtccttc tccattacaa cttgctggaa    37140
gtaagctggg tggcactgaa gttttctttct tcatattttt ttaaccaatt gttcttctga    37200
catcatttat ttgtaaatat agaatatagc tacacataga catacatttt caaaaaagta    37260
tgcacatata cataagtttt ggtgattctt tttttttctt tttttctttt ttcttttttct    37320 ttttttgaaa tggagtctcg ctcggtcgcc cgggctggag tgcaatggcg caacctcagc    37380
tcactgcaac ctccacctcc tgggatcaag tgattctcct gcctcagcct ccggagtagc    37440
taggactact ggcatgtgcc atcacaccca gctaattttt gtattttttag tagagacagt    37500 tttcaccatg ttggccaggc tggtctcaaa ctcctgacct caggtgattc tccctcctcg    37560
gcctcccaaa gtgctgggac tacaggcatg agccaccagg tccagctgtg ttttaactttt    37620 ttttgcttgg ctcatccagc cctgctctgt tctccaccca tatcagtctc tttgcccatc    37680
ctccccatac ggacacccga gtggttgttc catttgtttc tgcacactca tacaatcctc    37740
tgtaaacatg ggtgagtgca aacagagtca tacaaagatt ttgccattgt ttgttttata    37800
caagtggcat tgtattatgc atactttttat cttgttttttc tcacttaatt atacttcaca    37860
aaaatccttc tgagtcactt ggtacagctc taacagattt ttttaaaagc tgcatgcaga    37920
acattccatt ccatggctaa atataattta ttcacacatt gccccatttg atggcatttg    37980
ccctctctct ttctggattt ttttttaaacc acacaaacaa taccaaaaca acatcccttta    38040 tgtgcctatc ttcacacatt actgctttta ttttcatggg ctagagtccc aaagactaaa    38100
atatctgtgt caaagggtat taagtatttt aaattacagt agatattgcc tgatggctct    38160
cgtttccacc agcagctcag gacagcacac ttttcctcac tggcctgcca gcaacaggtg    38220
ctatcactgt ttttccagttt tgcagtatga tgggtaaaag cagataaata tcttgttgtt    38280
acattaattc gcatttcttg actaccagtg aattggagct tattttcata cacttgttgg    38340
acagtcattc ttttgtatgg tgtcaggcca tggctgaagc ccatgctgac tttggtctta    38400
gggatttccc actgggtact ctctgagttt ctgaggacct ggctgcagcc actctggtta    38460
catcaggagg aaaaggtgac ggacttatct cccacagcct acactctctc agaaagttcc    38520
caacacgaag aaatgataaa tgtttgagat gatgggtatg ctaattactc tgatctgatc    38580
accatacatt acatgtatca aaatatcact atgttctcaa taaatatgta taattattgt    38640
atgtcaattt ttaaaaaaga cagttaaagt catgaagatg caaacatgga aagccctcct    38700
tttcaagaac aggagtctct tctgtatttg gagaagacca aggaccaaaa aataaaccac    38760 tcttttcctcc tgccaccata cccctctccc tcatatacag ttaagtcttg gagaaaataa    38820
```

```
agcataggaa agaaagaagc ctcacagcct attttggcaa gaaaggactg gcatctgaat    38880
ctaatgttta gcaaaactga aaatgggca aggatggtga tatggtttgg ctctgcgtcc    38940
ccacccaaat ttcgtctcgt agctctcata attcccacgt gttgtgggag ggacccgggg    39000
ggaggtgatt gaatcatggg ggcaggtctt tcccgtgctg ttctcgtgat tgcagatggg    39060
tgtcgggaga tctgatggtt ctaaaaacag gagtttctct gcacaagctc tctttgccag    39120
ccaccatcta cataagatgt gacttgctgt ccctcacctt ccgccatgat tgtgagacct    39180
ccccagccac gtggaactgt gagtccaata aacctttctt ttgtaaattg cccagtctca    39240
ggtatgtctt tatcagcagc atgaaaacag actaatacag acagagtttt ctgatgctac    39300
caagttaaca actctatcct gcctgtattc atacacacct aggaccctac aaactgtgat    39360
tgaggatgag gcaggggtga tgttgaaaat atttacaatg ggtgcgacat gggccctgac    39420
cagtcagcag agatgcagct gcagtggccg atcagcgtgc agtggctgaa tgccagccta    39480
ggagggggag ccaccgaagc cttggtgctc ctctgccctg cggtgaacag accctgcccc    39540
gccatgtgcc ggccacagca gccagtgcct ctgggacccc acaccaaaga ccaccaagca    39600
ctagtcttga ctagttcttt aaataagaat tcacttgttt aaacaaagca tctcagtttt    39660
ataatctcaa gaagtttaaa gcatgagatt tttagaaaca catgaaaatg ataattaaag    39720
gaacctaact agggaaggtt aactaatgct tctctctttt tgatgattgt gaaaactcag    39780
taattccctg atccacgatg gatacggaat acaaatactt acagtcacat ccgtgcctgg    39840
tgcaaacaca caagttcata cctcagcgga cacacacaca tgcgtgtgct catgtacaac    39900
atgacttacc tggacatggc tgcagcaaac tcctcagagt tcttggtttt cttcagcaag    39960
gctttgccct cagggttgaa gccatacacc tctttcaggg tgcactggct ggtcttcagg    40020
atgaagctgc agagctgggg aacctccagc tcaacctgag aattcagggt agcagagcat    40080
tgaggttgtc tatcaagaat gagaggtggc ccctgaagcc cagggcttaa tctctaatca    40140
gagcaccaaa gggaatggtg ctgggaacac cactgcctgc gcctcaacac cacatgcctt    40200
atcaacatgc ctcctgggtt ctctgtgcac caacctagac ttagtcctat tgctgacgtt    40260
ttcccctcc cgggtaacac atttcttaag tttgccccta ggcatgggaa ggaggatgtc    40320
cttttattgg ttctaaagtt actcactta attataaga gctgtggtta aatagaagcg    40380
ctgcagacta ggagtgaaag tgaagaagaa aaacagaaag caggaagagg gccatccttc    40440
gtttccacag caaatgtctc cttaatgtca cccaaaaaac tggttatatc tattagggcc    40500
tatttagagc tttgcatata gctggagttt caacggattc ctacttatta tccagcacta    40560
ttcaaataac tttatagaaa tgttgtacat gtgtgctgtt caatatggga gccagtagcc    40620
agggtggctg ttgagcagtt gaaatgcagc taatgtgaca acgaatatga attttaatt    40680
tcattccatt taaatagccc aatgtggctc atgtctacca tattggacag cacatacaag    40740
agctacggta ctctctaaaa aaaggtgact gctcagcttg acttctcttc cccacccaaa    40800
ccccaatagc agcctgtaga tctgctccac atgtatgtaa catgagtaca accagtctca    40860
ataataagca aagtttttatt ttagaacaaa ctgtatgttt atatttttt cttctttcca    40920
ttcattttc agcaacagat tctgtttgac ttaaattata aaaactgcat ttcacagtgc    40980
gattccgagt tgcctgcctc ccatagctca cctactgggc ctctctcacg ctgaaatcta    41040
cagacccaca ctgctgctaa tctagatcat ggattcctat tgcatctggg aagttaacgg    41100
gaaaatactt ctgacttgcg aaatttggtg ggggcagacc acatctcagc aatgtggctg    41160
```

```
acttacaaac agaggcaaag tcccagtgct tgatcagat tacaacagtt ctgggatgtt    41220
ctgcgtttgc tcagtacaca ccctccggga aggtcgcgtg ttgggcgccc gctggaacag    41280
ggctggggga aagctgtggg ctctaggtcc ctcctgcctg catcctccat accttgcagt    41340
tgatcctggt ggcacttctt gaatcagcag tcccagggac tccactggaa ctctcagcct    41400
catagttgta tgtgtacttc cggaggtgct tgaatcgggt cgcatcttct aacgtgggga    41460
gaaatacgtc agccacatag cagaaatagc tctcccaagg acagccaatt ctgggcagag    41520
aggggcagtg gcatagagaa ttaaaaatgg taattcaact caaattattt tttaattgac    41580
tttatactta attttccttt atagatttga cttctccatt atgttttgc tgaggctaat     41640
gtttaaattg gctggcatgt cttgaatatc tcatctgagg cacagggaag ggagtgacaa    41700
gtgtcaagta atggggctca gaaaatctgc atgagagacc ctctggcaaa ttaagagatg    41760
acaacattac gcaaatagta ctatctctaa tgcttttta gcttgaacac gccgtaattc      41820
cgtgactcta agactaccaa atacttaagg caaagttcat taagcattaa gcgtaactaa    41880
cttaacaaac tcctagaaaa gaattctgg aggtttccac tgtagttgag aggaattttc      41940
tgaacaattg aagaaaaaga acatctgggt cctgagtcca gctgcagtga tgacagacgg    42000
ccactagatg gcggtgctgc cccatcagaa gtccgccccg cggctccagc acacagggtc    42060
gcgcttggag gccagttcct ttaaccccca ggggtcaggt aaataggaag ggggtggagg    42120
ttcgatttct tcacaaaggt taaagtcagt atttcctcac cctcacatgc ttcgaatcaa    42180
tgactagtca ctgataaaca ggacagtgat gtttcttcaa agtgtgcaca ggccagcgga    42240
gagacaatcc cttccctccc ccgcccccag gctgaacttt tgggacagaa cagaaggcca    42300
ggtagaagag agttggcatc ccttgggtgt gggcagaggc tcaggggaact tgcttcctgg    42360
ggtcagagca aggcacacca cgatgccatc tcagccctgt agagtgggag ccctcaggg     42420
acccgggtgt aggagagtgc acggggctgg gcgcccttcc acgccccatg cgcagatgcc    42480
ttacttggac agaccaggct gacattttcc agcatttcct cttctgtaag acaggagaaa    42540
gaaatctgtg agcttcccac gtcttcccag cgggtgctag ggcccgacag ggggaccacc    42600
ggcacaggtt tcacctttca ggagggaggc aggctccgga ccccctcc tcagcccctc       42660
catcccgcgc ccccatcct gagcctgcag gggccgccag ctggtccaat ccccccactc      42720
gccctggacc ctgtggctgc cctccctctg gcctaggccc aggctgcccc ggccaacctc    42780
gtgccgccgg ctccctcccg ctccctctgc gcccgcagag cggccgcgca tcaccggcc      42840
ctggcgcccg ccagcagcag cagcagcagc gcaggcagcg ccagcagcgc cagcagcgcg    42900
ggcctcggcg ggtccatcgc cagctgcggt ggggcggctc ctgggctgcg gcctggcctc    42960
ggcctcgcgg ccctggctgg ctgggcggcc tcctcagcgg cagcaaccga gaagggcact    43020
cagccccgca ggtcccggtg ggaatgcgcg gccggcgccc gcaccccatt tataggaagc    43080
ccaggctgca agagcgccag gattgcaaaa ggtccaaagg gcgcctcccg ggcctgacct    43140
gtttgctttt ctacactggc ttctctttga gccttgaaga gcctcgggga gggggcccac    43200
ctgggatgca gccgcagcca ccaggggctg ggtcccaggt gggttccctt ccccaagcgt    43260
cttcagtgct ctgcgcggc ccttcctgtg tctcagtggg gccatggcca gcgcctcagg     43320
gtctgagaag cctgccctga ccaggggtgc cttcttcaga tgacccacca tggggacaaa    43380
atctctgctt ctcctggact gaattgggag ccacgaggag aaccagtcct gagcgctgtc    43440
ttggt                                                                43445
```

```
<210> SEQ ID NO 3
<211> LENGTH: 19
<212> TYPE: RNA
<213> ORGANISM: Artificial Sequence
<220> FEATURE:
<223> OTHER INFORMATION: Antisense Oligonucleotide

<400> SEQUENCE: 3
cgagaggcgg acgggaccg                                                  19

<210> SEQ ID NO 4
<211> LENGTH: 19
<212> TYPE: RNA
<213> ORGANISM: Artificial Sequence
<220> FEATURE:
<223> OTHER INFORMATION: Antisense Oligonucleotide

<400> SEQUENCE: 4
gcucuccgcc ugcccuggc                                                  19

<210> SEQ ID NO 5
<211> LENGTH: 21
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: misc_feature
<222> LOCATION: (1)...(19)
<223> OTHER INFORMATION: bases at these positions are RNA

<400> SEQUENCE: 5
cgagaggcgg acgggaccgt t                                               21

<210> SEQ ID NO 6
<211> LENGTH: 21
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: misc_feature
<222> LOCATION: (3)...(21)
<223> OTHER INFORMATION: bases at these positions are RNA

<400> SEQUENCE: 6
ttgcucuccg ccugcccugg c                                               21

<210> SEQ ID NO 7
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 7
tccgtcatcg ctcctcaggg                                                 20

<210> SEQ ID NO 8
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 8
gtgcgcgcga gcccgaaatc                                                 20
```

<210> SEQ ID NO 9
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 9
atgcattctg cccccaagga                                          20

<210> SEQ ID NO 10
<211> LENGTH: 14121
<212> TYPE: DNA
<213> ORGANISM: H. sapiens

<400> SEQUENCE: 10

```
attcccaccg ggacctgcgg ggctgagtgc ccttctcggt tgctgccgct gaggagcccg    60
cccagccagc cagggccgcg aggccgaggc caggccgcag cccaggagcc gccccaccgc   120
agctggcgat ggacccgccg aggcccgcgc tgctggcgct gctggcgctg cctgcgctgc   180
tgctgctgct gctggcgggc gccagggccg aagaggaaat gctggaaaat gtcagcctgg   240
tctgtccaaa agatgcgacc cgattcaagc acctccggaa gtacacatac aactatgagg   300
ctgagagttc cagtggagtc cctgggactg ctgattcaag aagtgccacc aggatcaact   360
gcaaggttga gctggaggtt ccccagctct gcagcttcat cctgaagacc agccagtgca   420
ccctgaaaga ggtgtatggc ttcaaccctg agggcaaagc cttgctgaag aaaaccaaga   480
actctgagga gtttgctgca gccatgtcca ggtatgagct caagctggcc attccagaag   540
ggaagcaggt tttcctttac ccggagaaag atgaacctac ttacatcctg aacatcaaga   600
ggggcatcat ttctgccctc ctggttcccc cagagacaga agaagccaag caagtgttgt   660
ttctggatac cgtgtatgga aactgctcca ctcactttac cgtcaagacg aggaagggca   720
atgtggcaac agaaatatcc actgaaagag acctggggca gtgtgatcgc ttcaagccca   780
tccgcacagg catcagccca cttgctctca tcaaaggcat gacccgcccc ttgtcaactc   840
tgatcagcag cagccagtcc tgtcagtaca cactggacgc taagaggaag catgtggcag   900
aagccatctg caaggagcaa caccctcttc ctgcctttct ctacaacaat aagtatggga   960
tggtagcaca agtgacacag actttgaaac ttgaagacac accaaagatc aacagccgct  1020
tctttggtga aggtactaag aagatgggcc tcgcatttga gagcaccaaa tccacatcac  1080
ctccaaagca ggccgaagct gttttgaaga ctctccagga actgaaaaaa ctaaccatct  1140
ctgagcaaaa tatccagaga gctaatctct tcaataagct ggttactgag ctgagaggcc  1200
tcagtgatga agcagtcaca tctctcttgc cacagctgat tgaggtgtcc agccccatca  1260
ctttacaagc cttggttcag tgtggacagc ctcagtgctc cactcacatc ctccagtggc  1320
tgaaacgtgt gcatgccaac ccccttctga tagatgtggt cacctacctg gtggccctga  1380
tccccgagcc ctcagcacag cagctgcgag agatcttcaa catggcgagg gatcagcgca  1440
gccgagccac cttgtatgcg ctgagccacg cggtcaacaa ctatcataag acaaacccta  1500
cagggaccca ggagctgctg acattgctaa ttacctgat ggaacagatt caagatgact  1560
gcactgggga tgaagattac acctatttga ttctgcgggt cattggaaat atgggccaaa  1620
ccatggagca gttaactcca gaactcaagt cttcaatcct caaatgtgtc caaagtacaa  1680
agccatcact gatgatccag aaagctgcca tccaggctct gcggaaaatg gagcctaaag  1740
acaaggacca ggaggttctt cttcagactt tccttgatga tgcttctccg ggagataagc  1800
```

```
gactggctgc ctatcttatg ttgatgagga gtccttcaca ggcagatatt aacaaaattg    1860
tccaaattct accatgggaa cagaatgagc aagtgaagaa ctttgtggct tcccatattg    1920
ccaatatctt gaactcagaa gaattggata tccaagatct gaaaaagtta gtgaaagaag    1980
ctctgaaaga atctcaactt ccaactgtca tggacttcag aaaattctct cggaactatc    2040
aactctacaa atctgtttct cttccatcac ttgacccagc ctcagccaaa atagaaggga    2100
atcttatatt tgatccaaat aactaccttc ctaaagaaag catgctgaaa actaccctca    2160
ctgcctttgg atttgcttca gctgacctca tcgagattgg cttggaagga aaaggctttg    2220
agccaacatt ggaagctctt tttgggaagc aaggattttt cccagacagt gtcaacaaag    2280
ctttgtactg ggttaatggt caagttcctg atggtgtctc taaggtctta gtggaccact    2340
ttggctatac caaagatgat aaacatgagc aggatatggt aaatggaata atgctcagtg    2400
ttgagaagct gattaaagat ttgaaatcca agaagtccc ggaagccaga gcctacctcc    2460
gcatcttggg agaggagctt ggttttgcca gtctccatga cctccagctc ctgggaaagc    2520
tgcttctgat gggtgcccgc actctgcagg ggatccccca gatgattgga gaggtcatca    2580
ggaagggctc aaagaatgac ttttttcttc actacatctt catggagaat gcctttgaac    2640
tccccactgg agctggatta cagttgcaaa tatcttcatc tggagtcatt gctcccggag    2700
ccaaggctgg agtaaaactg gaagtagcca acatgcaggc tgaactggtg gcaaaaccct    2760
ccgtgtctgt ggagtttgtg acaaatatgg gcatcatcat tccggacttc gctaggagtg    2820
gggtccagat gaacaccaac ttcttccacg agtcgggtct ggaggctcat gttgccctaa    2880
aagctgggaa gctgaagttt atcattcctt ccccaaagag accagtcaag ctgctcagtg    2940
gaggcaacac attacatttg gtctctacca ccaaaacgga ggtgatccca cctctcattg    3000
agaacaggca gtcctggtca gtttgcaagc aagtctttcc tggcctgaat tactgcacct    3060
caggcgctta ctccaacgcc agctccacag actccgcctc ctactatccg ctgaccgggg    3120
acaccagatt agagctggaa ctgaggccta caggagagat tgagcagtat tctgtcagcg    3180
caacctatga gctccagaga gaggacagag ccttggtgga taccctgaag tttgtaactc    3240
aagcagaagg tgcgaagcag actgaggcta ccatgacatt caaatataat cggcagagta    3300
tgaccttgtc cagtgaagtc caaattccgg attttgatgt tgacctcgga acaatcctca    3360
gagttaatga tgaatctact gagggcaaaa cgtcttacag actcaccctg acattcaga    3420 acaagaaaat tactgaggtc gccctcatgg gccacctaag ttgtgacaca aaggaagaaa    3480
gaaaaatcaa gggtgttatt tccatacccc gtttgcaagc agaagccaga agtgagatcc    3540
tcgcccactg gtcgcctgcc aaactgcttc tccaaatgga ctcatctgct acagcttatg    3600
gctccacagt ttccaagagg gtggcatggc attatgatga agagaagatt gaatttgaat    3660
ggaacacagg caccaatgta gataccaaaa aaatgacttc caatttccct gtggatctct    3720
ccgattatcc taagagcttg catatgtatg ctaatagact cctggatcac agagtccctg    3780
aaacagacat gactttccgg cacgtgggtt ccaaattaat agttgcaatg agctcatggc    3840
ttcagaaggc atctgggagt cttccttata cccagacttt gcaagaccac ctcaatagcc    3900
tgaaggagtt caacctccag aacatgggat tgccagactt ccacatccca gaaaacctct    3960
tcttaaaaag cgatggccgg gtcaaatata ccttgaacaa gaacagtttg aaaattgaga    4020 ttccttttgcc ttttggtggc aaaatcctcca gagatctaaa gatgttagag actgttagga    4080
caccagccct ccacttcaag tctgtgggat tccatctgcc atctcgagag ttccaagtcc    4140
```

```
ctacttttac cattcccaag ttgtatcaac tgcaagtgcc tctcctgggt gttctagacc    4200
tctccacgaa tgtctacagc aacttgtaca actggtccgc ctcctacagt ggtggcaaca    4260
ccagcacaga ccatttcagc cttcgggctc gttaccacat gaaggctgac tctgtggttg    4320
acctgctttc ctacaatgtg caaggatctg agaaacaac atatgaccac aagaatacgt     4380
tcacactatc atgtgatggg tctctacgcc acaaatttct agattcgaat atcaaattca    4440
gtcatgtaga aaaacttgga aacaacccag tctcaaaagg tttactaata ttcgatgcat    4500
ctagttcctg gggaccacag atgtctgctt cagttcattt ggactccaaa agaaacagc     4560
atttgtttgt caagaagtc aagattgatg ggcagttcag agtctcttcg ttctatgcta     4620
aaggcacata tggcctgtct tgtcagaggg atcctaacac tggccggctc aatggagagt    4680
ccaacctgag gtttaactcc tcctacctcc aaggcaccaa ccagataaca ggaagatatg    4740
aagatggaac cctctccctc acctccacct ctgatctgca aagtggcatc attaaaaata    4800
ctgcttccct aaagtatgag aactacgagc tgactttaaa atctgacacc aatgggaagt    4860
ataagaactt tgccacttct aacaagatgg atatgacctt ctctaagcaa aatgcactgc    4920
tgcgttctga atatcaggct gattacgagt cattgaggtt cttcagcctg ctttctggat    4980
cactaaattc ccatggtctt gagttaaatg ctgcatctct aggcactgac aaaattaata    5040
gtggtgctca caaggcgaca ctaaggattg gccaagatgg aatatctacc agtgcaacga    5100
ccaacttgaa gtgtagtctc ctggtgctgg agaatgagct gaatgcagag cttggcctct    5160
ctggggcatc tatgaaatta acaacaaatg gccgcttcag ggaacacaat gcaaaattca    5220
gtctggatgg gaaagccgcc ctcacagagc tatcactggg aagtgcttat caggccatga    5280
ttctgggtgt cgacagcaaa aacattttca acttcaaggt cagtcaagaa ggacttaagc    5340
tctcaaatga catgatgggc tcatatgctg aaatgaaatt tgaccacaca aacagtctga    5400
acattgcagg cttatcactg gacttctctt caaaacttga caacatttac agctctgaca    5460
agttttataa gcaaactgtt aatttacagc tacagcccta ttctctggta actactttaa    5520
acagtgacct gaaatacaat gctctggatc tcaccaacaa tgggaaacta cggctagaac    5580
ccctgaagct gcatgtggct ggtaacctaa aaggagccta ccaaaataat gaaataaaac    5640
acatctatgc catctcttct gctgccttat cagcaagcta taaagcagac actgttgcta    5700
aggttcaggt tgtggagttt agccatcggc tcaacacaga catcgctggg ctggcttcag    5760
ccattgacat gagcacaaac tataattcag actcactgca tttcagcaat gtcttccgtt    5820
ctgtaatggc cccgttttacc atgaccatcg atgcacatac aaatggcaat gggaaactcg    5880
ctctctgggg agaacatact gggcagctgt atagcaaatt cctgttgaaa gcagaacctc    5940
tggcatttac tttctctcat gattacaaag gctccacaag tcatcatctc gtgtctagga    6000
aaagcatcag tgcagctctt gaacacaaag tcagtgccct gcttactcca gctgagcaga    6060
caggcacctg gaaactcaag acccaattta acaacaatga atacagccag gacttggatg    6120
cttacaacac taaagataaa attggcgtgg agcttactgg acgaactctg ctgacctaa     6180
ctctactaga ctccccaatt aaagtgccac ttttactcag tgagcccatc aatatcattg    6240
atgcttttaga gatgagagat gccgttgaga agccccaaga atttacaatt gttgcttttg    6300
taaagtatga taaaaaccaa gatgttcact ccattaacct cccattttttt gagaccttgc    6360
aagaatattt tgagaggaat cgacaaacca ttatagttgt agtggaaaac gtacagagaa    6420
acctgaagca catcaatatt gatcaatttg taagaaaata cagagcagcc ctgggaaaac    6480
tcccacagca agctaatgat tatctgaatt cattcaattg ggagagacaa gtttcacatg    6540
```

```
ccaaggagaa actgactgct ctcacaaaaa agtatagaat tacagaaaat gatatacaaa   6600
ttgcattaga tgatgccaaa atcaacttta atgaaaaact atctcaactg cagacatata   6660
tgatacaatt tgatcagtat attaaagata gttatgattt acatgatttg aaaatagcta   6720
ttgctaatat tattgatgaa atcattgaaa aattaaaaag tcttgatgag cactatcata   6780
tccgtgtaaa tttagtaaaa acaatccatg atctacattt gtttattgaa aatattgatt   6840
ttaacaaaag tggaagtagt actgcatcct ggattcaaaa tgtggatact aagtaccaaa   6900
tcagaatcca gatacaagaa aaactgcagc agcttaagag acacatacag aatatagaca   6960
tccagcacct agctggaaag ttaaaacaac acattgaggc tatttgatgtt agagtgcttt   7020 tagatcaatt gggaactaca atttcatttg aaagaataaa tgatgttctt gagcatgtca   7080
aacactttgt tataaatctt attggggatt ttgaagtagc tgagaaaatc aatgccttca   7140
gagccaaagt ccatgagtta atcgagaggt atgaagtaga ccaacaaatc caggttttaa   7200
tggataaatt agtagagttg acccaccaat acaagttgaa ggagactatt cagaagctaa   7260
gcaatgtcct acaacaagtt aagataaaag attactttga gaaattggtt ggatttattg   7320
atgatgctgt gaagaagctt aatgaattat cttttaaaac attcattgaa gatgttaaca   7380
aattccttga catgttgata aagaaattaa agtcatttga ttaccaccag tttgtagatg   7440
aaaccaatga caaaatccgt gaggtgactc agagactcaa tggtgaaatt caggctctgg   7500
aactaccaca aaaagctgaa gcattaaaac tgttttaga ggaaaccaag gccacagttg   7560
cagtgtatct ggaaagccta caggacacca aaataacctt aatcatcaat tggttacagg   7620
aggctttaag ttcagcatct ttggctcaca tgaaggccaa attccgagag actctagaag   7680
atacacgaga ccgaatgtat caaatggaca ttcagcagga acttcaacga tacctgtctc   7740
tggtaggcca ggtttatagc acacttgtca cctacatttc tgattggtgg actcttgctg   7800
ctaagaacct tactgacttt gcagagcaat attctatcca agattgggct aaacgtatga   7860
aagcattggt agagcaaggg ttcactgttc ctgaaatcaa gaccatcctt gggaccatgc   7920
ctgcctttga agtcagtctt caggctcttc agaaagctac cttccagaca cctgattta   7980 tagtccccct aacagatttg aggattccat cagttcagat aaacttcaaa gacttaaaaa   8040
atataaaaat cccatccagg ttttccacac cagaatttac catccttaac accttccaca   8100
ttccttcctt tacaattgac tttgtcgaaa tgaaagtaaa gatcatcaga accattgacc   8160
agatgcagaa cagtgagctg cagtggcccg ttccagatat atatctcagg gatctgaagg   8220
tggaggacat tcctctagcg agaatcaccc tgccagactc ccgtttacca gaaatcgcaa   8280
ttccagaatt cataatccca actctcaacc ttaatgattt tcaagttcct gaccttcaca   8340
taccagaatt ccagcttccc cacatctcac acacaattga agtacctact tttggcaagc   8400
tatacagtat tctgaaaatc caatctcctc ttttcacatt agatgcaaat gctgacatag   8460
ggaatggaac cacctcagca aacgaagcag gtatcgcagc ttccatcact gccaaaggag   8520
agtccaaatt agaagttctc aattttgatt ttcaagcaaa tgcacaactc tcaaaccctca   8580 agattaatcc gctggctctg aaggagtcag tgaagttctc cagcaagtac ctgagaacgg   8640
agcatgggag tgaaatgctg ttttttggaa atgctattga gggaaaatca acacagtgg   8700 caagtttaca cacagaaaaa aatacactgg agcttagtaa tggagtgatt gtcaagataa   8760
acaatcagct taccctggat agcaacacta aatacttcca caattgaac atccccaaac   8820 tggacttctc tagtcaggct gacctgcgca acgagatcaa gacactgttg aaagctggcc   8880
```

```
acatagcatg gacttcttct ggaaaagggt catggaaatg ggcctgcccc agattctcag    8940
atgagggaac acatgaatca caaattagtt tcaccataga aggaccccct cacttcctttg   9000 gactgtccaa taagatcaat agcaaacacc taagagtaaa ccaaaacttg gtttatgaat    9060
ctggctccct caacttttct aaacttgaaa ttcaatcaca agtcgattcc cagcatgtgg    9120
gccacagtgt tctaactgct aaaggcatgg cactgtttgg agaagggaag gcagagttta    9180
ctgggaggca tgatgctcat ttaaatggaa aggttattgg aactttgaaa aattctcttt    9240
tcttttcagc ccagccattt gagatcacgg catccacaaa caatgaaggg aatttgaaag    9300
ttcgttttcc attaaggtta acagggaaga tagacttcct gaataactat gcactgtttc    9360
tgagtcccag tgcccagcaa gcaagttggc aagtaagtgc taggttcaat cagtataagt    9420
acaaccaaaa tttctctgct ggaaacaacg agaacattat ggaggcccat gtaggaataa    9480
atggagaagc aaatctggat ttcttaaaca ttcctttaac aattcctgaa atgcgtctac    9540
cttacacaat aatcacaact cctccactga aagatttctc tctatgggaa aaaacaggct    9600
tgaaggaatt cttgaaaacg acaaagcaat catttgattt aagtgtaaaa gctcagtata    9660
agaaaaacaa acacaggcat tccatcacaa atcctttggc tgtgctttgt gagtttatca    9720
gtcagagcat caaatccttt gacaggcatt ttgaaaaaaa cagaaacaat gcattagatt    9780
ttgtcaccaa atcctataat gaaacaaaaa ttaagtttga taagtacaaa gctgaaaaat    9840
ctcacgacga gctccccagg accttcaaa ttcctggata cactgttcca gttgtcaatg    9900
ttgaagtgtc tccattcacc atagagatgt cggcattcgg ctatgtgttc ccaaaagcag    9960
tcagcatgcc tagtttctcc atcctaggtt ctgacgtccg tgtgccttca tacacattaa    10020
tcctgccatc attagagctg ccagtccttc atgtccctag aaatctcaag ctttctcttc    10080
cacatttcaa ggaattgtgt accataagcc atatttttat tcctgccatg ggcaatatta    10140
cctatgattt ctccttaaa tcaagtgtca tcacactgaa taccaatgct gaacttttta    10200
accagtcaga tattgttgct catctccttt cttcatcttc atctgtcatt gatgcactgc    10260
agtacaaatt agagggcacc acaagattga caagaaaaag gggattgaag ttagccacag    10320
ctctgtctct gagcaacaaa tttgtggagg gtagtcataa cagtactgtg agcttaacca    10380
cgaaaaatat ggaagtgtca gtggcaaaaa ccacaaaagc cgaaattcca attttgagaa    10440
tgaatttcaa gcaagaactt aatggaaata ccaagtcaaa acctactgtc tcttcctcca    10500
tggaatttaa gtatgatttc aattcttcaa tgctgtactc taccgctaaa ggagcagttg    10560
accacaagct tagcttggaa agcctccacct cttacttttc cattgagtca tctaccaaag    10620
gagatgtcaa gggttcggtt ctttctcggg aatattcagg aactattgct agtgaggcca    10680
acacttactt gaattccaag agcacacggt cttcagtgaa gctgcagggc acttccaaaa    10740
ttgatgatat ctggaacctt gaagtaaaag aaaattttgc tggagaagcc acactccaac    10800
gcatatattc cctctgggag cacagtacga aaaaccactt acagctagag ggcctctttt    10860
tcaccaacgg agaacataca agcaaagcca ccctggaact ctctccatgg caaatgtcag    10920
ctcttgttca ggtccatgca agtcagccca gttccttcca tgatttccct gaccttggcc    10980
aggaagtggc cctgaatgct aacactaaga accagaagat cagatggaaa aatgaagtcc    11040
ggattcattc tgggtctttc cagagccagg tcgagctttc caatgaccaa gaaaaggcac    11100
accttgacat tgcaggatcc ttagaaggac acctaaggtt cctcaaaaat atcatcctac    11160
cagtctatga caagagctta tgggatttcc taaagctgga tgtaaccacc agcattggta    11220
ggagacagca tcttcgtgtt tcaactgcct ttgtgtacac caaaaacccc aatggctatt    11280
```

```
cattctccat ccctgtaaaa gttttggctg ataaattcat tactcctggg ctgaaactaa    11340
atgatctaaa ttcagttctt gtcatgccta cgttccatgt cccatttaca gatcttcagg    11400
ttccatcgtg caaacttgac ttcagagaaa tacaaatcta taagaagctg agaacttcat    11460
catttgccct caacctacca acactccccg aggtaaaatt ccctgaagtt gatgtgttaa    11520
caaaatattc tcaaccagaa gactccttga ttccctttt tgagataacc gtgcctgaat    11580
ctcagttaac tgtgtcccag ttcacgcttc caaaaagtgt ttcagatggc attgctgctt    11640
tggatctaaa tgcagtagcc aacaagatcg cagactttga gttgcccacc atcatcgtgc    11700
ctgagcagac cattgagatt ccctccatta agttctctgt acctgctgga attgtcattc    11760
cttcctttca agcactgact gcacgctttg aggtagactc tcccgtgtat aatgccactt    11820
ggagtgccca tttgaaaaac aaagcagatt atgttgaaac agtcctggat tccacatgca    11880
gctcaaccgt acagttccta gaatatgaac taaatgtttt gggaacacac aaaatcgaag    11940
atggtacgtt agcctctaag actaaaggaa cacttgcaca ccgtgacttc agtgcagaat    12000
atgaagaaga tggcaaattt gaaggacttc aggaatggga aggaaaagcg cacctcaata    12060
tcaaaagccc agcgttcacc gatctccatc tgcgctacca gaaagacaag aaaggcatct    12120
ccacctcagc agcctcccca gccgtaggca ccgtgggcat ggatatggat gaagatgacg    12180
acttttctaa atggaacttc tactacagcc ctcagtcctc tccagataaa aaactccacca    12240 tattcaaaac tgagttgagg gtccgggaat ctgatgagga aactcagatc aaagttaatt    12300
gggaagaaga ggcagcttct ggcttgctaa cctctctgaa agacaacgtg cccaaggcca    12360
caggggtcct ttatgattat gtcaacaagt accactggga acacacaggg ctcaccctga    12420
gagaagtgtc ttcaaagctg agaagaaatc tgcagaacaa tgctgagtgg gtttatcaag    12480
gggccattag gcaaattgat gatatcgacg tgaggttcca gaaagcagcc agtggcacca    12540
ctgggaccta ccaagagtgg aaggacaagg cccagaatct gtaccaggaa ctgttgactc    12600
aggaaggcca agccagtttc cagggactca aggataacgt gtttgatggc ttggtacgag    12660
ttactcaaaa attccatatg aaagtcaagc atctgattga ctcactcatt gattttctga    12720
acttccccag attccagttt ccggggaaac ctggatata cactagggag gaactttgca    12780
ctatgttcat aagggaggta gggacggtac tgtcccaggt atattcgaaa gtccataatg    12840
gttcagaaat actgttttcc tatttccaag acctagtgat tacacttcct ttcgagttaa    12900
ggaaacataa actaatagat gtaatctcga tgtatagggga actgttgaaa gatttatcaa    12960
aagaagccca agaggtattt aaagccattc agtctctcaa gaccacagag gtgctacgta    13020
atcttcagga ccttttacaa ttcattttcc aactaataga agataacatt aaacagctga    13080
aagagatgaa atttacttat cttattaatt atatccaaga tgagatcaac acaatcttca    13140
atgattatat cccatatgtt tttaaattgt tgaaagaaaa cctatgcctt aatcttcata    13200
agttcaatga atttattcaa aacgagcttc aggaagcttc tcaagagtta cagcagatcc    13260
atcaatacat tatggcccct cgtgaagaat attttgatcc aagtatagtt ggctggacag    13320
tgaaatatta tgaacttgaa gaaaagatag tcagtctgat caagaacctg ttagttgctc    13380
ttaaggactt ccattctgaa tatattgtca gtgcctctaa ctttacttcc caactctcaa    13440
gtcaagttga gcaatttctg cacagaaata ttcaggaata tcttagcatc cttaccgatc    13500
cagatgaaaa agggaaagag aagattgcag agctttctgc cactgctcag gaaataatta    13560
aaagccaggc cattgcgacg aagaaaataa tttctgatta ccaccagcag tttagatata    13620
```

```
aactgcaaga ttttcagac caactctctg attactatga aaaattatt gctgaatcca    13680 aaagattgat tgacctgtcc attcaaaact accacacatt tctgatatac atcacggagt   13740
tactgaaaaa gctgcaatca accacagtca tgaaccccta catgaagctt gctccaggag   13800
aacttactat catcctctaa tttttaaaa gaaatcttca tttattcttc ttttccaatt    13860
gaactttcac atagcacaga aaaaattcaa actgcctata ttgataaaac catacagtga   13920
gccagccttg cagtaggcag tagactataa gcagaagcac atatgaactg gacctgcacc   13980
aaagctggca ccagggctcg aaggtctct gaactcagaa ggatggcatt ttttgcaagt    14040
taaagaaaat caggatctga gttatttgc taaacttggg ggaggaggaa caaataaatg     14100
gagtctttat tgtgtatcat a                                             14121
```

```
<210> SEQ ID NO 11
<211> LENGTH: 21
<212> TYPE: DNA
<213> ORGANISM: Artificial Sequence
<220> FEATURE:
<223> OTHER INFORMATION: PCR Primer

<400> SEQUENCE: 11
tgctaaaggc acatatggcc t                                             21

<210> SEQ ID NO 12
<211> LENGTH: 23
<212> TYPE: DNA
<213> ORGANISM: Artificial Sequence
<220> FEATURE:
<223> OTHER INFORMATION: PCR Primer

<400> SEQUENCE: 12
ctcaggttgg actctccatt gag                                           23

<210> SEQ ID NO 13
<211> LENGTH: 28
<212> TYPE: DNA
<213> ORGANISM: Artificial Sequence
<220> FEATURE:
<223> OTHER INFORMATION: PCR Probe

<400> SEQUENCE: 13
cttgtcagag ggatcctaac actggccg                                      28

<210> SEQ ID NO 14
<211> LENGTH: 19
<212> TYPE: DNA
<213> ORGANISM: Artificial Sequence
<220> FEATURE:
<223> OTHER INFORMATION: PCR Primer

<400> SEQUENCE: 14
gaaggtgaag gtcggagtc                                                19

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
gaagatggtg atgggatttc                                               20
```

<210> SEQ ID NO 16
<211> LENGTH: 20
<212> TYPE: DNA
<213> ORGANISM: Artificial Sequence
<220> FEATURE:
<223> OTHER INFORMATION: PCR Probe

<400> SEQUENCE: 16
caagcttccc gttctcagcc                                          20

<210> SEQ ID NO 17
<211> LENGTH: 2354
<212> TYPE: DNA
<213> ORGANISM: M. musculus

<400> SEQUENCE: 17

| | | | | | |
|---|---|---|---|---|---|
| gaattccaac | ttcctcacct | ctcacataca | attgaaatac | ctgcttttgg | caaactgcat | 60 |
| agcatcctta | agatccaatc | tcctctcttt | atattagatg | ctaatgccaa | catacagaat | 120 |
| gtaacaactt | cagggaacaa | agcagagatt | gtggcttctg | tcactgctaa | aggagagtcc | 180 |
| caatttgaag | ctctcaattt | tgattttcaa | gcacaagctc | aattcctgga | gttaaatcct | 240 |
| catcctccag | tcctgaagga | atccatgaac | ttctccagta | agcatgtgag | aatggagcat | 300 |
| gagggtgaga | tagtatttga | tggaaaggcc | attgagggga | aatcagacac | agtcgcaagt | 360 |
| ttacacacag | agaaaaatga | agtagagttt | aataatggta | tgactgtcaa | agtaaacaat | 420 |
| cagctcaccc | ttgacagtca | cacaaagtac | ttccacaagt | tgagtgttcc | taggctggac | 480 |
| ttctccagta | aggcttctct | taataatgaa | atcaagacac | tattagaagc | tggacatgtg | 540 |
| gcattgacat | cttcagggac | agggtcatgg | aactgggcct | gtcccaactt | ctcggatgaa | 600 |
| ggcatacatt | cgtcccaaat | tagctttact | gtggatggtc | ccattgcttt | tgttggacta | 660 |
| tccaataaca | taaatggcaa | acacttacgg | gtcatccaaa | aactgactta | tgaatctggc | 720 |
| ttcctcaact | attctaagtt | tgaagttgag | tcaaaagttg | aatctcagca | cgtgggctcc | 780 |
| agcattctaa | cagccaatgg | tcgggcactg | ctcaaggacg | caaaggcaga | aatgactggt | 840 |
| gagcacaatg | ccaacttaaa | tggaaaagtt | attggaactt | tgaaaaattc | tctcttcttt | 900 |
| tcagcacaac | catttgagat | tactgcatcc | acaaataatg | aaggaaattt | gaaagtgggg | 960 |
| tttccactaa | agctgactgg | gaaaatagac | ttcctgaata | actatgcatt | gtttctgagt | 1020 |
| ccccgtgccc | aacaagcaag | ctggcaagcg | agtaccagat | tcaatcagta | caaatacaat | 1080 |
| caaaactttt | ctgctataaa | caatgaacac | aacatagaag | ccagtatagg | aatgaatgga | 1140 |
| gatgccaacc | tggatttctt | aaacatacct | ttaacaattc | ctgaaattaa | cttgccttac | 1200 |
| acggagttca | aaactcccct | actgaaggat | ttctccatat | gggaagaaac | aggcttgaaa | 1260 |
| gaattttga | agcaacaaa | gcaatcattt | gatttgagtg | taaaggctca | atataaaaag | 1320 |
| aacagtgaca | agcattccat | tgttgtccct | ctgggtatgt | tttatgaatt | tattctcaac | 1380 |
| aatgtcaatt | cgtgggacag | aaaatttgag | aaagtcagaa | acaatgcttt | acattttctt | 1440 |
| accacctcct | ataatgaagc | aaaaattaag | gttgataagt | acaaaactga | aaattccctt | 1500 |
| aatcagccct | ctgggacctt | tcaaaatcat | ggctacacta | tcccagttgt | caacattgaa | 1560 |
| gtatctccat | ttgctgtaga | gacactggct | tccaggcatg | tgatccccac | agcaataagc | 1620 |
| accccaagtg | tcacaatccc | tggtcctaac | atcatggtgc | cttcatacaa | gttagtgctg | 1680 |
| ccaccccctgg | agttgccagt | tttccatggt | cctgggaatc | tattcaagtt | tttcctccca | 1740 |
| gatttcaagg | gattcaacac | tattgacaat | atttatattc | cagccatggg | caactttacc | 1800 |

-continued

| | |
|---|---|
| tatgactttt cttttaaatc aagtgtcatc acactgaata ccaatgctgg actttataac | 1860 |
| caatcagata tcgttgccca tttcctttct tcctcttcat ttgtcactga cgccctgcag | 1920 |
| tacaaattag agggaacatc acgtctgatg cgaaaaaggg gattgaaact agccacagct | 1980 |
| gtctctctaa ctaacaaatt tgtaaagggc agtcatgaca gcaccattag tttaaccaag | 2040 |
| aaaaacatgg aagcatcagt gagaacaact gccaacctcc atgctcccat attctcaatg | 2100 |
| aacttcaagc aggaacttaa tggaaatacc aagtcaaaac ccactgtttc atcatccatt | 2160 |
| gaactaaaact atgacttcaa ttcctcaaag ctgcactcta ctgcaacagg aggcattgat | 2220 |
| cacaagttca gcttagaaag tctcacttcc tacttttcca ttgagtcatt caccaaagga | 2280 |
| aatatcaaga gttccttcct ttctcaggaa tattcaggaa gtgttgccaa tgaagccaat | 2340 |
| gtatatctga attc | 2354 |

<210> SEQ ID NO 18
<211> LENGTH: 19
<212> TYPE: DNA
<213> ORGANISM: Artificial Sequence
<220> FEATURE:
<223> OTHER INFORMATION: PCR Primer

<400> SEQUENCE: 18
cgtgggctcc agcattcta                                                19

<210> SEQ ID NO 19
<211> LENGTH: 21
<212> TYPE: DNA
<213> ORGANISM: Artificial Sequence
<220> FEATURE:
<223> OTHER INFORMATION: PCR Primer

<400> SEQUENCE: 19
agtcatttct gcctttgcgt c                                             21

<210> SEQ ID NO 20
<211> LENGTH: 22
<212> TYPE: DNA
<213> ORGANISM: Artificial Sequence
<220> FEATURE:
<223> OTHER INFORMATION: PCR Probe

<400> SEQUENCE: 20
ccaatggtcg ggcactgctc aa                                            22

<210> SEQ ID NO 21
<211> LENGTH: 20
<212> TYPE: DNA
<213> ORGANISM: Artificial Sequence
<220> FEATURE:
<223> OTHER INFORMATION: PCR Primer

<400> SEQUENCE: 21
ggcaaattca acggcacagt                                               20

<210> SEQ ID NO 22
<211> LENGTH: 20
<212> TYPE: DNA
<213> ORGANISM: Artificial Sequence
<220> FEATURE:
<223> OTHER INFORMATION: PCR Primer

<400> SEQUENCE: 22
gggtctcgct cctggaagat                                               20

```
<210> SEQ ID NO 23
<211> LENGTH: 27
<212> TYPE: DNA
<213> ORGANISM: Artificial Sequence
<220> FEATURE:
<223> OTHER INFORMATION: PCR Probe

<400> SEQUENCE: 23
aaggccgaga atgggaagct tgtcatc                                         27
```

SNPS OF APOLIPOPROTEIN B AND MODULATION OF THEIR EXPRESSION

CROSS REFERENCE TO RELATED APPLICATIONS

This application is a continuation of U.S. application Ser. No. 11/124,020, filed May 5, 2005 (abandoned), which claims the benefit of priority of U.S. Provisional Application Ser. No. 60/568,409, filed May 5, 2004, each of which is herein incorporated by reference in its entirety.

SEQUENCE LISTING

The present application includes a Sequence Listing in electronic format. The Sequence Listing is provided as a file entitled 12207275999_SeqList.txt, created Jan. 28, 2011, which is 17.5 Kb in size. The information in the electronic format of the sequence listing is incorporated herein by reference in its entirety.

FIELD OF THE INVENTION

The present invention provides compositions and methods for modulating the expression of variants of apolipoprotein B (apo B). In particular, this invention relates to antisense compounds, particularly oligonucleotide compounds, which, in preferred embodiments, hybridize with nucleic acid molecules encoding apolipoprotein B and containing SNPs.

BACKGROUND OF THE INVENTION

Natural genetic sequence variability exists between individuals in any and every population. Subtle alteration(s) in the primary nucleotide sequence of a gene encoding a pharmaceutically-important protein may be manifested as significant variation in expression, structure and/or function of the protein. Such alterations may explain the different response of individuals to therapy with a particular drug.

Variability in genetic sequence is particularly likely to cause a variable response to therapy when the therapeutic is an antisense compound that modulates the expression of protein through specific hybridization to the genetic sequence. In this case, changes in the sequence of the DNA or RNA can have a direct effect on the ability of such a compound to specifically hybridize.

Identification of polymorphisms among various populations is desirable to tailor design of suitable antisense therapeutics, select antisense therapeutics to administer to a particular population, and also predict responsiveness to therapeutics.

SUMMARY OF THE INVENTION

The present invention is directed to antisense compounds, especially nucleic acid and nucleic acid-like oligomers, which are targeted to a nucleic acid encoding apolipoprotein B, and which modulate the expression of apolipoprotein B. Pharmaceutical and other compositions comprising the compounds of the invention are also provided. Further provided are methods of screening for modulators of apolipoprotein B and methods of modulating the expression of apolipoprotein B in cells, tissues or animals comprising contacting said cells, tissues or animals with one or more of the compounds or compositions of the invention. Methods of treating an animal, particularly a human, suspected of having or being prone to a disease or condition associated with expression of apolipoprotein B are also set forth herein. Such methods comprise administering a therapeutically or prophylactically effective amount of one or more of the compounds or compositions of the invention to the person in need of treatment.

DETAILED DESCRIPTION OF THE INVENTION

A. Overview of the Invention

The present invention employs antisense compounds, preferably oligonucleotides and similar species for use in modulating the function or effect of nucleic acid molecules encoding apolipoprotein B. This is accomplished by providing oligonucleotides which specifically hybridize with one or more nucleic acid molecules encoding apolipoprotein B. As used herein, the terms "target nucleic acid" and "nucleic acid molecule encoding apolipoprotein B" have been used for convenience to encompass DNA encoding apolipoprotein B, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of apolipoprotein B. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some preferred embodiments, homology, sequence identity or complementarity, between the oligomeric and target is between about 50% to about 60%. In some embodiments, homology, sequence identity or complementarity, is between about 60% to about 70%. In preferred embodiments, homology, sequence identity or complementarity, is between about 70% and about 80%. In more preferred embodiments, homology, sequence identity or complementarity, is between about 80% and about 90%. In some preferred embodiments, homology, sequence identity or complementarity, is about 90%, about 92%, about 94%, about 95%, about 96%, about 97%, about 98%, about 99% or about 100%.

B. Compounds of the Invention

According to the present invention, antisense compounds include antisense oligomeric compounds, antisense oligonucleotides, siRNAs, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA, also known as small interfering RNAs (siRNAs) could lead to gene silencing in animals came in 1995 from work in the nematode, *Caenorhabditis elegans* (Guo and Kempheus, *Cell*, 1995, 81, 611-620). Montgomery et al. have shown that the primary interference effects of dsRNA are posttranscriptional (Montgomery et al., *Proc. Natl. Acad. Sci. USA*, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, it has been shown that it is, in fact, the single-stranded RNA oligomers of antisense polarity of the dsRNAs which are the potent inducers of RNAi (Tijsterman et al., *Science*, 2002, 295, 694-697).

The antisense compounds of the present invention also include modified compounds in which a different base is present at one or more of the nucleotide positions in the compound. For example, if the first nucleotide is an adenosine, modified compounds may be produced which contain thymidine, guanosine or cytidine at this position. This may be done at any of the positions of the antisense compound. These compounds are then tested using the methods described herein to determine their ability to inhibit expression of apolipoprotein B mRNA.

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the antisense compounds of this invention, the present invention comprehends other families of antisense compounds as well, including but not limited to oligonucleotide analogs and mimetics such as those described herein.

The antisense compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the antisense compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the antisense compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 8-80 nucleobases in length comprising a stretch of at least eight (8) consecutive nucleobases selected from within the illustrative antisense compounds are considered to be suitable antisense compounds as well.

Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). It is also understood that preferred antisense compounds may be represented by oligonucleotide sequences that comprise at least 8 consecutive nucleobases from an internal portion of the sequence of an illustrative preferred antisense compound, and may extend in either or both directions until the oligonucleotide contains about 8 to about 80 nucleobases.

One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes apolipoprotein B.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding apolipoprotein B, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the sites where exons are joined. Targeting exon-exon junctions can be useful in situations where the overproduction of a normal splice product is implicated in disease, or where the overproduction of an aberrant splice product is implicated in disease. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). It is also understood that preferred antisense target segments may be represented by DNA or RNA sequences that comprise at least 8 consecutive nucleobases from an internal portion of the sequence of an illustrative preferred target segment, and may extend in either or both directions until the oligonucleotide contains about 8 to about 80 nucleobases. One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

The oligomeric antisense compounds can also be targeted to regions of a target nucleobase sequence, such as those disclosed herein. All regions of the target nucleobase sequence to which an oligomeric antisense compound can be targeted, wherein the regions are greater than or equal to 8 and less than or equal to 80 nucleobases, are described as follows:

Let R(n, n+m−1) be a region from a target nucleobase sequence, where "n" is the 5'-most nucleobase position of the region, where "n+m−1" is the 3'-most nucleobase position of the region and where "m" is the length of the region. A set "S(m)", of regions of length "m" is defined as the regions where n ranges from 1 to L−m+1, where L is the length of the target nucleobase sequence and L>m. A set, "A", of all regions can be constructed as a union of the sets of regions for each length from where m is greater than or equal to 8 and is less than or equal to 80.

This set of regions can be represented using the following mathematical notation:

$$A = \bigcup_m S(m) \text{ where } m \in N \mid 8 \leq m \leq 80$$

and $$S(m) = \{R_{n,n+m-1} \mid n \in \{1, 2, 3, \ldots, L-m+1\}\}$$

where the mathematical operator | indicates "such that", where the mathematical operator ∈ indicates "a member of a set" (e.g. y ∈ Z indicates that element y is a member of set Z), where x is a variable, where N indicates all natural numbers, defined as positive integers, and where the mathematical operator ∪ indicates "the union of sets".

For example, the set of regions for m equal to 8, 9 and 80 can be constructed in the following manner. The set of regions, each 8 nucleobases in length, S(m=8), in a target nucleobase sequence 100 nucleobases in length (L=100), beginning at position 1 (n=1) of the target nucleobase sequence, can be created using the following expression:

$$S(8)=\{R_{1,8} \mid n \in \{1,2,3,\ldots,93\}\}$$

and describes the set of regions comprising nucleobases 1-8, 2-9, 3-10, 4-11, 5-12, 6-13, 7-14, 8-15, 9-16, 10-17, 11-18, 12-19, 13-20, 14-21, 15-22, 16-23, 17-24, 18-25, 19-26, 20-27, 21-28, 22-29, 23-30, 24-31, 25-32, 26-33, 27-34, 28-35, 29-36, 30-37, 31-38, 32-39, 33-40, 34-41, 35-42, 36-43, 37-44, 38-45, 39-46, 40-47, 41-48, 42-49, 43-50, 44-51, 45-52, 46-53, 47-54, 48-55, 49-56, 50-57, 51-58, 52-59, 53-60, 54-61, 55-62, 56-63, 57-64, 58-65, 59-66, 60-67, 61-68, 62-69, 63-70, 64-71, 65-72, 66-73, 67-74, 68-75, 69-76, 70-77, 71-78, 72-79, 73-80, 74-81, 75-82, 76-83, 77-84, 78-85, 79-86, 80-87, 81-88, 82-89, 83-90, 84-91, 85-92, 86-93, 87-94, 88-95, 89-96, 90-97, 91-98, 92-99, 93-100.

An additional set for regions 20 nucleobases in length, in a target sequence 100 nucleobases in length, beginning at position 1 of the target nucleobase sequence, can be described using the following expression:

$$S(20)=\{R_{1,20} \mid n \in \{1,2,3,\ldots,81\}\}$$

and describes the set of regions comprising nucleobases 1-20, 2-21, 3-22, 4-23, 5-24, 6-25, 7-26, 8-27, 9-28, 10-29, 11-30, 12-31, 13-32, 14-33, 15-34, 16-35, 17-36, 18-37, 19-38, 20-39, 21-40, 22-41, 23-42, 24-43, 25-44, 26-45, 27-46, 28-47, 29-48, 30-49, 31-50, 32-51, 33-52, 34-53, 35-54, 36-55, 37-56, 38-57, 39-58, 40-59, 41-60, 42-61, 43-62, 44-63, 45-64, 46-65, 47-66, 48-67, 49-68, 50-69, 51-70, 52-71, 53-72, 54-73, 55-74, 56-75, 57-76, 58-77, 59-78, 60-79, 61-80, 62-81, 63-82, 64-83, 65-84, 66-85, 67-86, 68-87, 69-88, 70-89, 71-90, 72-91, 73-92, 74-93, 75-94, 76-95, 77-96, 78-97, 79-98, 80-99, 81-100.

An additional set for regions 80 nucleobases in length, in a target sequence 100 nucleobases in length, beginning at position 1 of the target nucleobase sequence, can be described using the following expression:

$$S(80)=\{R_{1,80} \mid n \in \{1,2,3,\ldots,21\}\}$$

and describes the set of regions comprising nucleobases 1-80, 2-81, 3-82, 4-83, 5-84, 6-85, 7-86, 8-87, 9-88, 10-89, 11-90, 12-91, 13-92, 14-93, 15-94, 16-95, 17-96, 18-97, 19-98, 20-99, 21-100.

Thus, in this example, A would include regions 1-8, 2-9, 3-10 . . . 93-100, 1-20, 2-21, 3-22 . . . 81-100, 1-80, 2-81, 3-82 . . . 21-100.

The union of these aforementioned example sets and other sets for lengths from 10 to 19 and 21 to 79 can be described using the mathematical expression $$A = \bigcup_m S(m)$$

where ∪ represents the union of the sets obtained by combining all members of all sets.

The mathematical expressions described herein defines all possible target regions in a target nucleobase sequence of any length L, where the region is of length m, and where m is greater than or equal to 8 and less than or equal to 80 nucleobases and, and where m is less than L, and where n is less than L−m+1.

D. Screening and Target Validation

In a further embodiment, the "preferred target segments" identified herein may be employed in a screen for additional compounds that modulate the expression of apolipoprotein B. "Modulators" are those compounds that decrease or increase the expression of a nucleic acid molecule encoding apolipoprotein B and which comprise at least an 8-nucleobase portion which is complementary to a preferred target segment. The screening method comprises the steps of contacting a preferred target segment of a nucleic acid molecule encoding apolipoprotein B with one or more candidate modulators, and selecting for one or more candidate modulators which decrease or increase the expression of a nucleic acid molecule encoding apolipoprotein B. Once it is shown that the candidate modulator or modulators are capable of modulating (e.g. either decreasing or increasing) the expression of a nucleic acid molecule encoding apolipoprotein B, the modulator may then be employed in further investigative studies of the function of apolipoprotein B, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The antisense compounds of the present invention can also be applied in the areas of drug discovery and target validation. The present invention comprehends the use of the compounds and preferred target segments identified herein in drug discovery efforts to elucidate relationships that exist between apolipoprotein B and a disease state, phenotype, or condition. These methods include detecting or modulating apolipoprotein B comprising contacting a sample, tissue, cell, or organism with the compounds of the present invention, measuring the nucleic acid or protein level of apolipoprotein B and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The antisense compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

The antisense compounds of the invention are useful for research and diagnostics, because these compounds hybridize to nucleic acids encoding apolipoprotein B. For example, oligonucleotides that are shown to hybridize with such efficiency and under such conditions as disclosed herein as to be effective apolipoprotein B inhibitors will also be effective primers or probes under conditions favoring gene amplification or detection, respectively. These primers and probes are useful in methods requiring the specific detection of nucleic acid molecules encoding apolipoprotein B and in the amplification of said nucleic acid molecules for detection or for use in further studies of apolipoprotein B. Hybridization of the antisense oligonucleotides, particularly the primers and probes, of the invention with a nucleic acid encoding apolipoprotein B can be detected by means known in the art. Such means may include conjugation of an enzyme to the oligonucleotide, radiolabelling of the oligonucleotide or any other suitable detection means. Kits using such detection means for detecting the level of apolipoprotein B in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of apolipoprotein B is treated by administering antisense compounds in accordance with this invention. For example, in one non-limiting embodiment, the methods comprise the step of administering to the animal in need of treatment, a therapeutically effective amount of an apolipoprotein B inhibitor. The apolipoprotein B inhibitors of the present invention effectively inhibit the activity of the apolipoprotein B protein or inhibit the expression of the apolipoprotein B protein. In one embodiment, the activity or expression of apolipoprotein 13 in an animal is inhibited by about 10%. Preferably, the activity or expression of apolipoprotein B in an animal is inhibited by about 30%. More preferably, the activity or expression of apolipoprotein B in an animal is inhibited by 50% or more. Thus, the oligomeric antisense compounds modulate expression of apolipoprotein B mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of apolipoprotein B may be measured in serum, adipose tissue, liver or any other body fluid, tissue or organ of the animal. Preferably, the cells contained within said fluids, tissues or organs being analyzed contain a nucleic acid molecule encoding apolipoprotein B protein and/or the apolipoprotein B protein itself.

The antisense compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base sometimes referred to as a "nucleobase" or simply a "base". The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkyl-phosphotriaminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thiono-alkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Modified Sugar and Internucleoside Linkages-Mimetics

In other preferred antisense compounds, e.g., oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al., *Science,* 1991, 254, 1497-1500.

Preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—CH$_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified antisense compounds may also contain one or more substituted sugar moieties. Preferred are antisense compounds, preferably antisense oligonucleotides, comprising one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$]$_2$, where n and m are from 1 to about 10. Other preferred oligonucleotides comprise one of the following at the 2' position: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy(2'-O—CH$_2$CH$_2$OCH$_3$, also known as 2'-O-(2-methoxyethyl) or 2'-MOE) (Martin et al., *Helv. Chim. Acta*, 1995, 78, 486-504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$, also described in examples hereinbelow.

Other preferred modifications include 2'-methoxy(2'-O—CH$_3$), 2'-aminopropoxy(2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabin (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—CH$_2$—)$_n$ group bridging the 2' oxygen atom and the 4' carbon atom wherein n is 1 or 2. LNAs and preparation thereof are described in WO 98/39352 and WO 99/14226.

Natural and Modified Nucleobases

Antisense compounds may also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyl-adenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692; and 5,681,941.

Conjugates

Another modification of the antisense compounds of the invention involves chemically linking to the antisense compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosures of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Antisense compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodo-benzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. Chimeric antisense oligonucleotides are thus a form of antisense compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Chimeric antisense compounds can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the aft as "gapmers" or gapped oligonucleotides. Oligonucleotides of the second type are also known in the art as "hemimers" or "wingmers". Such compounds have also been referred to in the art as hybrids. In a gapmer that is 20 nucleotides in length, a gap or wing can be 1, 2, 3, 4, 5, 6, 7, 8, 9, 10, 11, 12, 13, 14, 15, 16, 17 or 18 nucleotides in length. In one embodiment, a 20-nucleotide gapmer is comprised of a gap 8 nucleotides in length, flanked on both the 5' and 3' sides by wings 6 nucleotides in length. In another embodiment, a 20-nucleotide gapmer is comprised of a gap 10 nucleotides in length, flanked on both the 5' and 3' sides by wings 5 nucleotides in length. In another embodiment, a 20-nucleotide gapmer is comprised of a gap 12 nucleotides in length flanked on both the 5' and 3' sides by wings 4 nucleotides in length. In a further embodiment, a 20-nucleotide gapmer is comprised of a gap 14 nucleotides in length flanked on both the 5' and 3' sides by wings 3 nucleotides in length. In another embodiment, a 20-nucleotide gapmer is comprised of a gap 16 nucleotides in length flanked on both the 5' and 3' sides by wings 2 nucleotides in length. In a further embodiment, a 20-nucleotide gapmer is comprised of a gap 18 nucleotides in length flanked on both the 5' and 3' ends by wings 1 nucleotide in length. Alternatively, the wings are of different lengths, for example, a 20-nucleotide gapmer may be comprised of a gap 10 nucleotides in length, flanked by a 6-nucleotide wing on one side (5' or 3') and a 4-nucleotide wing on the other side (5' or 3'). In a hemimer, an "open end" chimeric antisense compound, 20 nucleotides in length, a gap segment, located at either the 5' or 3' terminus of the oligomeric compound, can be 1, 2, 3, 4, 5, 6, 7, 8, 9, 10, 11, 12, 13, 14, 15, 16, 17, 18 or 19 nucleotides in length. For example, a 20-nucleotide hemimer can have a gap segment of 10 nucleotides at the 5' end and a second segment of 10 nucleotides at the 3' end. Alternatively, a 20-nucleotide hemimer can have a gap segment of 10 nucleotides at the 3' end and a second segment of 10 nucleotides at the 5' end.

Representative United States patents that teach the preparation of such hybrid structures include, but are not limited to, U.S. Pat. Nos. 5,013,830; 5,149,797; 5,220,007; 5,256,775;

5,366,878; 5,403,711; 5,491,133; 5,565,350; 5,623,065; 5,652,355; 5,652,356; and 5,700,922.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 µm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. No. 09/108,673 (filed Jul. 1, 1998), Ser. No. 09/315,298 (filed May 20, 1999) and Ser. No. 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Oligonucleotides may be formulated for delivery in vivo in an acceptable dosage form, e.g. as parenteral or non-parenteral formulations. Parenteral formulations include intravenous (IV), subcutaneous (SC), intraperitoneal (IP), intravitreal and intramuscular (IM) formulations, as well as formulations for delivery via pulmonary inhalation, intranasal administration, topical administration, etc. Non-parenteral formulations include formulations for delivery via the alimentary canal, e.g. oral administration, rectal administration, intrajejunal instillation, etc. Rectal administration includes administration as an enema or a suppository. Oral administration includes administration as a capsule, a gel capsule, a pill, an elixir, etc.

In some embodiments, an oligonucleotide may be administered to a subject via an oral route of administration. The subject may be an animal or a human (man). An animal subject may be a mammal, such as a mouse, a rat, a dog, a guinea pig, a non-human primate, a cat or a pig. Non-human primates include monkeys and chimpanzees. A suitable animal subject may be an experimental animal, such as a mouse, a rat, a dog, a non-human primate, a cat or a pig.

In some embodiments, the subject may be a human. In certain embodiments, the subject may be a human patient in need of therapeutic treatment as discussed in more detail herein. In certain embodiments, the subject may be in need of modulation of expression of one or more genes as discussed in more detail herein. In some particular embodiments, the subject may be in need of inhibition of expression of one or more genes as discussed in more detail herein. In particular embodiments, the subject may be in need of modulation, i e inhibition or enhancement, of hepatic lipase in order to obtain therapeutic indications discussed in more detail herein.

In some embodiments, non-parenteral (e.g. oral) oligonucleotide formulations according to the present invention result in enhanced bioavailability of the oligonucleotide. In this context, the term "bioavailability" refers to a measurement of that portion of an administered drug which reaches the circulatory system (e.g. blood, especially blood plasma) when a particular mode of administration is used to deliver the drug. Enhanced bioavailability refers to a particular mode of administration's ability to deliver oligonucleotide to the peripheral blood plasma of a subject relative to another mode of administration. For example, when a non-parenteral mode of administration (e.g. an oral mode) is used to introduce the drug into a subject, the bioavailability for that mode of administration may be compared to a different mode of administration, e.g. an IV mode of administration. In some embodiments, the area under a compound's blood plasma concentration curve ($AUC_0$) after non-parenteral (e.g. oral, rectal, intrajejunal) administration may be divided by the area under the drug's plasma concentration curve after intravenous (i.v.) administration ($AUC_{iv}$) to provide a dimensionless quotient (relative bioavailability, RB) that represents fraction of compound absorbed via the non-parenteral route as compared to the IV route. A composition's bioavailability is said to be enhanced in comparison to another composition's bioavailability when the first composition's relative bioavailability ($RB_1$) is greater than the second composition's relative bioavailability ($RB_2$).

In general, bioavailability correlates with therapeutic efficacy when a compound's therapeutic efficacy is related to the blood concentration achieved, even if the drug's ultimate site of action is intracellular (van Berge-Henegouwen et al., *Gastroenterol.*, 1977, 73, 300). Bioavailability studies have been used to determine the degree of intestinal absorption of a drug by measuring the change in peripheral blood levels of the drug after an oral dose (DiSanto, Chapter 76 *In: Remington's Pharmaceutical Sciences*, 18th Ed., Gennaro, ed., Mack Publishing Co., Easton, Pa., 1990, pages 1451-1458).

In general, an oral composition's bioavailability is said to be "enhanced" when its relative bioavailability is greater than the bioavailability of a composition substantially consisting of pure oligonucleotide, i.e. oligonucleotide in the absence of a penetration enhancer.

Organ bioavailability refers to the concentration of compound in an organ. Organ bioavailability may be measured in test subjects by a number of means, such as by whole-body radiography. Organ bioavailability may be modified, e.g. enhanced, by one or more modifications to the oligonucleotide, by use of one or more carrier compounds or excipients, etc. as discussed in more detail herein. In general, an increase in bioavailability will result in an increase in organ bioavailability.

Oral oligonucleotide compositions according to the present invention may comprise one or more "mucosal penetration enhancers," also known as "absorption enhancers" or simply as "penetration enhancers." Accordingly, some embodiments of the invention comprise at least one oligonucleotide in combination with at least one penetration enhancer. In general, a penetration enhancer is a substance that facilitates the transport of a drug across mucous membrane(s) associated with the desired mode of administration, e.g. intestinal epithelial membranes. Accordingly it is desirable to select one or more penetration enhancers that facilitate the uptake of an oligonucleotide, without interfering with the activity of the oligonucleotide, and in a such a manner the oligonucleotide can be introduced into the body of an animal without unacceptable side-effects such as toxicity, irritation or allergic response.

Embodiments of the present invention provide compositions comprising one or more pharmaceutically acceptable penetration enhancers, and methods of using such compositions, which result in the improved bioavailability of oligonucleotides administered via non-parenteral modes of administration. Heretofore, certain penetration enhancers have been used to improve the bioavailability of certain drugs. See Muranishi, *Crit. Rev. Ther. Drug Carrier Systems*, 1990, 7, 1 and Lee et al., *Crit. Rev. Ther. Drug Carrier Systems*, 1991, 8, 91. It has been found that the uptake and delivery of oligonucleotides, relatively complex molecules which are known to be difficult to administer to animals and man, can be greatly improved even when administered by non-parenteral means through the use of a number of different classes of penetration enhancers.

In some embodiments, compositions for non-parenteral administration include one or more modifications from naturally-occurring oligonucleotides (i.e. full-phosphodiester deoxyribosyl or full-phosphodiester ribosyl oligonucleotides). Such modifications may increase binding affinity, nuclease stability, cell or tissue permeability, tissue distribution, or other biological or pharmacokinetic property. Modifications may be made to the base, the linker, or the sugar, in general, as discussed in more detail herein with regards to oligonucleotide chemistry. In some embodiments of the invention, compositions for administration to a subject, and in particular oral compositions for administration to an animal or human subject, will comprise modified oligonucleotides having one or more modifications for enhancing affinity, stability, tissue distribution, or other biological property.

Suitable modified linkers include phosphorothioate linkers. In some embodiments according to the invention, the oligonucleotide has at least one phosphorothioate linker. Phosphorothioate linkers provide nuclease stability as well as plasma protein binding characteristics to the oligonucleotide. Nuclease stability is useful for increasing the in vivo lifetime of oligonucleotides, while plasma protein binding decreases the rate of first pass clearance of oligonucleotide via renal excretion. In some embodiments according to the present invention, the oligonucleotide has at least two phosphorothioate linkers. In some embodiments, wherein the oligonucleotide has exactly n nucleosides, the oligonucleotide has from one to n-1 phosphorothioate linkages. In some embodiments, wherein the oligonucleotide has exactly n nucleosides, the oligonucleotide has n-1 phosphorothioate linkages. In other embodiments wherein the oligonucleotide has exactly n nucleoside, and Os even, the oligonucleotide has from 1 to n/2 phosphorothioate linkages, or, when n is odd, from 1 to (n-1)/2 phosphorothioate linkages. In some embodiments, the oligonucleotide has alternating phosphodiester (PO) and phosphorothioate (PS) linkages. In other embodiments, the oligonucleotide has at least one stretch of two or more consecutive PO linkages and at least one stretch of two or more PS linkages. In other embodiments, the oligonucleotide has at least two stretches of PO linkages interrupted by at least on PS linkage.

In some embodiments, at least one of the nucleosides is modified on the ribosyl sugar unit by a modification that imparts nuclease stability, binding affinity or some other beneficial biological property to the sugar. In some cases, the sugar modification includes a 2'-modification, e.g. the 2'-OH of the ribosyl sugar is replaced or substituted. Suitable replacements for 2'-OH include 2'-F and 2'-arabino-F. Suitable substitutions for OH include 2'-O-alkyl, e.g. 2-O-methyl, and 2'-O-substituted alkyl, e.g. 2'-O-methoxyethyl, 2'-O-aminopropyl, etc. In some embodiments, the oligonucleotide contains at least one 2'-modification. In some embodiments, the oligonucleotide contains at least 2 2'-modifications. In some embodiments, the oligonucleotide has at least one 2'-modification at each of the termini (i.e. the 3'- and 5'-terminal nucleosides each have the same or different 2'-modifications). In some embodiments, the oligonucleotide has at least two sequential 2'-modifications at each end of the oligonucleotide. In some embodiments, oligonucleotides further comprise at least one deoxynucleoside. In particular embodiments, oligonucleotides comprise a stretch of deoxynucleosides such that the stretch is capable of activating RNase (e.g. RNase H) cleavage of an RNA to which the oligonucleotide is capable of hybridizing. In some embodiments, a stretch of deoxynucleosides capable of activating RNase-mediated cleavage of RNA comprises about 6 to about 16, e.g. about 8 to about 16 consecutive deoxynucleosides.

Oral compositions for administration of non-parenteral oligonucleotide compositions of the present invention may be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. A common requirement for these modes of administration is absorption over some portion or all of the alimentary tract and a need for efficient mucosal penetration of the nucleic acid(s) so administered.

Delivery of a drug via the oral mucosa, as in the case of buccal and sublingual administration, has several desirable features, including, in many instances, a more rapid rise in plasma concentration of the drug than via oral delivery (Harvey, Chapter 35 *In: Remington's Pharmaceutical Sciences*, 18th Ed., Gennaro, ed., Mack Publishing Co., Easton, Pa., 1990, page 711).

Endoscopy may be used for drug delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., *Gan To Kagaku Ryoho*, 1992, 19(10 Suppl.), 1591). Pharmaceutical compositions, including liposomal formulations, can be delivered directly into portions of the alimentary canal, such as, e.g., the duodenum (Somogyi et al., *Pharm. Res.*, 1995, 12, 149) or the gastric submucosa (Alcamo et al., *Japa-* nese *J. Cancer Res.*, 1994, 85, 652) via endoscopic means. Gastric lavage devices (Inoue et al., *Artif. Organs*, 1997, 21, 28) and percutaneous endoscopic feeding devices (Pennington et al., *Ailment Pharmacol. Ther.*, 1995, 9, 471) can also be used for direct alimentary delivery of pharmaceutical compositions.

In some embodiments, oligonucleotide formulations may be administered through the anus into the rectum or lower intestine. Rectal suppositories, retention enemas or rectal catheters can be used for this purpose and may be preferred when patient compliance might otherwise be difficult to achieve (e.g., in pediatric and geriatric applications, or when the patient is vomiting or unconscious). Rectal administration can result in more prompt and higher blood levels than the oral route. (Harvey, Chapter 35 *In: Remington's Pharmaceutical Sciences*, 18th Ed., Gennaro, ed., Mack Publishing Co., Easton, Pa., 1990, page 711). Because about 50% of the drug that is absorbed from the rectum will bypass the liver, administration by this route significantly reduces the potential for first-pass metabolism (Benet et al., Chapter 1 *In: Goodman & Gilman's The Pharmacological Basis of Therapeutics*, 9th Ed., Hardman et al., eds., McGraw-Hill, New York, N.Y., 1996).

One advantageous method of non-parenteral administration oligonucleotide compositions is oral delivery. Some embodiments employ various penetration enhancers in order to effect transport of oligonucleotides and other nucleic acids across mucosal and epithelial membranes. Penetration enhancers may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Accordingly, some embodiments comprise oral oligonucleotide compositions comprising at least one member of the group consisting of surfactants, fatty acids, bile salts, chelating agents, and non-chelating surfactants. Further embodiments comprise oral oligonucleotide comprising at least one fatty acid, e.g. capric or lauric acid, or combinations or salts thereof. Other embodiments comprise methods of enhancing the oral bioavailability of an oligonucleotide, the method comprising co-administering the oligonucleotide and at least one penetration enhancer.

Other excipients that may be added to oral oligonucleotide compositions include surfactants (or "surface-active agents"), which are chemical entities which, when dissolved in an aqueous solution, reduce the surface tension of the solution or the interfacial tension between the aqueous solution and another liquid, with the result that absorption of oligonucleotides through the alimentary mucosa and other epithelial membranes is enhanced. In addition to bile salts and fatty acids, surfactants include, for example, sodium lauryl sulfate, polyoxyethylene-9-lauryl ether and polyoxyethylene-20-cetyl ether (Lee et al., *Critical Reviews in Therapeutic Drug Carrier Systems*, 1991, page 92); and perfluorohemical emulsions, such as FC-43 (Takahashi et al., *J. Pharm. Phamacol.*, 1988, 40, 252).

Fatty acids and their derivatives which act as penetration enhancers and may be used in compositions of the present invention include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glyceryl 1-monocaprate, 1-dodecylazacycloheptan-2-one, acylcarnitines, acylcholines and mono- and di-glycerides thereof and/or physiologically acceptable salts thereof (i.e., oleate, laurate, caprate, myristate, palmitate, stearate, linoleate, etc.) (Lee et al., *Critical Reviews in Therapeutic Drug Carrier Systems*, 1991, page 92; Muranishi, *Critical Reviews in Therapeutic Drug Carrier Systems*, 1990, 7, 1; El-Hariri et al., *J. Pharm. Pharmacol.*, 1992, 44, 651).

In some embodiments, oligonucleotide compositions for oral delivery comprise at least two discrete phases, which phases may comprise particles, capsules, gel-capsules, microspheres, etc. Each phase may contain one or more oligonucleotides, penetration enhancers, surfactants, bioadhesives, effervescent agents, or other adjuvant, excipient or diluent. In some embodiments, one phase comprises at least one oligonucleotide and at lease one penetration enhancer. In some embodiments, a first phase comprises at least one oligonucleotide and at least one penetration enhancer, while a second phase comprises at least one penetration enhancer. In some embodiments, a first phase comprises at least one oligonucleotide and at least one penetration enhancer, while a second phase comprises at least one penetration enhancer and substantially no oligonucleotide. In some embodiments, at least one phase is compounded with at least one degradation retardant, such as a coating or a matrix, which delays release of the contents of that phase. In some embodiments, a first phase comprises at least one oligonucleotide, at least one penetration enhancer, while a second phase comprises at least one penetration enhancer and a release-retardant. In particular embodiments, an oral oligonucleotide comprises a first phase comprising particles containing an oligonucleotide and a penetration enhancer, and a second phase comprising particles coated with a release-retarding agent and containing penetration enhancer.

A variety of bile salts also function as penetration enhancers to facilitate the uptake and bioavailability of drugs. The physiological roles of bile include the facilitation of dispersion and absorption of lipids and fat-soluble vitamins (Brunton, Chapter 38 *In: Goodman & Gilman's The Pharmacological Basis of Therapeutics*, 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (CDCA, sodium chenodeoxycholate), ursodeoxycholic acid (UDCA), sodium tauro-24,25-dihydrofusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 *In: Remington's Pharmaceutical Sciences*, 18th Ed., Gennaro, ed., Mack Publishing Co., Easton, Pa., 1990, pages 782-783; Muranishi, *Critical Reviews in Therapeutic Drug Carrier Systems*, 1990, 7, 1; Yamamoto et al., *J. Pharm. Exp. Ther.*, 1992, 263, 25; Yamashita et al., *J. Pharm. Sci.*, 1990, 79, 579).

In some embodiments, penetration enhancers useful in some embodiments of present invention are mixtures of penetration enhancing compounds. One such penetration enhancer is a mixture of UDCA (and/or CDCA) with capric and/or lauric acids or salts thereof e.g. sodium. Such mixtures are useful for enhancing the delivery of biologically active substances across mucosal membranes, in particular intestinal mucosa. Other penetration enhancer mixtures comprise about 5-95% of bile acid or salt(s) UDCA and/or CDCA with 5-95% capric and/or lauric acid. Particular penetration enhancers are mixtures of the sodium salts of UDCA, capric acid and lauric acid in a ratio of about 1:2:2 respectively. Anther such penetration enhancer is a mixture of capric and lauric acid (or salts thereof) in a 0.01:1 to 1:0.01 ratio (mole basis). In particular embodiments capric acid and lauric acid are present in molar ratios of e.g. about 0.1:1 to about 1:0.1, in particular about 0.5:1 to about 1:0.5.

Other excipients include chelating agents, i.e. compounds that remove metallic ions from solution by forming complexes therewith, with the result that absorption of oligonucleotides through the alimentary and other mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315). Chelating agents of the invention include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems*, 1991, page 92; Muranishi, *Critical Reviews in Therapeutic Drug Carrier Systems*, 1990, 7, 1; Buur et al., *J. Control Rel.*, 1990, 14, 43).

As used herein, non-chelating non-surfactant penetration enhancers may be defined as compounds that demonstrate insignificant activity as chelating agents or as surfactants but that nonetheless enhance absorption of oligonucleotides through the alimentary and other mucosal membranes (Muranishi, *Critical Reviews in Therapeutic Drug Carrier Systems*, 1990, 7, 1). This class of penetration enhancers includes, but is not limited to, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), can be used.

Some oral oligonucleotide compositions also incorporate carrier compounds in the formulation. As used herein, "carrier compound" or "carrier" can refer to a nucleic acid, or analog thereof, which may be inert (i.e., does not possess biological activity per se) or may be necessary for transport, recognition or pathway activation or mediation, or is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et at, *Antisense Res. Dev.*, 1995, 5, 115; Takakura et al., *Antisense & Nucl. Acid Drug Dev.*, 1996, 6, 177).

A "pharmaceutical carrier" or "excipient" may be a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, EXPLOTAB); and wetting agents (e.g., sodium lauryl sulphate, etc.).

Oral oligonucleotide compositions may additionally contain other adjunct components conventionally found in pharmaceutical compositions, at their art-established usage levels. Thus, for example, the compositions may contain additional, compatible, pharmaceutically-active materials such as, for example, antipuritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the present invention.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, from 0.1 μg to 10 g per kg of body weight, from 1.0 μg to 1 g per kg of body weight, from 10.0 μg to 100 mg per kg of body weight, from 100 μg to 10 mg per kg of body weight, or from 1 mg to 5 mg per kg of body weight and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

The effects of treatments with therapeutic compositions can be assessed following collection of tissues or fluids from a patient or subject receiving said treatments. It is known in the art that a biopsy sample can be procured from certain tissues without resulting in detrimental effects to a patient or subject. In certain embodiments, a tissue and its constituent cells comprise, but are not limited to, blood (e.g., hematopoietic cells, such as human hematopoietic progenitor cells, human hematopoietic stem cells, $CD34^+$ cells $CD4^+$ cells), lymphocytes and other blood lineage cells, bone marrow, breast, cervix, colon, esophagus, lymph node, muscle, peripheral blood, oral mucosa and skin. In other embodiments, a fluid and its constituent cells comprise, but are not limited to, blood, urine, semen, synovial fluid, lymphatic fluid and cerebro-spinal fluid. Tissues or fluids procured from patients can be evaluated for expression levels of the target mRNA or protein by techniques known in the art. Additionally, the mRNA or protein expression levels of other genes known or suspected to be associated with the specific disease state, condition or phenotype, or levels of biological markers associated with the disease state, condition or phenotype, can similarly be assessed. Target or associated gene mRNA levels can be measured or evaluated by real-time PCR, Northern blot, in situ hybridization or DNA array analysis. Target or associated protein levels or biomarkers can be measured or evaluated by ELISA, immunoblotting, quantitative protein assays, protein activity assays (for example, caspase activity assays) immunohistochemistry, immunocytochemistry or routine clinical analysis.

I. Polymorphisms

One common allelic genomic sequence for apolipoprotein B is set forth in SEQ ID NO: 1 and is referred to herein as the "wild-type" sequence. Novel polymorphic sites have been identified in this gene at positions 27751, 27735, 27685, 27683, 27679, 27634, 27627 and 27618 of SEQ ID NO: 1 (and corresponding positions 15695, 15711, 15761, 15763, 15767, 15812, 15819 and 15828 of the reverse complement, SEQ ID NO: 2).

A polymorphism is a sequence variation in the gene observed within the population, and can include nucleotide substitutions (single nucleotide polymorphisms or SNPs), insertions, or deletions. Polymorphisms may or may not result in detectable differences in gene expression, protein structure, or protein function. A polymorphism may alter one or more properties of the gene or gene products, including DNA or RNA stability, binding of transcriptional or translation factors to the DNA or RNA, interactions of the DNA or RNA with other parts of the nuclear or cytosolic cell machinery, or may confer a change upon the encoded polypeptide sequence which in turn may alter the polypeptide's biological activity. Identification of polymorphisms among various populations is desirable to tailor design of suitable antisense therapeutics, select antisense therapeutics to administer to a particular population, and also predict responsiveness to therapeutics.

A "polymorphic site" is a position within a genetic locus at which at least one alternative nucleotide sequence variation (e.g., substitution, insertion, or deletion) has been observed in a population, and includes the position on both complementary strands at the polymorphic site. The first identified form of the nucleotide sequence at the polymorphic site is sometimes called the reference sequence, and the alternative forms are called alternative or variant alleles (or "allelic variant"). The most commonly occurring form of the nucleotide sequence at the polymorphic site is also sometimes called the wild type allele. Polymorphic sites of the invention are listed in the following table along with their approximate frequency.

| Sequence variation | Position in SEQ ID NO: 1 | Approximate frequency of SNP detection out of 213 samples of diverse ancestry |
|---|---|---|
| Substitution of A to G | 27751 | 15% |
| Substitution of C to G | 27735 | <1% |
| Substitution of T to C | 27685 | 27% |
| Substitution of T to C | 27683 | |
| Substitution of T to C | 27679 | 40% |
| Substitution of C to T | 27634 | <1% |
| Substitution of G to A | 27627 | 2% |
| Substitution of T to C | 27618 | <1% |

The invention provides a variety of polynucleotides, including reverse complements, single or double stranded polynucleotides, RNA, DNA or mimetics thereof, and antisense compounds, as defined above, that either contain or specifically hybridize to a polymorphic sequence at one or more of these polymorphic sites. Such "sequence-specific"

polynucleotides can be used, alone or linked to other moieties, in a variety of areas. For example, the polynucleotides may be useful as therapeutic products for inhibiting gene expression, as probes or primers for detecting the polymorphic sequence as part of genotyping, diagnostic, pharmacogenomics and/or treatment methods, as part of arrays for screening, as part of diagnostic or therapeutic kits, or as tools for producing recombinant protein in host cells or transgenic organisms.

Methods of producing polynucleotides are well-known in the art, including chemical synthesis, cloning, and PCR amplification. The polymorphic polynucleotide sequences of the invention are preferably isolated, meaning in a form other than as part of an intact naturally occurring chromosome. Usually the polynucleotide sequences will also be purified, meaning at least about 50%, 75%, 80% or 90% pure or substantially free of other polynucleotide sequences that do not include an apolipoprotein B polynucleotide sequence or fragment thereof. The polynucleotide sequences can also be "recombinant", meaning flanked by one or more nucleotides with which they are not normally associated on a naturally occurring chromosome.

As noted elsewhere herein, polynucleotides or oligonucleotides may include modifications, including but not limited to modifications to the internucleoside linkages, modifications to the sugar moieties, and modified nucleobases, so long as the modified polynucleotides retain the ability to hybridize specifically to the target polymorphic site.

Such polynucleotides of the invention may be linked to a second moiety such as an additional nucleotide sequence for stabilization purposes or for directing transcription or translation, a moiety which facilitates linkage to a solid support (such as a microarray or microparticle), or a label to facilitate detection of the polynucleotide. Such labels include, without limitation, a radioactive label, a fluorescent label, a chemiluminescent label, a paramagnetic label, an enzymatic label, one member of a high affinity binding partner pair (such as biotin/avidin) or other labels known in the art. The second moiety may be attached to any position of the polynucleotide, so long as the polynucleotide retains its ability to hybridize to the polymorphic sites described herein. The second moiety may be linked to the polynucleotide after it has been generated, or may be linked to a component nucleobase that is then incorporated into the polynucleotide during synthesis or assembly. Polynucleotides of the invention can also be attached to the surface of a solid support through means not involving direct chemical linkage.

As used herein, "sequence-specific" means that the polynucleotide, oligonucleotide or antisense compound specifically hybridizes to one nucleotide sequence at a polymorphic site compared to another, e.g. preferentially hybridizes more strongly to the one sequence than to an alternative nucleotide sequence that has been observed in some individuals at that polymorphic site.

Sequence-specific polynucleotides when used for sequence detection must be capable of hybridizing to the polymorphic sites under conditions of stringency such as those employed in hybridization-based sequence determination methods, primer extension-based sequence determination methods, restriction site analysis, polynucleotide amplification methods, ligase-based sequencing methods, methods based on enzymatic detection of mismatches, microarray-based sequence determination methods, and other sequence determination methods known in the art. In a related embodiment, the invention also contemplates primer pairs comprising an oligonucleotide useful for amplification of a polymorphic site in the gene. Such primer pairs may comprise the polymorphic site or may surround it. Kits comprising such oligonucleotides and primer pairs are also contemplated.

In some embodiments, the invention provides sequence-specific polynucleotides comprising at least 15 contiguous nucleotides of SEQ ID NO: 1, or comprising at least 15 contiguous nucleotides of an allelic variant of SEQ ID NO: 1, said polynucleotide including at least one of:
C at position 27751 of SEQ ID NO: 1;
C at position 27735 of SEQ ID NO: 1;
G at position 27685 of SEQ ID NO: 1;
G at position 27683 of SEQ ID NO: 1;
G at position 27679 of SEQ ID NO: 1;
A at position 27634 of SEQ ID NO: 1;
T/U at position 27627 of SEQ ID NO: 1; or
G at position 27618 of SEQ ID NO: 1, wherein G is guanine, C is cytosine, T is thymine, U is uracil, and A is adenine.

In related embodiments, the invention further provides sequence-specific polynucleotides comprising at least 15 contiguous nucleotides of SEQ ID NO: 2, or comprising at least 15 contiguous nucleotides of an allelic variant of SEQ ID NO: 2, which is the reverse complement of SEQ ID NO: 1, said polynucleotide including at least one of:
G at position 15695 of SEQ ID NO: 2;
G at position 15711 of SEQ ID NO: 2;
C at position 15761 of SEQ ID NO: 2;
C at position 15763 of SEQ ID NO: 2;
C at position 15767 of SEQ ID NO: 2;
T/U at position 15812 of SEQ ID NO: 2;
A at position 15819 of SEQ ID NO: 2; or
C at position 15828 of SEQ ID NO: 2.

Such polynucleotides, including reverse complements, or single or double stranded polynucleotides, may range in length, for example, from at least 8, 12, 15, or 20 bases, such as 12-20, 15-30, 15-50, 50-100, 8-80, 8-30, 8-50, 12-50, or 12-30 contiguous bases, or may correspond to the full length of the encoding cDNA.

As part of these above aspects of the invention, the invention contemplates a sequence-specific oligonucleotide or antisense compound of no more than 100 nucleobases in length that hybridize to a portion of SEQ ID NO: 1 including at least one polymorphic site selected from the group consisting of:
C at position 27751 of SEQ ID NO: 1;
C at position 27735 of SEQ ID NO: 1;
G at position 27685 of SEQ ID NO: 1;
G at position 27683 of SEQ ID NO: 1;
G at position 27679 of SEQ ID NO: 1;
A at position 27634 of SEQ ID NO: 1;
T/U at position 27627 of SEQ ID NO: 1; or
G at position 27618 of SEQ ID NO: 1.

The invention also contemplates a sequence-specific oligonucleotides or antisense compound of no more than 100 nucleobases in length that hybridizes to a portion of SEQ ID NO: 2, which is the reverse complement of SEQ ID NO: 1, including at least one polymorphic site selected from the group consisting of:
G at position 15695 of SEQ ID NO: 2;
G at position 15711 of SEQ ID NO: 2;
C at position 15761 of SEQ ID NO: 2;
C at position 15763 of SEQ ID NO: 2;
C at position 15767 of SEQ ID NO: 2;
T/U at position 15812 of SEQ ID NO: 2;
A at position 15819 of SEQ ID NO: 2; or
C at position 15828 of SEQ ID NO: 2.

The invention further contemplates an oligonucleotide comprising about 15 to 30 contiguous nucleobases of an allelic variant of SEQ ID NO: 1, said allelic variant comprising at least one of:
C at position 27751 of SEQ ID NO: 1;
C at position 27735 of SEQ ID NO: 1;
G at position 27685 of SEQ ID NO: 1;
G at position 27683 of SEQ ID NO: 1;
G at position 27679 of SEQ ID NO: 1;
A at position 27634 of SEQ ID NO: 1;
T/U at position 27627 of SEQ ID NO: 1; or
G at position 27618 of SEQ ID NO: 1.

The invention also contemplates an oligonucleotide comprising about 15 to 30 contiguous nucleobases of an allelic variant of SEQ ID NO: 2, said allelic variant comprising at least one of:
G at position 15695 of SEQ ID NO: 2;
G at position 15711 of SEQ ID NO: 2;
C at position 15761 of SEQ ID NO: 2;
C at position 15763 of SEQ ID NO: 2;
C at position 15767 of SEQ ID NO: 2;
T/U at position 15812 of SEQ ID NO: 2;
A at position 15819 of SEQ ID NO: 2; or
C at position 15828 of SEQ ID NO: 2.

As noted above, such oligonucleotides or antisense compounds may be single or double stranded, may include reverse complements, may be RNA, DNA or mimetics, may be chemically modified, and may range in length, for example, from at least 8, 12, 15, or 20 bases, such as 12-20, 15-30, 15-50, 50-100, 8-80, 8-30, 8-50, 12-50, or 12-30 contiguous bases. In particular, an oligonucleotide or antisense compound that specifically hybridizes with a polymorphic sequence of a polymorphic site identified herein is useful for antisense therapy as described in other sections herein.

Where the polymorphism results in a change in the encoded amino acid sequence, expression vectors, host cells and recombinant organisms useful for producing the encoded protein are additionally contemplated. Polypeptides of limited length may also be prepared using chemical synthesis methods. Expression vectors may include nucleotide sequences that regulate transcription and/or translation, which may be inducible or constitutive, and which are preferably operably linked to coding sequence. Host cells include any prokaryotic, eukaryotic host cells known in the art, including bacteria, yeast, insect and mammalian cells. A large variety of techniques for expressing and purifying recombinant protein in host cell systems are known in the art. The polynucleotides of the invention can also be used to generate genetically modified (or transgenic) non-human animals or site specific gene modifications in cell lines using techniques known in the art. Such transgenic animals or cell lines include those in which the polymorphic gene is deleted or knocked out, those in which an exogenous polynucleotide comprising the polymorphism is stably inserted and transmitted to progeny, or those in which an endogenous polynucleotide comprising the polymorphism is operably linked to an exogenous regulatory sequence. Homologous recombination techniques are well known, and may utilize nucleic acid alone or as part of a suitable vector, such as viral vectors.

The variant polypeptides encoded by polynucleotides comprising one or more polymorphisms are also of interest, as are fragments thereof particularly antigenic epitopes, functional domains, binding sites, and other regions of interest, and including fusion proteins thereof. Polypeptides thus expressed are useful for protein structure analysis, for drug binding studies, and for screening candidate drugs to treat diseases related to apolipoprotein B activity. Antibodies specific for the variant polypeptides that differentiate between variant polypeptides and wild type polypeptide, including monoclonal antibodies and humanized or human antibodies, are also contemplated.

Expression assays can be used to detect differences in expression of polymorphisms with respect to tissue specificity, expression level, or expression in response to exposure to various substrates, and/or timing of expression during development. Expression assays may be performed in cell-free extracts, or by transforming cells with a suitable vector. Alterations in expression may occur in the basal level that is expressed in one or more cell types, or in the effect that an expression modifier has on the ability of the gene to be inhibited or induced. Expression levels of variant alleles are compared by various methods known in the art.

Screening can also be performed to determine if the polymorphisms described herein are genetically linked to other polymorphisms, to microsatellite markers, or to a phenotypic variant in apolipoprotein B activity or expression. Two polymorphisms may be in linkage disequilibrium, i.e. where alleles show non-random associations between genes even though individual loci are in Hardy-Weinberg equilibrium. Association of a polymorphism with a phenotypic trait (risk of a disease, severity or staging of a disease, or response to a drug) can also be identified by comparing the frequency of the polymorphism in a population exhibiting the trait to the frequency in a reference population; a higher frequency occurrence of the polymorphism in the population exhibiting the trait indicates that the trait is associated with the polymorphism. When such an association is established, the risk of disease, severity or staging of a disease, or response of an individual to a drug can then be predicted by determining the patient's genotype with respect to the polymorphism. Where there is a differential distribution of a polymorphism by racial background, guidelines for drug administration can be generally tailored to a particular ethnic group.

Identifying the presence or absence of a SNP is useful in methods of genotyping a human comprising the step of determining the identity of a nucleotide at a particular polymorphic site, in either the sense strand or its complement. The genotyping method may comprise identifying the nucleotide pair that is present at one or more polymorphic sites described herein. Genotyping compositions or kits of the invention comprises an oligonucleotide probe or pruner which is designed to specifically hybridize to a target region containing, or adjacent to, one of these novel polymorphic sites. A genotyping kit of the invention may further comprise a set of oligonucleotides designed to genotype other polymorphic sites.

Detection of the polymorphism can be performed by DNA or RNA sequence analysis of any patient sample that contains genetic material, including biopsied tissue, blood, skin, or other cell samples. The sample polynucleotide or desired segment thereof can be amplified or cloned by methods known in the art. The presence or absence of the polymorphism in question can be determined in a variety of ways known in the art. For example, the sequence of the sample polynucleotide may be determined by dideoxy sequencing or other conventional chemical analytical methods. Hybridization-based methods include Southern blots or dot blots, detecting a pattern of hybridization to sets of probes, ligase-based methods, primer extension-based methods, allele-specific amplification, Taqman, and other PCR-based methods. Other methods such as single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. If a polymorphism creates or destroys a recognition site for a restriction endonuclease (restriction fragment length polymorphism, RFLP), polymorphic sequence can be detected by digesting the sample with that endonuclease, and separating the products by size (e.g. using gel or capillary electrophoresis) to determine whether the fragment was digested. Mismatch cleavage detection using enzymes or chemical cleavage agents followed by detecting product size using electrophoretic or mass spectrometry methods can also be carried out. Moreover, in cases where the polymorphism of the invention is linked to another marker (such as another polymorphism or a microsatellite marker) then detecting the presence of the marker serves to detect the presence of the polymorphism.

In one preferred embodiment, the invention provides a method of analyzing a patient's polynucleotides for the presence or absence of a mutation comprising: (a) providing a test sample comprising polynucleotides or replicas thereof from a biological sample obtained from the patient; (b) contacting the test sample with a probe comprising at least 15 contiguous nucleotides of the nucleotide sequence of SEQ ID NO: 1 or the complement thereof, the probe comprising at least one of the nucleotides at a polymorphic site in SEQ ID NO: 1 or the complement thereof; and (c) determining if the test sample comprises a polynucleotide that specifically hybridizes to the probe.

In another preferred embodiment, the invention provides a method of analyzing a patient's polynucleotides for the presence or absence of a mutation using PCR comprising: (a) providing a test sample comprising polynucleotides or replicas thereof from a biological sample obtained from the patient; (b) contacting the test sample with at least one primer comprising at least 15 contiguous nucleotides of the nucleotide sequence of SEQ ID NO: 1 or its complement, and a polymerase, wherein the primer comprises at least one of the nucleotides at a polymorphic site in SEQ ID NO: 1 or the complement thereof; and (c) determining if a PCR product of the appropriate size is amplified.

Such analysis methods and related kits are useful for diagnostic, prognostic or pharmacogenomic purposes. Thus, the invention provides methods of (1) predicting risk of developing a disease condition (2) diagnosing a condition, and/or (3) predicting prognosis of a condition comprising: (a) analyzing a patient's polynucleotides to determine the identity of at least one of the nucleotides at a polymorphic site in SEQ ID NO: 1, wherein the presence or absence of the nucleotide correlates with a higher likelihood of developing said condition. The correlation may be based on statistically associating either the presence or absence of a single polymorphism (or multiple polymorphisms) with risk of developing a disease or condition, or with the diagnosis of a disease or condition, or with prognosis or staging of a disease or condition.

The invention further provides a method for selecting a treatment for a patient suffering from a disease or condition by determining whether or not a gene or genes in cells of the patient contain at least one polymorphism which is correlated to the effectiveness of the treatment of the disease or condition. The selection may be the selection of a method or methods which is/are more or less effective, safer, or toxic than certain other therapeutic regimens. The selection may involve either choice of a treatment to use or avoidance of a treatment. For example, a contra-indicated treatment should be avoided if it will not result in a therapeutic benefit, or if it will result in an excessive level of undesirable side effects. Thus, the frequency of the polymorphism itself may be correlated to the frequency of a beneficial therapeutic response to a drug or unresponsiveness to the drug, or it may be correlated to the frequency of an adverse event resulting from administration of the drug. Even where there the frequency of the polymorphism does not correspond closely with the frequency of a beneficial or adverse response, the polymorphism may still be useful for identifying a patient subset with high response or toxicity incidence. Preferably, the drug will be effective in more than 20%, 40% or 60% of individuals with one or more specific polymorphisms. Alternatively, the drug will be toxic or create clinically unacceptable side effects in more than 10%, 30%, 50%, 70% or 90% of individuals with one or more specific polymorphisms.

The invention thus provides a method of predicting a beneficial treatment for a patient comprising: (a) analyzing a patient's polynucleotides to determine the identity of at least one of the nucleotides at a polymorphic site in SEQ ID NO: 1 wherein the presence or absence of the nucleotide correlates with a prediction that the treatment will be beneficial. The method may further include selecting a suitable dosage amount and/or frequency of administration.

Similarly, the invention provides a method of predicting a contraindicated treatment for a patient comprising: (a) analyzing a patient's polynucleotides to determine the identity of at least one of the nucleotides at a polymorphic site in SEQ ID NO: 1, wherein the presence or absence of the nucleotide correlates with a prediction that the treatment will not be effective or will have significantly adverse effects. The correlation may be based on statistically associating either the presence or absence of a single polymorphism (or multiple polymorphisms) with a beneficial effect or contraindicated effect resulting from drug treatment.

One aspect of the invention specifically provides methods of treatment with sequence-specific antisense compounds comprising the step of detecting the presence of a polymorphism of the invention in the patient's sample prior to treatment with the desired sequence-specific compound, where detection of the polymorphism guides selection of the proper sequence-specific compound. For example, the presence of a polymorphism in a patient's genes may indicate that treatment with a compound that specifically hybridizes to the polymorphism may be beneficial. Similarly, the absence of a polymorphism in the patient's genes may mean that treatment with a compound that specifically hybridizes to the polymorphism is contraindicated.

While the present invention has been described with specificity in accordance with certain of its preferred embodiments, the following examples serve only to illustrate the invention and are not intended to limit the same. Each of the references, GENBANK® accession numbers, and the like recited in the present application is incorporated herein by reference in its entirety.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-N4-benzoyl-5-methylcytidin-3'-

O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-N$^4$-benzoyl-5-methyl-cytidine penultimate intermediate, [5'-O-(4,4'-Dimethoxytriphenylmethyl)-2'-O-(2-methoxyethyl)-N$^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-N$^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-N$^4$-isobutyrylguanosin-3'-O-yl]-2-cyanoethyl-N,N-diisopropylphosphoramidite (MOE G amidite), 2'-O-(Aminooxyethyl)nucleoside amidites and 2'-O-(dimethylaminooxyethyl)nucleoside amidites, 2'-(Dimethylaminooxyethoxy)nucleoside amidites, 5'-O-tert-Butyldiphenylsilyl-O$^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O-[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy)nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy(2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethyl-aminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M NH$_4$OAc solution. Phosphinate oligonucleotides are prepared as described in U.S. Pat. No. 5,508,270.

Alkyl phosphonate oligonucleotides are prepared as described in U.S. Pat. No. 4,469,863.

3'-Deoxy-3'-methylene phosphonate oligonucleotides are prepared as described in U.S. Pat. No. 5,610,289 or 5,625,050.

Phosphoramidite oligonucleotides are prepared as described in U.S. Pat. No. 5,256,775 or U.S. Pat. No. 5,366,878.

Alkylphosphonothioate oligonucleotides are prepared as described in published PCT applications PCT/US94/00902 and PCT/US93/06976 (published as WO 94/17093 and WO 94/02499, respectively).

3'-Deoxy-3'-amino phosphoramidate oligonucleotides are prepared as described in U.S. Pat. No. 5,476,925.

Phosphotriester oligonucleotides are prepared as described in U.S. Pat. No. 5,023,243.

Borano phosphate oligonucleotides are prepared as described in U.S. Pat. Nos. 5,130,302 and 5,177,198.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564.

Ethylene oxide linked oligonucleosides are prepared as described in U.S. Pat. No. 5,223,618.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.,* 1998, 120, 11820-11821; Matteucci, M. D. and Caruthers, M. H. *J. Am. Chem. Soc.,* 1981, 103, 3185-3191; Beaucage, S. L. and Caruthers, M. H. *Tetrahedron Lett.,* 1981, 22, 1859-1862; Dahl, B. J., et al., *Acta Chem. Scand,.* 1990, 44, 639-641; Reddy, M. P., et al., *Tetrahedrom Lett.,* 1994, 25, 4311-4314; Wincott, F. et al., *Nucleic Acids Res.,* 1995, 23, 2677-2684; Griffin, B. E., et al., *Tetrahedron,* 1967, 23, 2301-2313; Griffin, B. E., et al., *Tetrahedron,* 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 μl of each of the complementary strands of RNA oligonucleotides (50 uM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid, or for diagnostic or therapeutic purposes.

Example 4

Synthesis of Chimeric Compounds

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me]Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spectrophotometrically for yield and for purity by capillary electrophoresis and by mass spectrometry.

[2'-O-(2-Methoxyethyl)]-[2'-deoxy]-[2'-O-(Methoxyethyl)]Chimeric Phosphorothioate Oligonucleotides

[2'-O-(2-methoxyethyl)]-[2'-deoxy]-[2'-O-(methoxyethyl)]chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl)Phosphodiester]Chimeric Oligonucleotides

[2'-O-(2-methoxyethyl phosphodiester]-[2'-deoxy phosphorothioate]-[2'-O-(methoxyethyl)phosphodiester]chimeric oligonucleotides are prepared as per the above procedure for the 2'-O-methyl chimeric oligonucleotide with the substitution of 2'-O-(methoxyethyl)amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065.

Example 5

Design and Screening of Duplexed Antisense Compounds Targeting Apolipoprotein B

In accordance with the present invention, a series of nucleic acid duplexes comprising the antisense compounds of the present invention and their complements can be designed to target apolipoprotein B. The nucleobase sequence of the antisense strand of the duplex comprises at least an 8-nucleobase portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

In one embodiment, a duplex comprising an antisense strand having the sequence CGAGAGGCGGACGGGACCG (SEQ ID NO: 3), can be prepared with blunt ends (no single stranded overhang) as shown:

```
cgagaggcggacgggaccg     Antisense Strand (SEQ ID NO: 3)
|||||||||||||||||||
gctctccgcctgccctggc     Complement (SEQ ID NO: 4)
```

In another embodiment, both strands of the dsRNA duplex would be complementary over the central nucleobases, each having overhangs at one or both termini. For example, a duplex comprising an antisense strand having the sequence CGAGAGGCGGACGGGACCG (SEQ ID NO: 3) and having a two-nucleobase overhang of deoxythymidine(dT) would have the following structure:

```
  cgagaggcggacgggaccgTT    Antisense Strand (SEQ ID NO: 5)
  |||||||||||||||||||
TTgctctccgcctgccctggc      Complement (SEQ ID NO: 6)
```

Overhangs can range from 2 to 6 nucleobases and these nucleobases may or may not be complementary to the target nucleic acid. In another embodiment, the duplexes can have an overhang on only one terminus.

The RNA duplex can be unimolecular or bimolecular; i.e, the two strands can be part of a single molecule or may be separate molecules.

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed compounds are evaluated for their ability to modulate apolipoprotein B expression. When cells reach approximately 80% confluency, they are treated with duplexed compounds of the invention. For cells grown in 96-well plates, wells are washed once with 200 µL OPTI-MEM® 1 reduced-serum medium (Invitrogen Life Technologies, Carlsbad, Calif.) and then treated with 130 µL of OPTI-MEM® 1 containing 12 µg/mL LIPOFECTIN® (Invitrogen Life Technologies, Carlsbad, Calif.) and the desired duplex antisense compound (e.g. 200 nM) at a ratio of 6 µg/mL LIPOFECTIN® per 100 nM duplex antisense compound. After approximately 5 hours of treatment, the medium is replaced with fresh medium. Cells are harvested approximately 16 hours after treatment, at which time RNA is isolated and target reduction measured by real-time PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32 +/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis

96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis

96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

HepG2 Cells:

The human hepatoblastoma cell line HepG2 is available from the American Type Culture Collection (Manassas, Va.). HepG2 cells are routinely cultured in Eagle's MEM supplemented with 10% fetal bovine serum, non-essential amino acids, and 1 mM sodium pyruvate (Invitrogen Life Technologies, Carlsbad, Calif.). Cells are routinely passaged by trypsinization and dilution when they reach 90% confluence. Cells are seeded into 96-well plates (Falcon-Primaria #3872, BD Biosciences, Bedford, Mass.) at a density of approximately 7000 cells/well for use in antisense oligonucleotide transfection experiments. For Northern blotting or other analyses, cells may be seeded onto 100 mm or other standard tissue culture plates and treated similarly, using appropriate volumes of medium and oligonucleotide.

T-24 Cells:

The human transitional cell bladder carcinoma cell line T-24 is available from the American Type Culture Collection (ATCC) (Manassas, Va.). T-24 cells are routinely cultured in complete McCoy's 5A basal media supplemented with 10% fetal bovine serum, 100 units per mL penicillin, and 100 ug per mL streptomycin (media and supplements from Invitrogen Life Technologies, Carlsbad, Calif.). Cells are routinely passaged by trypsinization and dilution when they reach approximately 90% confluence. Cells are seeded into 96-well plates (Falcon-Primaria #353872, BD Biosciences, Bedford, Mass.) at a density of approximately 7000 cells/well for use in antisense oligonucleotide transfection experiments. For Northern blotting or other analysis, cells may be seeded onto 100 mm or other standard tissue culture plates and treated similarly, using appropriate volumes of medium and oligonucleotide.

A549 Cells:

The human lung carcinoma cell line A549 is available from the American Type Culture Collection (ATCC) (Manassas, Va.). A549 cells are routinely cultured in DMEM basal media (Invitrogen Corporation, Carlsbad, Calif.) supplemented with 10% fetal bovine serum, 100 units per mL penicillin, and 100 ug per mL streptomycin (media and supplements from Invitrogen Life Technologies, Carlsbad, Calif.). Cells are routinely passaged by trypsinization and dilution when they reach approximately 90% confluence. Cells are seeded into 96-well plates (Falcon-Primaria #353872, BD Biosciences, Bedford, Mass.) at a density of approximately 7000 cells/well for use in antisense oligonucleotide transfection experiments. For Northern blotting or other analysis, cells may be seeded onto 100 mm or other standard tissue culture plates and treated similarly, using appropriate volumes of medium and oligonucleotide.

NHDF Cells:

Human neonatal dermal fibroblast (NHDF) are available from the Clonetics Corporation (Walkersville, Md.). NHDFs are routinely maintained in Fibroblast Growth Medium (Clonetics Corporation, Walkersville, Md.) supplemented as recommended by the supplier. Cells are maintained for up to 10 passages as recommended by the supplier.

HEK Cells:

Human embryonic keratinocytes (HEK) are available from the Clonetics Corporation (Walkersville, Md.). HEKs are routinely maintained in Keratinocyte Growth Medium (Clonetics Corporation, Walkersville, Md.) formulated as recommended by the supplier. Cells are routinely maintained for up to 10 passages as recommended by the supplier.

Treatment with Antisense Compounds:

When cells reached 65-75% confluency, they are treated with oligonucleotide. Oligonucleotide is mixed with LIPOFECTIN® Invitrogen Life Technologies, Carlsbad, Calif.) in OPTI-MEM® 1 reduced serum medium (Invitrogen Life Technologies, Carlsbad, Calif.) to achieve the desired concentration of oligonucleotide and a LIPOFECTIN® concentration of 2.5 or 3 µg/mL per 100 nM oligonucleotide. This transfection mixture is incubated at room temperature for approximately 0.5 hours. For cells grown in 96-well plates, wells are washed once with 100 μL OPTI-MEM® 1 and then treated with 130 μL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture is replaced with fresh culture medium. Cells are harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG, SEQ ID NO: 7) which is targeted to human H-ras, or ISIS 18078, (GTGCGCGCGAGCCCGAAATC, SEQ ID NO: 8) which is targeted to human Jun-N-terminal kinase-2 (JNK2). ISIS 13920 is a chimeric oligonucleotide having a 9 nucleotide gap segment composed of 2'-deoxynucleotides, which is flanked on the 5' side and 3' sides by 3 nucleotide and 8 nucleotide wing segments, respectively. ISIS 18078 is a chimeric oligonucleotide having a 5 nucleotide gap segment composed of 2'-deoxynucleotides, which is flanked on the 5' and 3' sides by 5 nucleotide and 6 nucleotide wing segments, respectively. The wings are composed of 2'-O-methoxyethyl nucleotides. Both compounds have phosphorothioate internucleoside (backbone) linkages, and cytidines in the wing segments are 5-methylcytidines. For mouse or rat cells the positive control oligonucleotide is ISIS 15770 (ATGCAT-TCTGCCCCCAAGGA, SEQ ID NO: 9), a 2'-O-methoxyethyl gapmer (2'-O-methoxyethyls shown in bold), which is which is targeted to both mouse and rat c-raf. ISIS 15770 is a chimeric oligonucleotide having a 10 nucleotide gap segment composed of 2'-deoxynucleotides, which is flanked on the 5' side and 3' sides by 5 nucleotide wing segments. The wings are composed of 2'-O-methoxyethyl nucleotides. Internucleoside (backbone) linkages are phosphorothioate and cytidines in the wing segments are 5-methylcytidines. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of Apolipoprotein B Expression

Antisense modulation of apolipoprotein B expression can be assayed in a variety of ways known in the art. For example, apolipoprotein B mRNA levels can be quantitated by, e.g., Northern blot analysis, competitive polymerase chain reaction (PCR), or real-time PCR. Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM® 7700 Sequence Detection System, available from PE-Applied Biosystems, Foster City, Calif. and used according to manufacturer's instructions.

Protein levels of apolipoprotein B can be quantitated in a variety of ways well known in the art, such as immunoprecipitation, Western blot analysis (immunoblotting), ELISA or fluorescence-activated cell sorting (FACS). Antibodies directed to apolipoprotein B can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 11

Poly(A)+ mRNA Isolation

Poly(A)+ mRNA was isolated according to Miura et al., *Clin. Chem.*, 1996, 42, 1758-1764. Other methods for poly (A)+mRNA isolation are taught in, for example, Ausubel, F. M. et al., *Current Protocols in Molecular Biology*, Volume 1, pp. 4.5.1-4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY® 96 kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY® 96 well plate attached to a QIAvac manifold fitted with a waste collection tray and attached to a vacuum source. Vacuum was applied for 15 seconds. 1 mL of Buffer RW1 was added to each well of the RNEASY® 96 plate and the vacuum again applied for 15 seconds. 1 mL of Buffer RPE was then added to each well of the RNEASY® 96 plate and the vacuum applied for a period of 15 seconds. The Buffer RPE wash was then repeated and the vacuum was applied for an additional 10 minutes. The plate was then removed from the QIAvac manifold and blotted dry on paper towels. The plate was then re-attached to the QIAvac manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN® Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of Apolipoprotein B mRNA Levels

Quantitation of apolipoprotein B mRNA levels was determined by real-time quantitative PCR using the ABI PRISM® 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE™, FAM™, or VIC™, obtained from either Operon Technologies Inc., Alameda, Calif. or PE-Applied Biosystems, Foster City, Calif.) is attached to the 5' end of the probe and a quencher dye (e.g., TAMRA™, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM® 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

After isolation the RNA is subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time PCR are normalized using either the expression level of GAPDH, a gene whose expression is constant, or by quantifying total RNA using RIBOGREEN® (Molecular Probes, Inc. Eugene, Oreg.). GAPDH expression is quantified by real time PCR, by being run simultaneously with the target, multiplexing, or separately. Total RNA is quantified using RIBOGREEN® RNA quantification reagent from Molecular Probes. Methods of RNA quantification by RIBOGREEN® are taught in Jones, L. J., et al, *Analytical Biochemistry*, 1998, 265, 368-374.

In this assay, 175 µL of RIBOGREEN® working reagent (RIBOGREEN® reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human apolipoprotein B were designed to hybridize to a human apolipoprotein B sequence, using published sequence information (GENBANK® accession number NM_000384.1, incorporated herein as SEQ ID NO: 10). For human apolipoprotein B the PCR primers were:
forward primer: TGCTAAAGGCACATATGGCCT (SEQ ID NO: 11)
reverse primer: CTCAGGTTGGACTCTCCATTGAG (SEQ ID NO: 12) and the PCR probe was: FAM-CTTGTCA-GAGGGATCCTAACACTGGCCG-TAMRA (SEQ ID NO: 13) where FAM™ (PE-Applied Biosystems, Foster City, Calif.) is the fluorescent reporter dye) and TAMRA™ (PE-Applied Biosystems, Foster City, Calif.) is the quencher dye.
For human GAPDH the PCR primers were:
forward primer: GAAGGTGAAGGTCGGAGTC (SEQ ID NO: 14)
reverse primer: GAAGATGGTGATGGGATTTC (SEQ ID NO: 15) and the PCR probe was: 5' JOE-CAAGCTTC-CCGTTCTCAGCC-TAMRA 3' (SEQ ID NO: 16) where JOE™ (PE-Applied Biosystems, Foster City, Calif.) is the fluorescent reporter dye) and TAMRA™ (PE-Applied Biosystems, Foster City, Calif.) is the quencher dye.

Probes and primers to mouse apolipoprotein B were designed to hybridize to a mouse apolipoprotein B sequence, using published sequence information (GENBANK® accession number M35186, incorporated herein as SEQ ID NO: 17). For mouse apolipoprotein B the PCR primers were:
forward primer: CGTGGGCTCCAGCATTCTA (SEQ ID NO: 18)
reverse primer: AGTCATTTCTGCCTTTGCGTC (SEQ ID NO: 19) and the PCR probe was: 5' FAM-CCAATG-GTCGGGCACTGCTCAA-TAMRA 3'(SEQ ID NO: 20) where FAM™ (PE-Applied Biosystems, Foster City, Calif.) is the fluorescent reporter dye) and TAMRA™ (PE-Applied Biosystems, Foster City, Calif.) is the quencher dye. For mouse GAPDH the PCR primers were:
forward primer: GGCAAATTCAACGGCACAGT (SEQ ID NO: 21)
reverse primer: GGGTCTCGCTCCTGGAAGAT (SEQ ID NO: 22) and the PCR probe was: 5' JOE-AAGGC-CGAGAATGGGAAGCTTGTCATC-TAMRA 3' (SEQ ID NO: 23) where JOE™ (PE-Applied Biosystems, Foster City, Calif.) is the fluorescent reporter dye) and TAMRA™ (PE-Applied Biosystems, Foster City, Calif.) is the quencher dye.

Example 14

Northern Blot Analysis of Apolipoprotein B mRNA Levels

Eighteen hours after antisense treatment, cell monolayers were washed twice with cold PBS and lysed in 1 mL RNA-ZOL® (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND®-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER® UV Crosslinker 2400 (Stratagene, Inc, La Jolla, Calif.) and then robed using QUICKHYB® hybridization solution (Stratagene, La Jolla, Calif.) using manufacturer's recommendations for stringent conditions.

To detect human apolipoprotein B, a human apolipoprotein B specific probe was prepared by PCR using the forward primer TGCTAAAGGCACATATGGCCT (SEQ ID NO: 11) and the reverse primer CTCAGGTTGGACTCTCCAT-TGAG (SEQ ID NO: 12). To normalize for variations in loading and transfer efficiency membranes were stripped and probed for human glyceraldehyde-3-phosphate dehydrogenase (GAPDH) RNA (Clontech, Palo Alto, Calif.).

To detect mouse apolipoprotein B, a human apolipoprotein B specific probe was prepared by PCR using the forward primer CGTGGGCTCCAGCATTCTA (SEQ ID NO: 18) and the reverse primer AGTCATTTCTGCCTTTGCGTC (SEQ ID NO: 19). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER® and IMAGEQUANT® Software V3.3 (Molecular Dynamics, Sunnyvale, Calif.). Data was normalized to GAPDH levels in untreated controls.

Example 15

Western Blot Analysis of Apolipoprotein B Protein Levels

Western blot analysis (immunoblot analysis) was carried out using standard methods. Cells were harvested 16-20 h after oligonucleotide treatment, washed once with PBS, suspended in Laemmli buffer (100 ul/well), boiled for 5 minutes and loaded on a 16% SDS-PAGE gel. Gels were run for 1.5 hours at 150 V, and transferred to membrane for western blotting. Appropriate primary antibody directed to apolipoprotein B was used, with a radiolabelled or fluorescently labeled secondary antibody directed against the primary antibody species. Bands were visualized using a PHOSPHO-RIMAGER® (Molecular Dynamics, Sunnyvale Calif.) or the ECL PLUS® chemiluminescent detection system (Amersham Biosciences, Piscataway, N.J.).

Example 16

Antisense Inhibition of Apolipoprotein B Expression

U.S. Application Publication No. 20040214325 published Oct. 28, 2004 and International Patent Publication WO2004044181 published May 27, 2004, the disclosures and particularly the examples of which are hereby incorporated by reference in their entirety, describe the activity in vitro and in vivo of a variety of different antisense compounds, including dsRNA and chimeric phosphorothioate oligonucleotides, designed to target different regions of the human, mouse, rabbit and monkey apolipoprotein B RNA.

A number of different compounds demonstrated at least 10%, at least 30%, and/or at least 50% inhibition of apolipoprotein B expression. The target regions to which these preferred sequences are complementary are herein referred to as "preferred target segments" and are therefore preferred for targeting by compounds of the present invention. Where sequences are shown to contain thymine (T) one of skill in the art will appreciate that thymine (T) is generally replaced by uracil (U) in RNA sequences.

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of apolipoprotein B.

According to the present invention, antisense compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

Example 17

Design of Phenotypic Assays for the Use of Apolipoprotein B Inhibitors

Once apolipoprotein B inhibitors have been identified by the methods disclosed herein, the compounds are further investigated in one or more phenotypic assays, each having measurable endpoints predictive of efficacy in the treatment of a particular disease state or condition. Phenotypic assays, kits and reagents for their use are well known to those skilled in the art and are herein used to investigate the role and/or association of apolipoprotein B in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with apolipoprotein B inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the apolipoprotein B inhibitors. Hallmark genes, or those genes suspected to be associated with a specific disease state, condition, or phenotype, are measured in both treated and untreated cells.

Example 18

Activity in Animal Models

U.S. Application Publication No. 20040214325 published Oct. 28, 2004 and International Patent Publication WO2004044181 published May 27, 2004, the disclosures and particularly the examples of which are hereby incorporated by reference in their entirety, also describe the in vitro and in vivo biological effects of antisense inhibition of apolipoprotein B expression in mice and monkeys.

Treatment with ISIS 147764, a mouse-specific oligonucleotide, lowered cholesterol as well as LDL and HDL lipoproteins and serum glucose in both lean and high fat mice. The effects demonstrated are, in fact, due to the inhibition of apolipoprotein B expression as supported by the decrease in mRNA levels. No significant changes in liver enzyme levels were observed, indicating that the antisense oligonucleotide was not toxic to either treatment group.

Treatment of high fat fed mice with ISIS 147764 decreased apolipoprotein B protein expression in liver in a dose-dependent manner, reduced serum cholesterol and triglycerides, lowered levels of serum HDL, LDL and VLDL lipoproteins, reduced serum glucose levels, and decreased fat pad weight.

Treatment of apo E knockout mice with ISIS 147764 lowered glucose and cholesterol as well as serum HDL, LDL and VLDL lipoproteins. Further, these decreases correlated with a decrease in both protein and RNA levels of apolipoprotein B, demonstrating an antisense mechanism of action. No significant changes in liver enzyme levels were observed, indicating that the antisense oligonucleotide was not toxic to either treatment group.

LDL receptor-deficient mice (LDLr(−/−)mice), a strain that cannot edit the apolipoprotein B mRNA and therefore synthesize exclusively apolipoprotein B-100, have markedly elevated LDL cholesterol and apolipoprotein B-100 levels and develop extensive atherosclerosis. ISIS 147764 was able to lower cholesterol, triglycerides, and mRNA levels in a dose-dependent manner in both male and female LDLr(−/−) mice while the 4-base mismatch ISIS 270906 was not able to do this.

C57BL/6NTac-TgN(APOB100) transgenic mice have the human apolipoprotein B gene "knocked-in". These mice express high levels of human apolipoprotein B 100 resulting in mice with elevated serum levels of LDL cholesterol. Treatment with either of these oligonucleotides targeted to the human apolipoprotein B which is expressed in these mice markedly decreased the mRNA levels of the human apolipoprotein, while the levels of the endogenous mouse apolipoprotein B were unaffected, indicating that these oligonucleotides exhibit specificity for the human apolipoprotein B. Immunoblot analysis of liver protein samples reveals a reduction in the expression of both forms of human apolipoprotein B, apolipoprotein B-100 and apolipoprotein B-48. Mouse apolipoprotein B levels in liver were not significantly changed. LDL-cholesterol levels were significantly reduced.

ob/ob mice have a mutation in the leptin gene which results in obesity and hyperglycemia. Treatment of ob/ob mice receiving a high fat and cholesterol diet with ISIS 147483 and 147764 were both able to lower apolipoprotein B mRNA levels, as well as glucose, cholesterol, and triglyceride levels Toxicity studies in mice revealed no severe toxic effects. In vitro assays showed that ISIS 301012 does not possess immunostimulatory activity.

In Cynomolgus monkeys, antisense inhibition by ISIS 301012 was compared to that of ISIS 326358, which is a perfect match to the Cynomolgus monkey apolipoprotein B sequence to which ISIS 301012 hybridizes. These data demonstrate that both ISIS 326359 and ISIS 301012 (despite two mismatches with the Cynomolgus monkey apolipoprotein B sequence) can inhibit the expression of apolipoprotein B mRNA in Cynomolgus monkey primary hepatocytes, in a dose- and time-dependent manner.

TABLE 1

Effects of antisense inhibition by ISIS 301012 in lean Cynomolgus monkeys

|  | Intravenous delivery | | | Subcutaneous injection | |
| --- | --- | --- | --- | --- | --- |
|  | 2 mg/kg | 4 mg/kg | 12 mg/kg | 3.5 mg/kg | 20 mg/kg |
| apolipoprotein B expression % change normalized to saline | −45 | −76 | −96 | N.D. | −94 |
| antisense oligonucleotide concentration µg/g | 92 | 179 | 550 | N.D. | 855 |

| Lipid parameters, % change normalized to untreated baseline value | Saline | 2 mg/kg | 4 mg/kg | 12 mg/kg | 3.5 mg/kg | 20 mg/kg |
| --- | --- | --- | --- | --- | --- | --- |
| Total cholesterol | +1 | −6 | −2 | −2 | +5 | −5 |
| LDL-cholesterol | +17 | +15 | +9 | +3 | −4 | −16 |
| HDL-cholesterol | −11 | −23 | −15 | −8 | +13 | +5 |
| LDL/HDL | +62 | +94 | +38 | +44 | −15 | −19 |
| Total cholesterol/HDL | +30 | +44 | +22 | +21 | −7 | −10 |
| Triglyceride | +37 | +26 | +32 | +15 | +1 | −3 |
| LDL Particle concentration | +15 | +8 | +8 | −11 | −14 | −21 |

These data show that ISIS 301012 inhibits apolipoprotein B expression in a dose-dependent manner in a primate species and concomitantly lowers lipid levels at higher doses of ISIS 301012. Furthermore, these results demonstrate that antisense oligonucleotide accumulates in the liver in a dose-dependent manner.

Example 19

Identification of SNPs

Polymorphisms were discovered by comparing the apolipoprotein B genomic sequences of 213 DNA samples. An initial analysis of 23 DNA samples and a followup analysis of an additional 190 DNA samples was conducted to identify SNPs in the target region of ISIS 301012 (exon 20, boundary of intron 20). The 190 DNA samples came from individuals self-identified as belonging to one of four major population groups: Caucasian (47 individuals), African descent (48 individuals), Asian (47 individuals), or Hispanic (48 individuals). All samples were analyzed in replicates using SEQUENOM's MASSARRAY® approach including MASSCLEAVE® biochemistry.

Seven previously unknown SNPs with varying frequencies were discovered in an approximately 541 bp portion of the ISIS 301012 target region, none in the antisense or exon regions. The SNPs and their positions and frequencies are set forth in Table 2 below.

TABLE 2

Identification of SNPs

| Sequence variation | Position in SEQ ID NO: 1 | Approximate frequency of SNP detection out of 213 samples of diverse ancestry |
| --- | --- | --- |
| Substitution of A to G | 27751 | 15% |
| Substitution of C to G | 27735 | <1% |
| Substitution of T to C | 27685 | 27% |
| Substitution of T to C | 27683 | |
| Substitution of T to C | 27679 | 40% |
| Substitution of C to T | 27634 | <1% |
| Substitution of G to A | 27627 | 2% |
| Substitution of T to C | 27618 | <1% |

The frequency of the T/C substitution at position 27679 and the T/C substitution at 27685 was significantly lower in Asian DNA samples compared to other ethnic groups. See table below.

| Position in SEQ ID NO: 1 | Asian | African American | Hispanic | Caucasian |
| --- | --- | --- | --- | --- |
| 27685 | 9.8% | 32.4% | 42.2% | 32.6% |
| 27679 | 19.7% | 45.6% | 43.8% | 48.6% |

The C/T substitution at position 27634 was only present in Asian samples. It was detected in one heterozygote Asian sample and one homozygote Asian sample.

The distribution of the A/G substitution at position 27751 does not match the Hardy-Weinberg disequilibrium; all samples carrying this sequence variation are heterozygote.

The G/A substitution at position 27627 was found only in four samples of African American origin.

The T/C substitution at position 27618 was found in one African American sample.

What is claimed is:

1. An antisense compound 15 to 30 nucleobases in length which specifically hybridizes with an allelic variant of a nucleic acid of SEQ ID NO: 1 encoding human apolipoprotein B, wherein said compound inhibits the expression of apolipoprotein B mRNA by at least 10% and wherein said compound is targeted to a region that includes at least one nucleobase selected from the group consisting of:
   (a) C at position 27751 of SEQ ID NO: 1;
   (b) G at position 27685 of SEQ ID NO: 1;
   (c) G at position 27683 of SEQ ID NO: 1;
   (d) G at position 27679 of SEQ ID NO: 1;
   (e) A at position 27634 of SEQ ID NO: 1;
   (f) T/U at position 27627 of SEQ ID NO: 1; and
   (g) G at position 27618 of SEQ ID NO: 1,
wherein G is guanine, C is cytosine, T is thymine, U is uracil, and A is adenine; and wherein said antisense compound comprises a complementary nucleobase at said position.

2. The antisense compound of claim 1 which is 20 nucleobases in length.

3. The antisense compound of claim 1 comprising an oligonucleotide.

4. The antisense compound of claim 3 comprising a DNA oligonucleotide.

5. The antisense compound of claim 3 comprising an RNA oligonucleotide.

6. The antisense compound of claim 3 comprising a chimeric oligonucleotide.

7. The antisense compound of claim 3 wherein at least a portion of said compound hybridizes with RNA to form an oligonucleotide-RNA duplex.

8. The antisense compound of claim 1 having at least 80%, at least 85%, at least 90% or, at least 95% or at least 99% complementarity with said nucleic acid molecule encoding apolipoprotein B.

9. The antisense compound of claim 1 having one, two or more types of modifications, wherein the modification comprises a modified internucleoside linkage, sugar moiety, or nucleobase.

10. The antisense compound of claim 1 having at least one 2'-O-methoxyethyl sugar moiety.

11. The antisense compound of claim 1 having at least one phosphorothioate internucleoside linkage.

12. The antisense compound of claim 1 wherein at least one cytosine is a 5-methylcytosine.

13. A method of inhibiting the expression of apolipoprotein B in a cell or tissue comprising contacting said cell or tissue with the antisense compound of claim 1 so that expression of apolipoprotein B is inhibited.

14. A method of screening for a modulator of apolipoprotein B, the method comprising the steps of contacting a preferred target segment of a nucleic acid molecule encoding apolipoprotein B with one or more candidate modulators of apolipoprotein B, and identifying one or more modulators of apolipoprotein B expression which modulate the expression of apolipoprotein B, wherein said preferred target segment comprises at least one of:
   (a) C at position 27751 of SEQ ID NO: 1;
   (b) C at position 27735 of SEQ ID NO: 1;
   (c) G at position 27685 of SEQ ID NO: 1;
   (d) G at position 27683 of SEQ ID NO: 1;
   (e) G at position 27679 of SEQ ID NO: 1;
   (f) A at position 27634 of SEQ ID NO: 1;
   (g) T/U at position 27627 of SEQ ID NO: 1; or
   (h) G at position 27618 of SEQ ID NO: 1,
wherein G is guanine, C is cytosine, T is thymine, U is uracil, and A is adenine.

15. The method of claim 14 wherein the modulator of apolipoprotein B expression comprises an oligonucleotide, an antisense oligonucleotide, a DNA oligonucleotide, an RNA oligonucleotide, an RNA oligonucleotide having at least a portion of said RNA oligonucleotide capable of hybridizing with RNA to form an oligonucleotide-RNA duplex, or a chimeric oligonucleotide.

16. A method of treating an animal having a disease or condition treatable by reducing apolipoprotein B, comprising administering to said animal a therapeutically or prophylactically effective amount of the antisense compound of claim 1 so that expression of apolipoprotein B is inhibited.

17. The method of claim 16, wherein the disease or condition is a disorder of lipid metabolism.

18. An antisense compound 15 to 30 nucleobases in length which specifically hybridizes with an allelic variant of a nucleic acid of SEQ ID NO: 1 encoding human apolipoprotein B, wherein said compound inhibits the expression of apolipoprotein B mRNA by at least 10% and wherein said compound is targeted to a region that includes a C at position 27735 of SEQ ID NO: 1, and wherein said antisense compound has one, two or more types of modifications, wherein the modification comprises a modified internucleoside linkage, sugar moiety, or nucleobase; and wherein the antisense compound is a chimeric antisense compound comprising:
   (i) a gap segment consisting of linked deoxynucleotides,
   (ii) a 5' wing segment consisting of linked nucleotides, and
   (iii) a 3' wing segment consisting of linked nucleotides,
wherein the gap segment is positioned between the 5' wing segment and the 3' wing segment.

19. The antisense compound of claim 18 which is 20 nucleobases in length.

20. The antisense compound of claim 18 comprising an oligonucleotide.

21. The antisense compound of claim 20 comprising a DNA oligonucleotide.

22. The antisense compound of claim 20 comprising an RNA oligonucleotide.

23. The antisense compound of claim 20 comprising a chimeric oligonucleotide.

24. The antisense compound of claim 20 wherein at least a portion of said compound hybridizes with RNA to form an oligonucleotide-RNA duplex.

25. The antisense compound of claim 18 having at least 80%, at least 85%, at least 90% or, at least 95% or at least 99% complementarity with said nucleic acid molecule encoding apolipoprotein B.

26. The antisense compound of claim 18 having at least one 2'-O-methoxyethyl sugar moiety.

27. The antisense compound of claim 18 having at least one phosphorothioate internucleoside linkage.

28. The antisense compound of claim 18 wherein at least one cytosine is a 5-methylcytosine.

29. A method of inhibiting the expression of apolipoprotein B in a cell or tissue comprising contacting said cell or tissue with an antisense compound so that expression of apolipoprotein B is inhibited, wherein said antisense compound is 15 to 30 nucleobases in length and specifically hybridizes with an allelic variant of a nucleic acid of SEQ ID NO: 1 encoding human apolipoprotein B, wherein said antisense compound inhibits the expression of apolipoprotein B mRNA by at least 10%, wherein said antisense compound is targeted to a region that includes a C at position 27735 of SEQ ID NO: 1, and wherein said antisense compound has one, two or more types of modifications, wherein the modification comprises a modified internucleoside linkage, sugar moiety, or nucleobase.

30. The antisense compound of claim 18, wherein the gap segment is flanked on both the 5' and 3' sides by wing segments of the same length.

31. The antisense compound of claim 18, wherein the gap segment is flanked on both the 5' and 3' sides by wing segments of different lengths.

32. The antisense compound of claim 30, wherein the antisense compound is 20 nucleobases in length, and wherein:
  (i) the gap segment is 8 nucleotides in length, and the 5' and 3' wing segments are each 6 nucleotides in length;
  (ii) the gap segment is 10 nucleotides in length, and the 5' and 3' wing segments are each 5 nucleotides in length;
  (iii) the gap segment is 12 nucleotides in length, and the 5' and 3' wing segments are each 4 nucleotides in length;
  (iv) the gap segment is 14 nucleotides in length, and the 5' and 3' wing segments are each 3 nucleotides in length;
  (v) the gap segment is 16 nucleotides in length, and the 5' and 3' wing segments are each 2 nucleotides in length; or
  (vi) the gap segment is 18 nucleotides in length, and the 5' and 3' wing segments are each 1 nucleotide in length.

33. The antisense compound of claim 31, wherein the antisense compound is 20 nucleobases in length, and wherein the gap segment is 10 nucleotides in length, flanked on one side by a wing segment 6 nucleotides in length and flanked on the other side by a wing segment 4 nucleotides in length.

* * * * *